United States Patent
Jinbo et al.

[11] Patent Number: 5,912,247
[45] Date of Patent: Jun. 15, 1999

[54] QUINAZOLINE COMPOUND AND ANTI-TUMOR AGENT CONTAINING SAID COMPOUND AS AN ACTIVE INGREDIENT

[75] Inventors: Yoshikazu Jinbo; Tomohiro Miyasaka; Yoshiaki Ikeda; Takashi Sekida; Kei Naruse; Masayuki Ando; Shigeru Iwaki; Kohichiro Yoshino, all of Osaka-fu, Japan

[73] Assignee: Kanebo, Ltd., Tokyo-To, Japan

[21] Appl. No.: 08/916,946

[22] Filed: Aug. 20, 1997

Related U.S. Application Data

[63] Continuation of application No. 08/638,525, Apr. 26, 1996, abandoned.

[30] Foreign Application Priority Data

May 16, 1995 [JP] Japan .................................. 7-142559
May 16, 1995 [JP] Japan .................................. 7-142560

[51] Int. Cl.$^6$ ....................... A61K 31/505; C07D 403/04
[52] U.S. Cl. ........................................... 514/254; 544/287
[58] Field of Search ........................ 544/287; 514/260, 514/254

[56] References Cited

U.S. PATENT DOCUMENTS

| | | | |
|---|---|---|---|
| 3,609,152 | 9/1971 | Hess et al. ........................... | 260/256.5 |
| 3,812,127 | 5/1974 | Cronin et al. ........................... | 260/268 |
| 4,588,725 | 5/1986 | Neuman et al. ........................ | 514/254 |
| 4,672,116 | 6/1987 | Bandurco et al. ...................... | 544/286 |
| 4,877,790 | 10/1989 | Iemura et al. ......................... | 514/260 |

FOREIGN PATENT DOCUMENTS 07138238   5/1995   Japan .

OTHER PUBLICATIONS

Cancer Chemotherapeutic Agents, Medical Research Inc., Japan, pp. 446–447, Feb. 20, 1993.

Hori, et al., Novel 4–Substituted 2–Piperazinylquinazolines as Potent Anticonvulsive and Anthiypoxic Agents, *Chem. Pharm. Bull*, 38, (5), 1990, pp. 1286–1291.

Hori, et al., "Potential Nootropic Agents, 4–Alkoxy–2–(1–piperaxinyl)quinazoline Derivatives", *Chem. Pharm. Bull*, 39, (2), 1991, pp. 367–371.

*Primary Examiner*—Richard L. Raymond
*Attorney, Agent, or Firm*—Merchant, Gould, Smith, Edell, Welter & Schmidt

[57] ABSTRACT

A quinazoline compound of the formula (I):

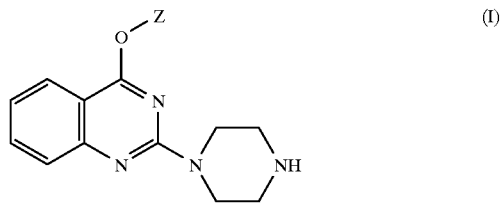

wherein Z means a group of the formula:

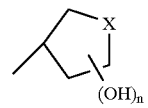

(X is $CH_2$, CHOH, $CHOCH_3$, or O, and n is 1 to 3), or a group of the formula:

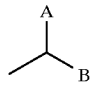

(A is H or $CH_3$, and B is —$CH_2OH$, or ethyl having 1 or 2 OH, or propyl having 2 or 3 OH), or a salt thereof, which are useful as anti-tumor agent, and a pharmaceutical composition containing the compound as an active ingredient.

34 Claims, No Drawings

QUINAZOLINE COMPOUND AND ANTI-TUMOR AGENT CONTAINING SAID COMPOUND AS AN ACTIVE INGREDIENT

This is a Continuation of application Ser. No. 08/638,525, filed Apr. 26, 1996, now abandoned.

TECHNICAL FIELD

This invention relates to a novel quinazoline compound and an anti-tumor agent containing said compound as an active ingredient. More particularly, it relates to a quinazoline compound of the formula (I):

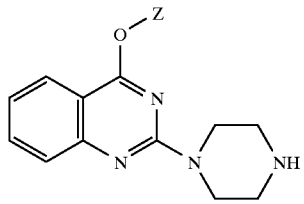

wherein Z means a group of the formula:

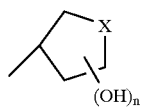

(wherein X means methylene

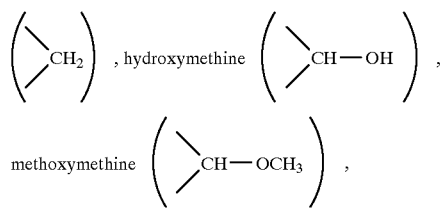

or an oxygen atom, and n is an integer of 1 to 3), or a group of the formula:

(wherein A is a hydrogen atom or methyl, and B is hydroxymethyl, or ethyl having one or two hydroxy substituents, or propyl having two or three hydroxy substituents),
or a pharmaceutically acceptable acid addition salt thereof, and an anti-tumor agent containing said compound as an active ingredient.

PRIOR ART

Studies on anti-tumor agents have hitherto been done mainly in view of attacking tumor cells directly, but the thus found anti-tumor agents damage not only the tumor cells but also the growth of normal cells, and hence, they have disadvantage defects, i.e. severe side effects such as toxicity to bone marrow.

U.S. Pat. No. 4,877,790 discloses 2-(4-allylpiperazin-1-yl)-4-[(1-pentyl)oxy]quinazoline or a pharmaceutically acceptable acid addition salt thereof, a process for the production thereof, and also utility thereof as a cerebral dysfunction remedying agent in senile dementia. The present inventors had found and reported that the monofumarate of said 2-(4-allylpiperazin-1-yl)-4-[(1-pentyl) oxy] quinazoline (Compound No. 5666) is useful for the treatment of solid tumor [cf. Cancer Chemotherapeutic Agents, page 447, issued by Medical Research Inc., Japan, Feb. 20, 1993].

BRIEF DESCRIPTION OF THE INVENTION

The present inventors have studied to find a new compound which can exhibit excellent anti-tumor activity on the basis of a different mechanism from that of the known compounds which directly attack the tumor cells. Aiming at the fact that flow of blood into the tumor tissues is essential for the growth of solid tumors, the present inventors have intensively studied various compounds which can inhibit the flow of blood into the tumor tissues, wherein the screening of the compounds having inhibitory activity of the flow of blood into tumor tissues has been done based on inhibitory activity of dye accumulation (Evans blue) into tumor tissues in the light of the fact that the dye injected via the tail vein of a tumor bearing animal is transferred into tumor tissues together with blood. By the study based on the inhibitory activity of dye accumulation in mouse solid tumor (i.e. colon 26), it has been found that the above-mentioned compound (No. 5666) has such an inhibitory activity and hence is useful as an anti-tumor agent.

However, the present inventors have further found that this compound showed disadvantage hemolytic activity, and hence, have further studied to find other new compounds which can exhibit the desired inhibitory activity of dye accumulation without showing any hemolytic activity. As a result, it has been found that the novel quinazoline compound of the formula (I) and pharmaceutically acceptable acid addition salts thereof satisfy these requirements and can show excellent anti-tumor activity.

An object of the invention is to provide a novel quinazoline compound and a pharmaceutically acceptable acid addition salt thereof which have excellent anti-tumor activity. Another object of the invention is to provide a process for the production of the quinazoline compound. A further object of the invention is to provide a pharmaceutical composition for the treatment of tumors which contains as the active ingredient said quinazoline compound. A still further object of the invention is to provide a use of the quinazoline compound for the treatment of various tumors.

DETAILED DESCRIPTION OF THE INVENTION

The quinazoline compound of the present invention includes the quinazoline compounds of the following formulae (I-A) and (I-B) and pharmaceutically acid addition salts thereof.

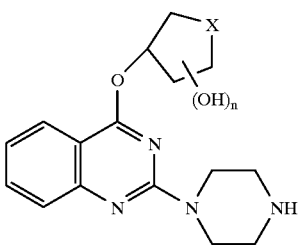

(I-A)

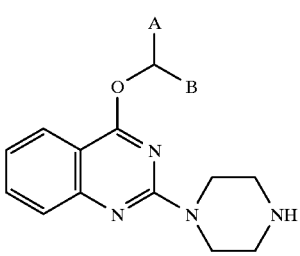

(I-B)

wherein X, n, A and B are as defined above.

The quinazoline compounds of the present invention include stereoisomers and/or optical isomers based on the asymmetric carbon on the substituents at the 4-position of the quinazoline nucleus, and the present invention includes also these stereoisomers and/or optical isomers as well as their pharmaceutically acceptable acid addition salts.

The pharmaceutically acceptable acid addition salts include salts with inorganic acids such as hydrochloride, or sulfate, and salts of organic acids such as acetate, fumarate, maleate, tartrate, or succinate.

Suitable examples of the quinazoline compounds of the formula (I-A) are as listed below, as well as their salts such as hydrochloride, acetate, or fumarate.

(1A) 4-[trans-(2-Hydroxycyclopentan-1-yl)oxy]-2-(1-piperazinyl)quinazoline
(2A) 4-[cis-(2-Hydroxycyclopentan-1-yl)oxy]-2-(1-piperazinyl)quinazoline
(3A) 4-[(3-Hydroxycyclopentan-1-yl)oxy]-2-(1-piperazinyl)quinazoline
(4A) 4-[(1S,2S)-(2-Hydroxycyclopentan-1-yl)oxy]-2-(1-piperazinyl)quinazoline
(5A) 4-[(1R,2R)-(2-Hydroxycyclopentan-1-yl)oxy]-2-(1-piperazinyl)quinazoline
(6A) 4-[trans-(4-Hydroxytetrahydrofuran-3-yl)oxy]-2-(1-piperazinyl)quinazoline
(7A) 4-[cis-(4-Hydroxytetrahydrofuran-3-yl)oxy]-2-(1-piperazinyl)quinazoline
(8A) 4-[(3S,4S)-(4-Hydroxytetrahydrofuran-3-yl) -oxy]-2-(1-piperazinyl)quinazoline
(9A) 4-[(3R,4R)-(4-Hydroxytetrahydrofuran-3-yl)-oxy]-2-(1-piperazinyl)quinazoline
(10A) 4-[(t-2,t-3-Dihydroxycyclopentan-r-1-yl)oxy]-2-(1-piperazinyl)quinazoline
(11A) 4-[(t-3,t-4-Dihydroxycyclopentan-r-1-yl)oxy]-2-(1-piperazinyl)quinazoline
(12A) 4-[(c-3,c-4-Dihydroxycyclopentan-r-1-yl)oxy]-2-(1-piperazinyl)quinazoline
(13A) 4-[(t-2,t-3,c-4-Trihydroxycyclopentan-r-1-yl)oxy]-2-(1-piperazinyl)quinazoline
(14A) 4-[(1S,2S,3S,4R)-(2,3,4-Trihydroxycyclopentan-1-yl)oxy]-2-(1-piperazinyl)quinazoline
(15A) 4-[(1R,2R,3R,4S)-(2,3,4-Trihydroxycyclopentan-1-yl)oxy]-2-(1-piperazinyl)quinazoline
(16A) 4-[(1S,2S,3R,4R)-(2,3-Dihydroxy-4-methoxy-cyclopentan-1-yl)oxy]-2-(1-piperazinyl)quinazoline
(17A) 4-[(1R,2R,3S,4S)-(2,3-Dihydroxy-4-methoxy-cyclopentan-1-yl)oxy]-2-(1-piperazinyl)quinazoline Among the above quinazoline compounds (I-A), the preferred ones are the compounds of the formula (I-A) wherein n is 1 or 2, X is methylene, hydroxymethine, methoxymethine or an oxygen atom, and their pharmaceutically acceptable acid addition salts. Examples of these preferred compounds are (11A) 4-[(t-3,t-4-dihydroxycyclopentan-r-1-yl)oxy]-2-(1-piperazinyl)-quinazoline, (17A) 4-[(1R,2R,3S,4S)-(2,3-dihydroxy-4-methoxy-cyclopentan-1-yl)oxy]-2-(1-piperazinyl) quinazoline, (9A) 4-[(3R,4R)-(4-hydroxytetrahydrofuran-3-yl) oxy]-2-(1-piperazinyl)quinazoline, (8A) 4-[(3S,4S)-(4-hydroxytetrahydrofuran-3-yl) oxy]-2-(1-piperazinyl) quinazoline, and their salts such as hydrochloride, acetate, fumarate, particularly hydrochloride.

In the quinazoline compounds of the formula (I-B), the preferred A group is hydrogen atom, and the preferred B group is n-propyl having two or three hydroxy substituents, the more preferred B group being n-propyl having two hydroxy substituents. Suitable examples of the quinazoline compounds (I-B) are as listed below, as well as their salts such as hydrochloride, acetate, or fumarate.

(1B) 4-[(2-Hydroxyethyl)oxy]-2-(1-piperazinyl)-quinazoline
(2B) 4-[(RS)-(2,3-Dihydroxypropyl)oxy]-2-(1-piperazinyl)quinazoline
(3B) 4-[(2RS,3SR)-(3-Hydroxybutan-2-yl)oxy]-2-(1-piperazinyl)quinazoline
(4B) 4-[(2S,3S)-(3-Hydroxybutan-2-yl)oxy]-2-(1-piperazinyl)quinazoline
(5B) 4-[(2R,3R)-(3-Hydroxybutan-2-yl)oxy]-2-(1-piperazinyl)quinazoline
(6B) 4-[(2RS,3RS)-(2,3-Dihydroxybutan-1-yl)oxy]-2-(1-piperazinyl)quinazoline
(7B) 4-[(2S,3S)-(2,3-Dihydroxybutan-1-yl)oxy]-2-(1-piperazinyl)quinazoline
(8B) 4-[(2R,3R)-(2,3-Dihydroxybutan-1-yl)oxy]-2-(1-piperazinyl)quinazoline
(9B) 4-[(3S)-(3,4-Dihydroxybutan-1-yl)oxy]-2-(1-piperazinyl)quinazoline
(10B) 4-[(3R)-(3,4-Dihydroxybutan-1-yl)oxy]-2-(1-piperazinyl)quinazoline
(11B) 4-[(2RS,3SR)-(2,3,4-Trihydroxybutan-1-yl)-oxy]-2-(1-piperazinyl)quinazoline
(12B) 4-[(2S,3S)-(2,3,4-Trihydroxybutan-1-yl)oxy]-2-(1-piperazinyl)quinazoline
(13B) 4-[(2R,3R)-(2,3,4-Trihydroxybutan-1-yl)oxy]-2-(1-piperazinyl)quinazoline
(14B) 4-[(2R)-(2,3-Dihydroxypropan-1-yl)oxy]-2-(1-piperazinyl)quinazoline Among the above quinazoline compounds (I-B), preferred ones are (10B) 4-[(3R)-(3,4-dihydroxybutan-1-yl) oxy]-2-(1-piperazinyl)quinazoline, (6B) 4-[(2RS,3RS)-(2,3-dihydroxybutan-1-yl)oxy]-2-(1-piperazinyl)quinazoline, (7B) 4-[(2S,3S)-(2,3-dihydroxybutan-1-yl)oxy]-2-(1-piperazinyl)quinazoline, (8B) 4-[(2R,3R)-(2,3-dihydroxybutan-1-yl)oxy]-2-(1-piperazinyl)quinazoline, and their salts such as hydrochloride, acetate, fumarate, particularly hydrochloride.

The quinazoline compounds of the present invention may be prepared by any one of the following Processes A to H.

Process A

Among the quinazoline compounds of the present invention, the quinazoline compounds (I-A) and pharmaceutically acceptable acid addition salts thereof can be prepared by Process A as shown in the following reaction scheme.

pound (IV) with a protecting group $R^2$ to give a compound (V), removing the protecting group $R^1$ of the compound (V) to give a compound (VI), and then removing the protecting group $R^2$ of the compound (VI) to give the desired compound (I-A), if desired, followed by converting it to a pharmaceutically acceptable acid addition salt by a conventional method.

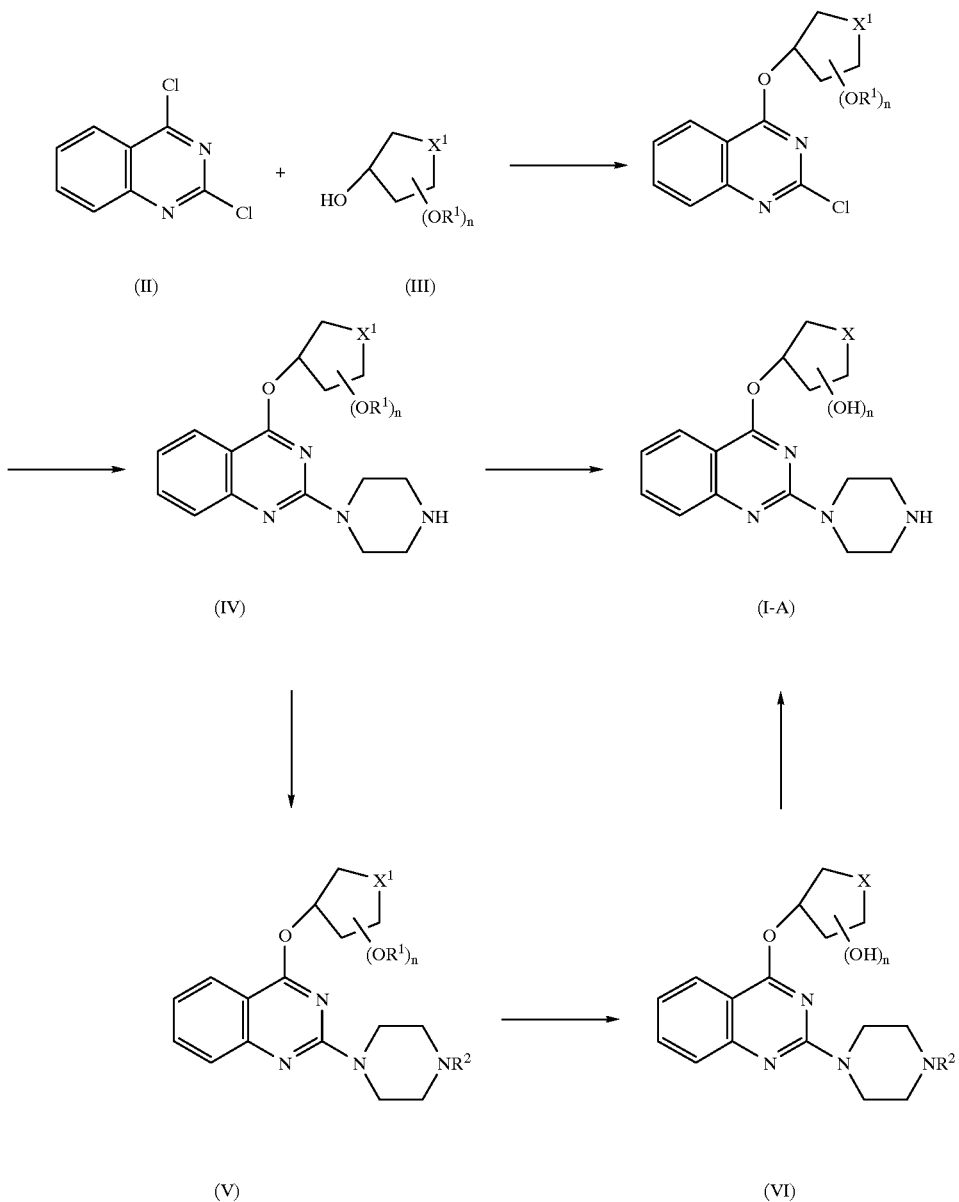

wherein $R^1$ is a protecting group for hydroxy group, $X^1$ is methylene, hydroxymethine protected by a protecting group $R^1$, methoxymethine, or oxygen atom, $R^2$ is a protecting group for piperazinyl group, and n and X are as defined above.

As is shown in the above reaction scheme, the quinazoline compounds (I-A) of the present invention can be prepared by reacting a compound (II) and a compound (III), reacting the resultant product with piperazine to give a compound (IV), and removing the protecting group $R^1$ from the compound (IV) to give the desired compound (I-A), or alternatively, protecting the piperazinyl group of the com- The protecting group $R^1$ used in the above reaction includes an acyl group (e.g. acetyl, benzoyl), a substituted alkyl group (e.g. methoxymethyl, benzyloxymethyl, tetrahydropyranyl), a silyl group (e.g. trimethylsilyl, t-butyldimethylsilyl), and the like. Besides, when there are two adjacent hydroxy groups to be protected by the protecting group $R^1$, those two hydroxy groups may be protected by isopropylidene ketal, cyclohexylidene ketal, or benzylidene acetal.

The protecting group $R^2$ for the piperazinyl group includes benzyloxycarbonyl, t-butoxycarbonyl, or 2,2,2-trichloroethoxycarbonyl.

The above Process A can be more specifically carried out as follows.

The compound (II) is reacted with 1 to 1.5 equivalent of the compound (III) in the presence of 1 to 1.5 equivalent of potassium t-butoxide in an inert organic solvent (e.g. dioxane, tetrahydrofuran, or dimethylformamide), at 0 to 50° C. for 30 minutes to 24 hours. After being briefly purified or without purification, the reaction product is reacted with piperazine [1 to 10 equivalents to the compound (II)] to give the compound (IV). The protecting group $R^1$ of the compound (IV) is removed by a conventional method to give the compound (I-A). For example, when the protecting group $R^1$ is acetyl, the compound (IV) is treated with 2 to 10 equivalents of potassium carbonate, sodium carbonate or sodium hydroxide in an alcohol (e.g. methanol, or ethanol) or a mixed solvent of water and a water-soluble solvent (e.g. acetone-water) at room temperature to 60° C. for 30 minutes to 24 hours, by which the protecting group $R^1$ can be removed. When the protecting group $R^1$ is tetrahydropyranyl or isopropylidene, the compound (IV) is treated in a 50–90% aqueous acetic acid solution at room temperature to 100° C. for 30 minutes to 48 hours, by which the protecting group $R^1$ can be removed.

According to the alternative route of the preparation of the compound (I-A) from the compound (IV) via the compound (V) and the compound (VI), the piperazinyl of the compound (IV) is firstly protected by a protecting group $R^2$ by a conventional method to give the compound (V). For example, when the protecting group $R^2$ is benzyloxycarbonyl, the compound (IV) is reacted with 1 to 2 equivalents of benzyl chlorocarbonate in the presence of 1 to 5 equivalents of a tertiary amine (e.g. triethylamine) in an inert organic solvent (e.g. toluene, dioxane, tetrahydrofuran, ethyl acetate, methylene chloride, dichloroethane) at 0 to 30° C. for 30 minutes to 24 hours to give the compound (V) (wherein $R^2$ is benzyloxycarbonyl). The protecting group for the hydroxy group of the compound (V) is removed in the same manner as in the deprotection of the compound (IV) as mentioned above to give the compound (VI). Finally, the protecting group $R^2$ for the piperazinyl group of the compound (VI) is removed by a conventional method to give the desired compound (I-A). For example, when the protecting group $R^2$ of the compound (VI) is benzyloxycarbonyl, the compound (VI) is subjected to hydrogenation in the presence of a hydrogenation catalyst in a solvent such as a lower alcohol (e.g. methanol, ethanol), acetic acid, dioxane, tetrahydrofuran, or a mixture thereof at a temperature of room temperature to a boiling point of the solvent under atmospheric pressure or under a pressure of 1 to 10 atm., by which the protecting group can be removed. The hydrogenation catalyst includes palladium/carbon, palladium hydroxide/carbon, or platinum oxide.

The compound (I-A) optionally may be purified to isolate a stereoisomer and/or an optically active isomer, and further optionally may be converted into a pharmaceutically acceptable acid addition salt by a conventional method.

Process B

Among the quinazoline compounds of the present invention, the quinazoline compounds of the following formula (I-Aa):

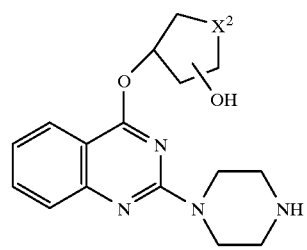

wherein $X^2$ is methylene, methoxymethine or an oxygen atom and pharmaceutically acceptable acid addition salts thereof can be prepared by Process B as shown in the following reaction scheme.

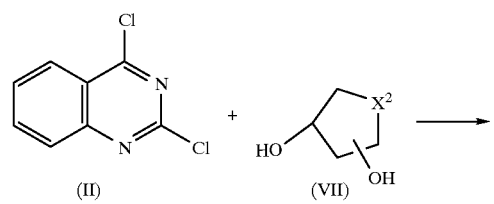

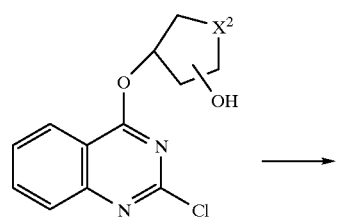

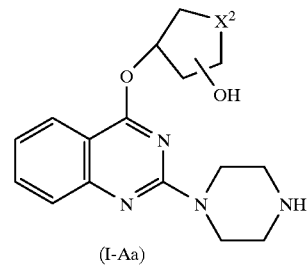

Wherein $X^2$ is as defined above.

As is shown in the above reaction scheme, the quinazoline compounds (I-Aa) of the present invention and their pharmaceutically acceptable acid addition salts can be prepared by reacting a compound (II) and a compound (VII), and reacting the resultant product with piperazine to give the desired compound (I-Aa), if desired, followed by converting it to a pharmaceutically acceptable acid addition salt by a conventional method.

The above Process B can be more specifically carried out as follows.

The compound (II) is reacted with 1 to 1.5 equivalent of the compound (VII) in the presence of 1 to 3 equivalents of sodium hydride in an inert organic solvent (e.g. dioxane, tetrahydrofuran, or dimethylformamide), at 0 to 80° C. for 30 minutes to 24 hours. After being briefly purified or without purification, the reaction product is reacted with piperazine [1 to 10 equivalents to the compound (II)] to give the compound (I-Aa).

The compound (I-Aa) optionally may be purified to isolate a stereoisomer and/or an optically active isomer, and further optionally may be converted into a pharmaceutically acceptable acid addition salt by a conventional method.

Process C

Among the quinazoline compounds of the present invention, the quinazoline compounds of the following formula (I-Ab):

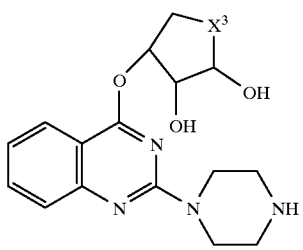

(I-Ab)

wherein $X^3$ is methylene, hydroxymethine or methoxymethine and pharmaceutically acceptable acid addition salts thereof can be prepared by Process C as shown in the following reaction scheme.

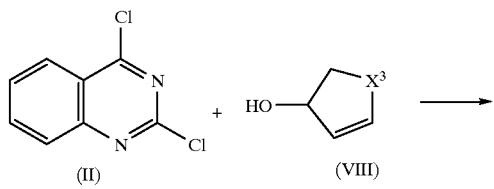

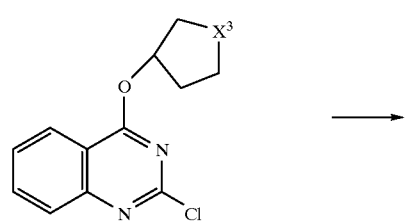

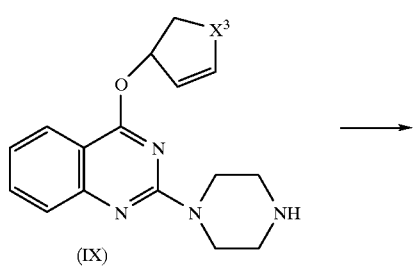

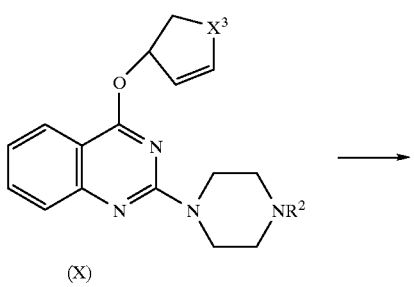

(X)

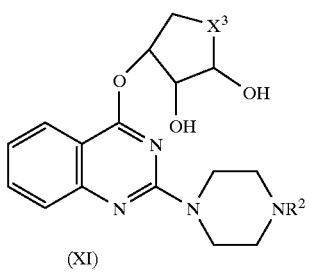

(XI)

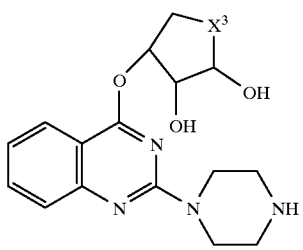

(I-Ab)

wherein $X^3$ and $R^2$ are as defined above.

As is shown in the above reaction scheme, the quinazoline compounds (I-Ab) of the present invention can be prepared by reacting a compound (II) and a compound (VIII), reacting the resultant product with piperazine to give a compound (IX), and protecting the piperazinyl group of the compound (IX) with a protecting group $R^2$ to give a compound (X), oxidizing the compound with osmium tetroxide to give a compound (XI), and then removing the protecting group $R^2$ to give the desired compound (I-Ab), if desired, followed by converting it to a pharmaceutically acceptable acid addition salt by a conventional method.

The protecting group $R^2$ for the piperazinyl group includes benzyloxycarbonyl, t-butoxycarbonyl, or 2,2,2-trichloroethoxycarbonyl as in the above Process A.

The above Process C can be more specifically carried out as follows.

In the same manner as described in the steps of preparing the compound (I-Aa) from the compound (II) and the compound (VII) in the above Process B, the compound (IX) is obtained from the compound (II) and the compound (VIII), and the piperazinyl of the compound (IX) is protected by a protecting group $R^2$ by a conventional method to give the compound (X). For example, when the protecting group $R^2$ is benzyloxycarbonyl, the piperazinyl of the compound (IX) is protected with benzyloxycarbonyl in the same manner as described in the step of converting the compound (IV) into the compound (V) in the above Process A.

After the above reaction, the compound (X) obtained above is oxidized with 0.001 to 0.1 equivalent of osmium tetroxide in the presence of 1 to 2 equivalents of 4-methylmorpholine N-oxide in a mixed solvent such as water-acetone or water-t-butanol at 0 to 40° C. for 1 to 72 hours to give the compound (XI). And then, the protecting group R² for the piperazinyl group of the compound (XI) is removed in the same manner as in the step of conversion of the compound (VI) into the compound (I-A) in the above Process A.

The compound (I-Ab) optionally may be purified to isolate a stereoisomer and/or an optically active isomer, and further optionally may be converted into a pharmaceutically acceptable acid addition salt by a conventional method.

Process D

Among the quinazoline compounds of the present invention, the quinazoline compounds of the following formula (I-Ac):

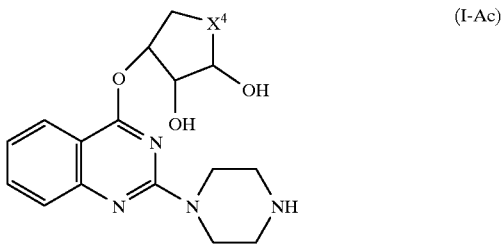

wherein X⁴ is hydroxymethine or methoxymethine, and pharmaceutically acceptable acid addition salts thereof can be prepared by Process D as shown in the following reaction scheme.

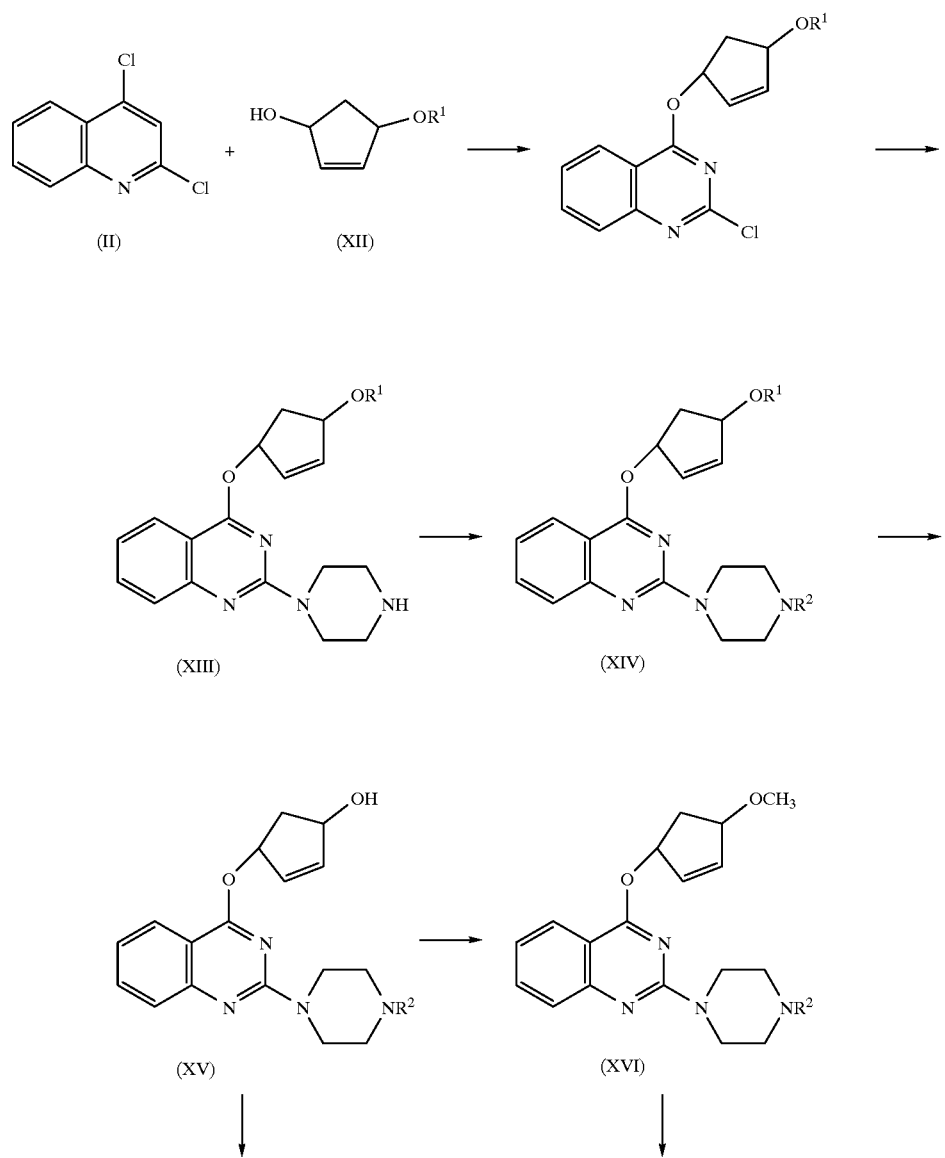

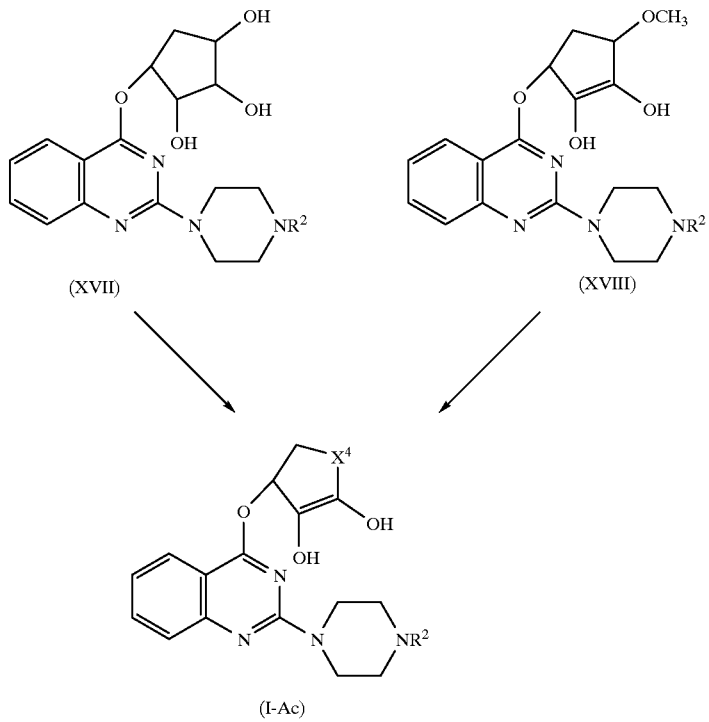

wherein $X^4$, $R^1$ and $R^2$ are as defined above.

As is shown in the above reaction scheme, a compound (II) is reacted with a compound (XII), and the resultant product is reacted with piperazine to give a compound (XIII), and the piperazinyl group of the compound (XIII) is protected with a protecting group $R^2$ to give a compound (XIV), and then the protecting group $R^1$ for the hydroxy group on the compound (XIV) is removed to give a compound (XV). A compound (XVI) may be prepared by methylating the hydroxy group of the compound (XV).

The compound (XV) or the compound (XVI) is oxidized with osmium tetroxide to give a compound (XVII) or a compound (XVIII), respectively, and then, the protecting group $R^2$ on the compound (XVII) or the compound (XVIII) is removed, and further, if desired, the resultant compound is converted into a pharmaceutically acceptable acid addition salt thereof by a conventional method, by which there is prepared the desired compound (I-Ac) or its pharmaceutically acceptable acid addition salt.

The protecting group $R^1$ for the hydroxy group used in the above reaction includes an acyl group (e.g. acetyl, benzoyl), a substituted alkyl group (e.g. methoxymethyl, benzyloxymethyl, tetrahydropyranyl), a silyl group (e.g. trimethylsilyl, t-butyldimethylsilyl), and the like. Besides, the protecting group $R^2$ for piperazinyl group includes benzyloxycarbonyl, t-butoxycarbonyl, or 2,2,2-trichloroethoxycarbonyl as in the above Process A.

The above Process D can be more specifically carried out as follows.

In the same manner as described in the steps of the preparation of the compound (IV) from the compound (II) and the compound (III) in the above Process A, the compound (XIII) is obtained from the compound (II) and the compound (XII), and the piperazinyl of the compound (XIII) is protected by a protecting group $R^2$ by a conventional method to give the compound (XIV). For example, when the protecting group $R^2$ is benzyloxycarbonyl, the piperazinyl of the compound (XIII) is protected with benzyloxycarbonyl in the same manner as described in the step of converting the compound (IV) into the compound (V) in the above Process A. From the compound (XIV) the protecting group $R^1$ is removed by a conventional method to give a compound (XV). For example, when the protecting group $R^1$ of the compound (XIV) is acetyl or tetrahydropyranyl, the protecting group $R^1$ is removed in the same manner as described in the step of converting the compound (IV) into the compound (I-A) in the above Process A.

The compound (XVI) is prepared by reacting the compound (XV) with 1 to 3 equivalents of methyl iodide in the presence of 1 to 2 equivalents of sodium hydride in an inert organic solvent (e.g. dioxane, tetrahydrofuran, dimethylformamide) at 0 to 50° C. for 30 minutes to 24 hours.

Thereafter, the compound (XV) or the compound (XVI) is oxidized with osmium tetroxide to give a compound (XVII) or a compound (XVIII) respectively in the same manner as described in the step of converting the compound (X) into the compound (XI) in the above Process C. And finally, the protecting group $R^2$ of the compound (XVII) or the compound (XVIII) is removed in the same manner as in the step of conversion of the compound (VI) into the compound (I-A) in the above Process A.

The compound (I-Ac) optionally may be purified to isolate a stereoisomer and/or an optically active isomer, and further optionally may be converted into a pharmaceutically acceptable acid addition salt by a conventional method.

In the above Processes A to D, the obtained quinazoline compound (I-A) of the present invention optionally may be purified by firstly protecting the piperazinyl group thereof by a conventional amino-protecting group (e.g. t-butoxycarbonyl), and purifying the product and then removing the protecting group (cf. Example 9 hereinafter).

The starting compound (II) used in the above Processes A to D may be prepared by a process as described in J. Am. Chem. Soc., 5, 3867 (1931); and the cyclic alcohol compounds (III), (VII), (VIII) and (XII) may be prepared by processes as described in Tetrahedron Asymmetry, 389 (1991), J. Org. Chem., 55, 4265 (1990), Org. Syn., 59, 169 (1979), Synthesis, 876 (1974), J. Org. Chem., 53, 1823 (1988), J. Chem., Soc., 248 (1959), Tetrahedron, 3155 (1990), J. Org. Chem., 38, 4122 (1973), J. Chem. Soc., Chem. Commun., 1298 (1986), Bull. Chem. Soc. Jpn., 63, 1402 (1990), J. Am. Chem. Soc., 110, 4726 (1988), Carbohydr. Res., 136, 285 (1985), J. Chem. Soc., 4026 (1952), or their analogous processes (cf. Reference Examples and Examples, described hereinafter).

Process E

Among the quinazoline compounds of the present invention, the quinazoline compounds (I-B) and pharmaceutically acceptable acid addition salts thereof can be prepared by Process E as shown in the following reaction scheme.

protecting the piperazinyl group of the compound (XX) with a protecting group $R^2$ to give a compound (XXI), removing the protecting group $R^1$ of the compound (XXI) to give a compound (XXII), and then removing the protecting group $R^2$ of the compound (XXII) to give the desired compound (I-B), if desired, followed by converting it to a pharmaceutically acceptable acid addition salt by a conventional method.

The protecting group $R^1$ used in the above reaction includes an acyl group (e.g. acetyl, benzoyl), a substituted alkyl group (e.g. methoxymethyl, benzyloxymethyl, tetrahydropyranyl), a silyl group (e.g. trimethylsilyl, t-butyldimethylsilyl), and the like. Besides, when there are adjacent two hydroxy groups to be protected by the protecting group $R^1$, those two hydroxy groups may be protected by isopropylidene ketal, cyclohexylidene ketal, or benzylidene acetal.

The protecting group $R^2$ for the piperazinyl group includes benzyloxycarbonyl, t-butoxycarbonyl, or 2,2,2-trichloroethoxycarbonyl.

The above Process E can be more specifically carried out as follows.

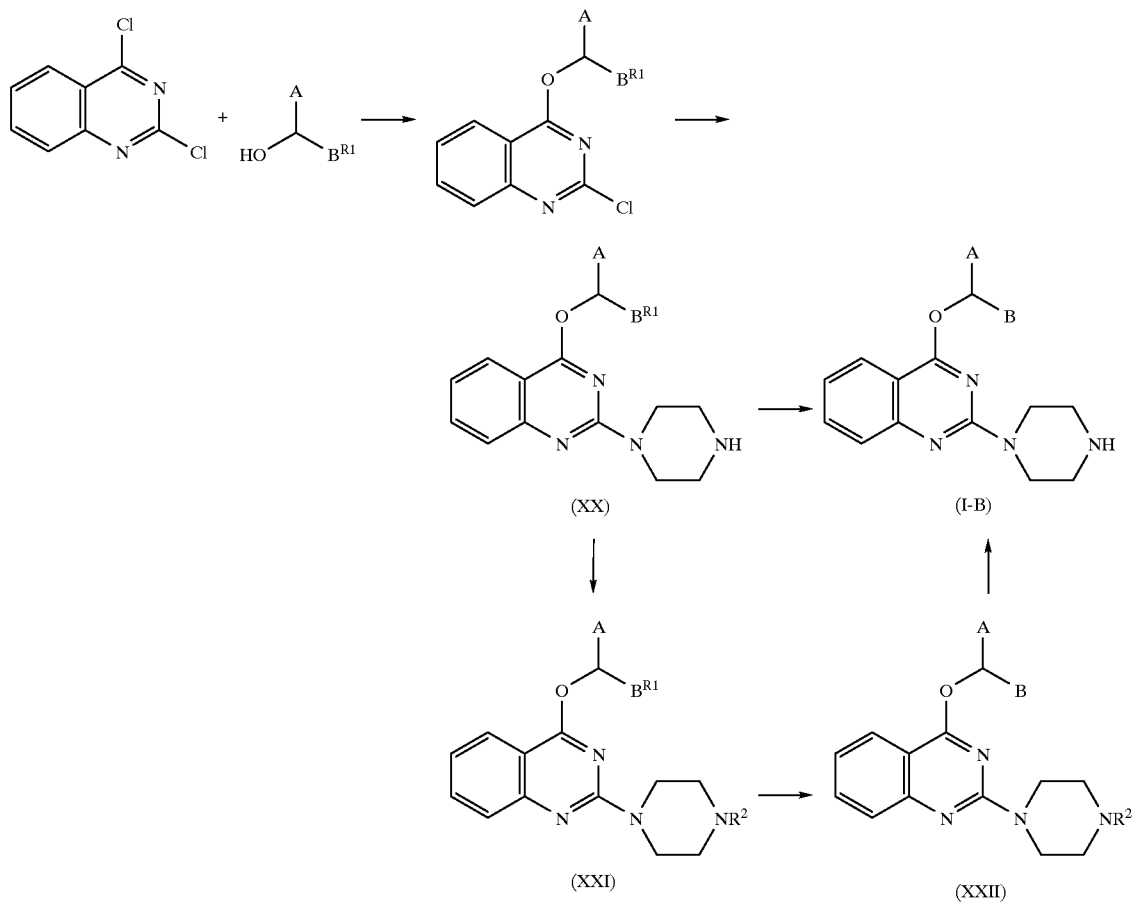

wherein $B^{R1}$ means that the hydroxy group of B is protected by a protecting group $R^1$, $R^2$ is a protecting group for piperazinyl group, and A and B are as defined above.

As is shown in the above reaction scheme, the quinazoline compounds (I-B) of the present invention can be prepared by reacting a compound (II) and a compound (XIX), reacting the resultant product with piperazine to give a compound (XX), removing the protecting group $R^1$ from the compound (XX) to give the desired compound (I-B), or alternatively, by The compound (II) is reacted with 1 to 1.5 equivalent of the compound (XIX) in the presence of 1 to 1.5 equivalent of potassium t-butoxide in an inert organic solvent (e.g. dioxane, tetrahydrofuran, or dimethylformamide), at 0 to 50° C. for 30 minutes to 24 hours. After being briefly purified or without purification, the reaction product is reacted with piperazine [1 to 10 equivalents to the compound (II)] to give the compound (XX). The protecting group $R^1$ of the compound (XX) is removed by a conventional method to give the compound (I-B). For example, when the protecting group $R^1$ is acetyl, the compound (XX) is treated with 2 to 10 equivalents of potassium carbonate, sodium carbonate or sodium hydroxide in an alcohol (e.g. methanol, or ethanol) or a mixed solvent of water and a water-soluble solvent (e.g. acetone-water) at room temperature to 80° C. for 30 minutes to 24 hours, by which the protecting group $R^1$ can be removed. When the protecting group $R^1$ of the compound (XX) is tetrahydropyranyl or isopropylidene, the compound (XX) is treated in a 50–90% aqueous acetic acid solution at room temperature to 100° C. for 30 minutes to 48 hours, by which the protecting group $R^1$ can be removed.

According to the alternative route of the preparation of the compound (I-B) from the compound (XX) via the compound (XXI) and the compound (XXII), the piperazinyl of the compound (XX) is firstly protected by a protecting group $R^2$ by a conventional method to give the compound (XXI). For example, when the protecting group $R^2$ is benzyloxycarbonyl, the compound (XX) is reacted with 1 to 2 equivalents of benzyl chlorocarbonate in the presence of 1 to 5 equivalents of a tertiary amine (e.g. triethylamine) in an inert organic solvent (e.g. toluene, dioxane, tetrahydrofuran, ethyl acetate, chloroform, methylene chloride, dichloroethane) at 0 to 30° C. for 30 minutes to 24 hours to give the compound (XXI) (wherein $R^2$ is benzyloxycarbonyl). The protecting group $R^1$ of the compound (XXI) is removed in the same manner as in the deprotection of the hydroxy group from the compound (XX) as mentioned above to give the compound (XXII). Finally, the protecting group $R^2$ for the piperazinyl group of the compound (XXII) is removed by a conventional method to give the desired compound (I-B). For example, when the protecting group $R^2$ of the compound (XXII) is benzyloxycarbonyl, the compound (XXII) is subjected to hydrogenation in the presence of a hydrogenation catalyst in a solvent such as a lower alcohol (e.g. methanol, ethanol), acetic acid, dioxane, tetrahydrofuran, or a mixture thereof at a temperature from room temperature to a boiling point of the solvent under atmospheric pressure or under a pressure of 1 to 10 atm., by which the protecting group can be removed. The hydrogenation catalyst includes palladium/carbon, palladium hydroxide/carbon, or platinum oxide.

The compound (I-B) optionally may be purified to isolate a stereoisomer and/or an optically active isomer, and further optionally may be converted into a pharmaceutically acceptable acid addition salt by a conventional method.

Process F

Among the quinazoline compounds of the present invention, the quinazoline compound of the following formula (I-Ba):

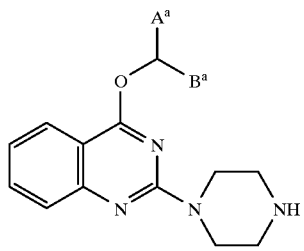

(I-Ba)

wherein $A^a$ is hydrogen atom, and $B^a$ is 1,2,3-trihydroxypropyl, and a pharmaceutically acceptable acid addition salt thereof can be prepared in a similar manner to Process E.

That is, the quinazoline compound (I-Ba) of the present invention and a pharmaceutically acceptable acid addition salt thereof can be prepared by reacting a compound (II) with 1 to 1.5 equivalent of threitol [$HOCH_2[CH(OH)]_2CH_2OH$] wherein two hydroxy groups at 2- and 3-positions are protected by isopropylidene ketal, cyclohexylidene ketal or benzylidene acetal, in the presence of 1 to 1.5 equivalent of sodium hydride in an inert organic solvent (e.g. dioxane, tetrahydrofuran, or dimethylformamide), at 0 to 50° C. for 30 minutes to 24 hours. After being briefly purified or without purification, the reaction product is reacted with piperazine [1 to 10 equivalents to the compound (II)], and then the protecting group of the resulting product is removed in the same manner as described in Process E.

The compound (I-Ba) may also be prepared by a similar manner to the steps of the conversion of the compound (XX) into the compound (I-B) through the compound (XXI) and the compound (XXII) in the above Process E (cf. Examples 62 and 64 hereinafter).

The compound (I-Ba) optionally may be purified to isolate a stereoisomer and/or an optically active isomer, and further optionally may be converted into a pharmaceutically acceptable acid addition salt by a conventional method.

Process G

Among the quinazoline compounds of the present invention, the quinazoline compounds of the formula (I-Bb):

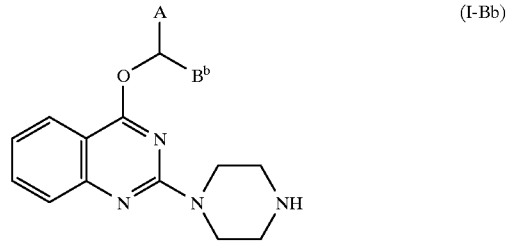

(I-Bb)

wherein $B^b$ is ethyl having two hydroxy substituents, or n-propyl having two or three hydroxy substituents, and A is as defined above, and pharmaceutically acceptable acid addition salts thereof can be prepared by Process G as shown in the following reaction scheme.

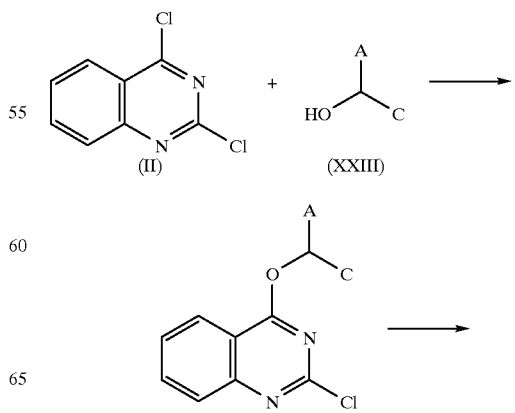

-continued

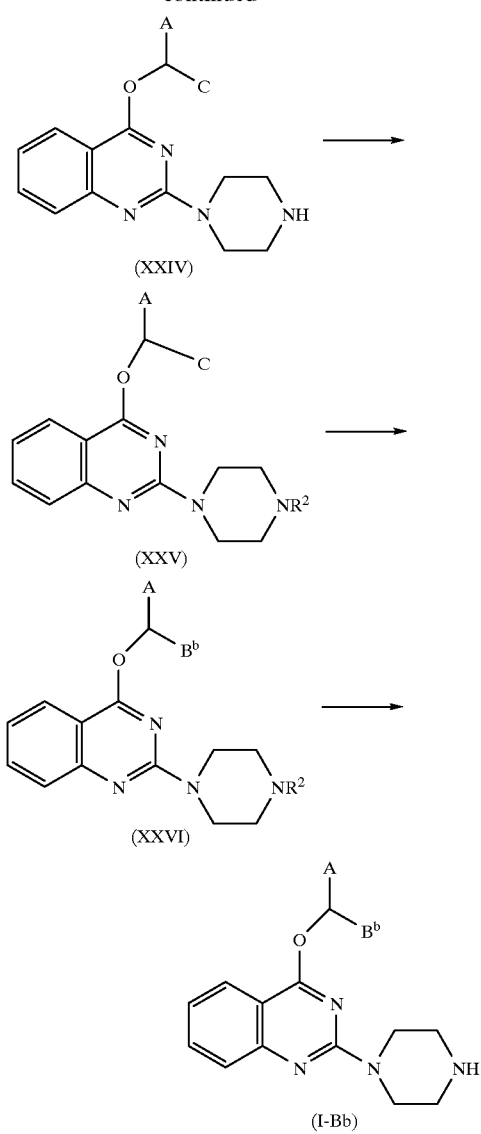

wherein C is vinyl, 1-propenyl, 3-hydroxy-1-propenyl, or allyl, and A, $B^b$ and $R^2$ are as defined above.

As is shown in the above reaction scheme, the quinazoline compounds (I-Bb) and their pharmaceutically acceptable acid addition salts of the present invention can be prepared by reacting a compound (II) and a compound (XXIII), reacting the resultant product with piperazine to give a compound (XXIV), and protecting the piperazinyl group of the compound (XXIV) with a protecting group $R^2$ to give a compound (XXV), oxidizing the compound (XXV) with an oxidizing agent such as osmium tetroxide to give a compound (XXVI), and then removing the protecting group $R^2$ of the compound (XXVI) to give the desired compound (I-Bb), if desired, followed by converting it to a pharmaceutically acceptable acid addition salt by a conventional method.

The protecting group $R^2$ for the piperazinyl group includes benzyloxycarbonyl, t-butoxycarbonyl, or 2,2,2-trichloroethoxycarbonyl as like as in the above Process E.

The above Process G can be more specifically carried out as follows.

The compound (II) is reacted with 1 to 1.5 equivalent of the compound (XXIII) in the presence of 1 to 3 equivalents of sodium hydride or 1 to 1.5 equivalent of potassium t-butoxide in an inert organic solvent (e.g. dioxane, tetrahydrofuran, or dimethylformamide), at 0 to 80° C. for 30 minutes to 24 hours. After being briefly purified or without purification, the reaction product is reacted with piperazine [1 to 10 equivalents to the compound (II)] to give the compound (XXIV). Then, the piperazinyl of the compound (XXIV) is protected by a protecting group $R^2$ by a conventional method to give the compound (XXV). For example, when the protecting group $R^2$ is benzyloxycarbonyl, the piperazinyl of the compound (XXIV) is protected with benzyloxycarbonyl in the same manner as described in the step of converting the compound (XX) into the compound (XXI) in the above Process E.

After the above reaction, the compound (XXV) is oxidized with 0.001 to 0.1 equivalent of osmium tetroxide in the presence of 1 to 2 equivalents of 4-methyl-morpholine N-oxide at 0 to 40° C. for 1 to 72 hours to give the compound (XXVI), or alternatively, the compound (XXV) is oxidized with 1 to 3 equivalents of an asymmetric osmium oxidizing agent (e.g. AD-mix-α or -β) [cf. Chem. Rev., 94, 2483 (1994)] in a mixed solvent such as water-acetone or water-t-butanol, and if necessary, in the presence of 1 to 1.5 equivalent of methanesulfonamide, at −10° C. to 20° C. for 10 to 96 hours to give the compound (XXVI). And finally, the protecting group $R^2$ for the piperazinyl group of the compound (XXVI) is removed in the same manner as in the step of conversion of the compound (XXII) into the compound (I-B) in the above Process E.

The compound (I-Bb) optionally may be purified to isolate a stereoisomer and/or an optically active isomer, and further optionally may be converted into a pharmaceutically acceptable acid addition salt by a conventional method.

Process H

Among the quinazoline compounds of the present invention, the quinazoline compounds of the following formula (I-Bc):

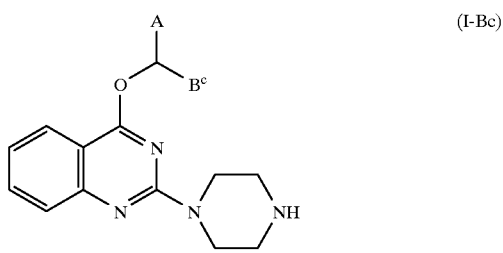

wherein $B^c$ is hydroxymethyl or 1-hydroxyethyl and A is as defined above, and pharmaceutically acceptable acid addition salts thereof can be prepared by Process H as shown in the following reaction scheme.

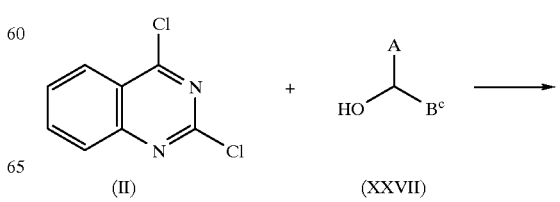

-continued

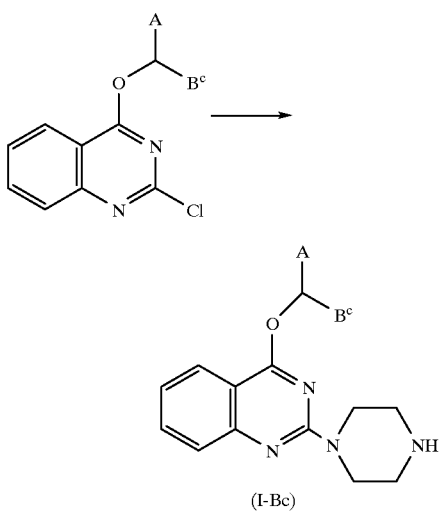

(I-Bc)

wherein A and $B^c$ are as defined above.

As is shown in the above reaction scheme, a compound (II) is reacted with a compound (XXVII), and the resultant product is reacted with piperazine to give the desired compound (I-Bc). Further, if desired, the resultant product is converted into a pharmaceutically acceptable acid addition salt by a conventional method, by which there is prepared the desired compound (I-Bc) or its pharmaceutically acceptable acid addition salt.

The above Process H can be more specifically carried out as follows.

The compound (II) is reacted with the compound (XXVII) in the presence of 1 to 3 equivalents of sodium hydride in an inert organic solvent (e.g. dioxane, tetrahydrofuran, or dimethylformamide) at 0 to 50° C. for 30 minutes to 24 hours. After being briefly purified or without purification, the reaction product is reacted with piperazine [1 to 10 equivalents to the compound (II)] to give the compound (I-Bc). The compound (I-Bc) optionally may be purified to isolate a stereoisomer and/or an optically active isomer, and further optionally may be converted into a pharmaceutically acceptable acid addition salt by a conventional method.

The quinazoline compounds of the present invention may be used as an anti-tumor agent in the form of a conventional pharmaceutical preparation for an oral or parenteral administration.

The preparation for oral administration includes solid preparations such as tablets, granules, powders, capsules, and liquid preparations such as syrups. These preparations can be prepared by a conventional method. The solid preparations can be prepared by using conventional pharmaceutical carriers, such as lactose, starch, crystalline cellulose, calcium carboxymethylcellulose, talc, magnesium stearate, etc. Capsules can be prepared by capsulating the granules or powders thus prepared. Syrups can be prepared by dissolving or suspending the quinazoline compound in an aqueous solution containing sucrose, carboxymethylcellulose, etc.

The preparation for parenteral administration includes injections. The injection preparation can also be prepared by a conventional method, and optionally may be incorporate isotonic agents (e.g. mannitol, sodium chloride, glucose, sorbitol, glycerol, xylitol, fructose, maltose, mannose), stabilizers (e.g. sodium sulfite, albumin), preservatives (e.g. benzyl alcohol, methyl p-hydroxybenzoate).

The quinazoline compounds of the present invention are effective for the treatment of solid tumors such as gastric cancer, colon cancer and breast cancer, by inhibiting the flow of blood into the tumor tissues, wherein blood is necessary for growth of the solid tumors.

The dose of the quinazoline compound may vary according to the severity of the diseases, ages and body surface area of the patients and the like, but is usually in the range of 1 to 1000 mg/m$^2$ (body surface area) per day in an adult, which may be administered once or by dividing into two or three times by the oral or parenteral route.

The following experiments illustrate the inhibitory effects of the compounds of the present invention on the flow of blood into a tumor tissue which is essential for growth of a solid tumor (Experiment 1), and the anti-tumor activity which would be assumed owing to the above blood flow-inhibitory effects (anti-tumor activity against human gastric cancer St-4 transplanted into nude mouse) (Experiment 2). Besides, the compounds of the present invention do not show undesirable hemolytic activity (Experiment 3) and have less side effects on central nervous system, i.e. low toxicity.

Thus, the anti-tumor agent containing the compound of the present invention is a new type of anti-tumor agent different from the known anti-tumor agents which attack the cancer cells directly.

Experiment 1

Inhibitory activity of dye accumulation in the solid tumor tissue (inhibition of the tumor blood flow):

a) Materials:
  Test Animal: Male BALB/c mice (weighing 21–27 g, six mice per group)
  Tumor: Colon 26 solid tumor
  Test Compounds:

(1) 4-[trans-(2-Hydroxycyclopentan-1-yl)oxy]-2-(1-piperazinyl)quinazoline monoacetate (Compound AA of this invention)

(2) 4-[cis-(2-Hydroxycyclopentan-1-yl)oxy]-2-(1-piperazinyl)quinazoline monoacetate (Compound AB of this invention)

(3) 4-[(3-Hydroxycyclopentan-1-yl)oxy]-2-(1-piperazinyl)quinazoline monoacetate (Compound AC of this invention)

(4) 4-[(1S,2S)-(2-Hydroxycyclopentan-1-yl)oxy]-2-(1-piperazinyl)quinazoline monoacetate (Compound AD of this invention)

(5) 4-[(1R,2R)-(2-Hydroxycyclopentan-1-yl)oxy]-2-(1-piperazinyl)quinazoline monoacetate (Compound AE of this invention)

(6) 4-[trans-(4-Hydroxytetrahydrofuran-3-yl)oxy]-2-(1-piperazinyl)quinazoline monoacetate (Compound AF of this invention)

(7) 4-[cis-(4-Hydroxytetrahydrofuran-3-yl)oxy]-2-(1-piperazinyl)quinazoline monoacetate (Compound AG of this invention)

(8) 4-[(3S,4S)-(4-Hydroxytetrahydrofuran-3-yl)oxy]-2-(1-piperazinyl)quinazoline monoacetate (Compound AH of this invention)

(9) 4-[(3R,4R)-(4-Hydroxytetrahydrofuran-3-yl)oxy]-2-(1-piperazinyl)quinazoline monoacetate (Compound AI of this invention)

(10) 4-[(3R,4R)-(4-Hydroxytetrahydrofuran-3-yl)-oxy]-2-(1-piperazinyl)quinazoline ½ hydrochloride (Compound AJ of this invention)

(11) 4-[(3R,4R)-(4-Hydroxytetrahydrofuran-3-yl)-oxy]-2-(1-piperazinyl)quinazoline monohydrochloride (Compound AK of this invention)

(12) 4-[(t-2,t-3-Dihydroxycyclopentan-r-1-yl) oxy]-2-(1-piperazinyl)quinazoline monoacetate (Compound AL of this invention)
(13) 4-[(t-3,t-4-Dihydroxycyclopentan-r-1-yl)oxy]-2-(1-piperazinyl)quinazoline monohydrochloride (Compound AM of this invention)
(14) 4-[(c-3,c-4-Dihydroxycyclopentan-r-1-yl)oxy]-2-(1-piperazinyl)quinazoline monohydrochloride (Compound AN of this invention)
(15) 4-[(t-2,t-3,c-4-Trihydroxycyclopentan-r-1-yl)-oxy]-2-(1-piperazinyl)quinazoline ½ fumarate (Compound AO of this invention)
(16) 4-[(1S,2S,3S,4R)-(2,3,4-Trihydroxycyclopentan-1-yl) oxy]-2-(1-piperazinyl)quinazoline ½ fumarate (Compound AP of this invention)
(17) 4-[(1R,2R,3R,4S)-(2,3,4-Trihydroxycyclopentan-1-yl) oxy]-2-(1-piperazinyl)quinazoline ½ fumarate (Compound AQ of this invention)
(18) 4-[(1S,2S,3R,4R)-(2,3-Dihydroxy-4-methoxy-cyclopentan-1-yl)oxy]-2-(1-piperazinyl)quinazoline ½ fumarate (Compound AR of this invention)
(19) 4-[(1R,2R,3S,4S)-(2,3-Dihydroxy-4-methoxy-cyclopentan-1-yl)oxy]-2-(1-piperazinyl)quinazoline ½ fumarate (Compound AS of this invention)
(20) 4-[(1R,2R,3S,4S)-(2,3-Dihydroxy-4-methoxy-cyclopentan-1-yl)oxy]-2-(1-piperazinyl)quinazoline mono-hydrochloride (Compound AT of this invention)
(21) 4-[(2-Hydroxyethyl)oxy]-2-(1-piperazinyl)-quinazoline monoacetate (Compound BA of this invention)
(22) 4-[(RS)-(2,3-Dihydroxypropyl)oxy]-2-(1-piperazinyl) quinazoline monoacetate (Compound BB of this invention)
(23) 4-[(2RS,3SR)-(3-Hydroxybutan-2-yl)oxy]-2-(1-piperazinyl)quinazoline monoacetate (Compound BC of this invention)
(24) 4-[(2S,3S)-(3-Hydroxybutan-2-yl) oxy]-2-(1-piperazinyl)quinazoline monoacetate (Compound BD of this invention)
(25) 4-[(2R,3R)-(3-Hydroxybutan-2-yl) oxy]-2-(1-piperazinyl)quinazoline monoacetate (Compound BE of this invention)
(26) 4-[(2RS,3RS)-(2,3-Dihydroxybutan-1-yl)oxy]-2-(1-piperazinyl)quinazoline (Compound BF of this invention)
(27) 4-[(2S,3S)-(2,3-Dihydroxybutan-1-yl)oxy]-2-(1-piperazinyl)quinazoline monohydrochloride (Compound BG of this invention)
(28) 4-[(2R,3R)-(2,3-Dihydroxybutan-1-yl)oxy]-2-(1-piperazinyl)quinazoline monohydrochloride (Compound BH of this invention)
(29) 4-[(3S)-(3,4-Dihydroxybutan-1-yl)oxy]-2-(1-piperazinyl)quinazoline monohydrochloride (Compound BI of this invention)
(30) 4-[(3R)-(3,4-Dihydroxybutan-1-yl)oxy]-2-(1-piperazinyl)quinazoline monohydrochloride (Compound BJ of this invention)
(31) 4-[(2RS,3SR)-(2,3,4-Trihydroxybutan-1-yl) oxy]-2-(1-piperazinyl)quinazoline (Compound BK of this invention)
(32) 4-[(2S,3S)-(2,3,4-Trihydroxybutan-1-yl)oxy]-2-(1-piperazinyl)quinazoline monohydrochloride (Compound BL of this invention)
(33) 4-[(2R,3R)-(2,3,4-Trihydroxybutan-1-yl) oxy]-2-(1-piperazinyl)quinazoline monohydrochloride (Compound BM of this invention)
(34) 4-[(2R)-(2,3-Dihydroxypropan-1-yl)oxy]-2-(1-piperazinyl)quinazoline (Compound BN of this invention)
(35) 2-(4-Allylpiperazin-1-yl)-4-[(1-pentyl) oxy]-quinazoline monofumarate (No. 5666, Reference compound)

b) Test Method:

Colon 26 solid tumor was cut in a size of about 1 mm square. The pieces of solid tumor were treated with a 0.25% collagenase solution and 0.02% deoxyribonuclease solution at 37° C. for 1.5 hour to give a cell suspension of colon 26 solid tumor cells. The cell suspension was adjusted to $3\times10^6$ cells/ml and the cell suspension (100 μl) was subcutaneously inoculated on the right back of male BALB/c mice. Ten days after the transplantation, the longitudinal size of the tumor was measured, and when the longitudinal size of the tumor reached about 10 mm, the mice were randomized. To the mice in test groups, the test compound was intravenously administered in an amount of 10 mg/kg or 1.25 mg/kg. The test compound was administered in the form of a solution in saline (in the test solution of Test Compound BF and BK, an equimolar amount of fumaric acid was further added, and in the test solution of Test Compound BN, an equimolar amount of hydrochloric acid was further added). To the mice in the control group, only saline was administered intravenously.

One hour after the administration, 3% Evans blue-saline solution was injected intravenously via the tail vein of the mice in a volume of 0.1 ml per 10 g of the body weight of mouse, and 5 minutes later the mice were killed by luxation of the cervical vertebrae.

After removing the tumor, the tumor was weighed. To extract Evans blue, the tumor was suspensed in 0.5% aqueous sodium sulfate (1.5 ml per 1 g of the tumor) and acetone (3.5 ml per 1 g of tumor), and then the tumor was cut into small pieces. After allowing to stand at room temperature overnight, the suspension were centrifuged at 3,000 rpm for 10 minutes to extract Evans blue, and the absorbance of the supernatant was read at 630 nm.

The inhibitory activity of dye accumulation into the solid tumor was evaluated as follows:

(+): The average absorbance in the test group is significantly smaller than the average absorbance in the control group.

(−): There is no significant difference in the average absorbance between the test group and the control group.

c) Test Results:

The above test results are shown in Table 1.

TABLE 1

| Test Compounds | Inhibitory activity of dye accumulation into solid tumor | |
| --- | --- | --- |
|  | 10 mg/kg | 1.25 mg/kg |
| Test Compound AA | + | + |
| Test Compound AB | + | − |
| Test Compound AC | + | + |
| Test Compound AD | + | + |
| Test Compound AE | + | + |
| Test Compound AF | + | + |
| Test Compound AG | + | + |
| Test Compound AH | + | + |
| Test Compound AI | + | + |

TABLE 1-continued

| Test Compounds | Inhibitory activity of dye accumulation into solid tumor | |
|---|---|---|
|  | 10 mg/kg | 1.25 mg/kg |
| Test Compound AJ | + | + |
| Test Compound AK | + | + |
| Test Compound AL | + | + |
| Test Compound AM | + | + |
| Test Compound AN | + | + |
| Test Compound AO | + | + |
| Test Compound AP | + | + |
| Test Compound AQ | + | + |
| Test Compound AR | + | + |
| Test Compound AS | + | + |
| Test Compound AT | + | + |
| Test Compound BA | + | + |
| Test Compound BB | + | + |
| Test Compound BC | + | + |
| Test Compound BD | + | N.D.* |
| Test Compound BE | + | N.D. |
| Test Compound BF | + | + |
| Test Compound BG | + | + |
| Test Compound BH | + | + |
| Test Compound BI | + | + |
| Test Compound BJ | + | + |
| Test Compound BK | + | + |
| Test Compound BL | + | + |
| Test Compound BM | + | + |
| Test Compound BN | N.D. | + |
| No. 5666 | + | − |

*N.D. means "Not Determined".

As is shown in Table 1, the compounds of this invention inhibited significantly the flow of blood into the tumor tissue which is essential for growth of the tumor, and the inhibitory activity of the compounds of this invention was similar to or more than the activity of the reference compound (No. 5666).

Experiment 2

Anti-tumor activity against human gastric cancer St-4 (solid tumor) transplanted to nude mouse:

a) Materials:
   Test Animal: Male BALB/cA JCI-nu nude mice (six week old, six mice per group)
   Tumor: St-4 solid tumor (human gastric cancer transplantable to nude mouse)
   Test Compounds:

(1) 4-[(t-3,t-4-Dihydroxycyclopentan-r-1-yl)oxy]-2-(1-piperazinyl)quinazoline monohydrochloride (Compound AM of this invention)
(2) 4-[(3R,4R)-(4-Hydroxytetrahydrofuran-3-yl)oxy]-2-(1-piperazinyl)quinazoline monoacetate (Compound AI of this invention)
(3) 4-[(3R)-(3,4-Dihydroxybutan-1-yl)oxy]-2-(1-piperazinyl)quinazoline monohydrochloride (Compound BJ of this invention)
(4) 2-(4-Allylpiperazin-1-yl)-4-[(1-pentyl) oxy]-quinazoline monofumarate (No. 5666, Reference compound)

b) Test Method:
   St-4 solid tumor was cut to about 3 mm cubic, and the fragments were subcutaneously transplanted into the back at one side of the nude mice with a trockar. Ten days after the transplantation, the longitudinal size (L) and the size of the width direction (W) of the tumor were measured. The tumor weight was calculated by the formula: L×W×W/2, and when the weight of the tumor reached 100 mg to 300 mg, the mice were randomized. To the mice in test groups, the test compound was orally administered once a day for 40 days. The test compounds of this invention were administered in an amount of 30 mg/kg or 40 mg/kg in the form of a solution in distilled water, and No. 5666 was administered in an amount of 30 mg/kg or 100 mg/kg in the form of a suspension in 5% arabic gum solution.

After the administration of the test compounds, the longitudinal size and the size in the width direction of the tumor were measured, and then the weight of tumor was calculated. The ratio of the tumor weight after treated with test compounds to the tumor weight before administration of test compounds (i.e. the relative tumor weight) was determined. As to the control group, the relative tumor weight was also determined likewise.

The anti-tumor activity was evaluated in the same manner as described in Ann. Clin. Lab. Sci., 8 (1), 50 (1978). That is, the ratio of the relative tumor weight in the test group (T) to that in the control group (C) [T/C (%)] was calculated, and when the minimum of the ratio [Min. T/C (%)] was less than 42%, the test compound was evaluated as "effective".

c) Test Results:
   The above test results are shown in Table 2.

TABLE 2

| Test Compounds | Dose (× days) | Min. T/C (%) | Evaluation |
|---|---|---|---|
| Test Compd. AM | 30 mg/kg (po) (× 40) | 36.1 | Effective |
| Test Compd. AI | 40 mg/kg (po) (× 40) | 31.7 | Effective |
|  | 30 mg/kg (po) (× 40) |  |  |
| Test Compd. BJ |  | 38.8 | Effective |
| No. 5666 | 30 mg/kg (po) (× 40) | 59.7 | Non-effective |
|  | 100 mg/kg (po) (") | 29.9 | Effective |

Experiment 3

Hemolytic activity:

a) Materials:
   Test Animal: Male Donryu rats
   Test Compounds: The same as in Experiment 1 b) Test Method:
   Blood (about 6 ml or more) was collected from abdominal large vein of male Donryu rats, which was taken in a test tube containing dipotassium ethylenediamine tetraacetate (10 mg). The blood thus collected was divided into each 2 ml, which was centrifuged at 3,000 rpm for 5 minutes. After removing the supernatant, a 150 mM phosphate buffer (pH 7.4) (10 ml) was added thereto, and the mixture was mildly mixed. The mixture was centrifuged at 3,000 rpm for 5 minutes, followed by washing with the same phosphate buffer as above. This procedure was repeated twice. Finally, the same phosphate buffer was added thereto to prepare a test blood cell suspension.

The test compound was dissolved in a saline solution in a concentration of 2 mg/ml in case of No. 5666, and of 20 mg/ml in case of the test compounds of this invention. (As to Test Compound BF, BK and BN, these were dissolved in dimethylsulfoxide instead of a saline solution in a concentration of 20 mg/ml). Just before subjecting to the hemolytic test, the above solutions were each diluted with the phosphate buffer so as to be a total of 2.7 ml and then added thereto the test blood cell suspension (0.3 ml) and thereby the test solution was made to be a total of 3.0 ml wherein the test compound was contained in a final concentration of 20 μg/ml (as to No. 5666) and of 200 μg/ml (as to the test compounds of this invention). Immediately, the mixture was gently mixed and incubated at 37° C. for 60 minutes.

Immediately after the incubation, the mixture was centrifuged at 3,000 rpm for 5 minutes, and the supernatant (each 200 μl) was added to a well of a 96 well microplate (an immunoassay plate with plane bottom), and the absorbance (OD: optical density) was read with a microplate reader (at a wavelength of 550 nm).

In a negative control (spontaneous hemolysis), only saline was added to the phosphate buffer, and in the positive control (complete hemolysis), a mixture of distilled water (2.7 ml) and the test blood cell suspension (0.3 ml) was added.

The hemolytic rate was calculated by the following equation:

$$\text{Hemolytic ratio (\%)} = \frac{(\text{OD of Test Soln.}) - (\text{OD of Neg. Cont.})}{(\text{OD of Pos. Cont.}) - (\text{OD of Neg. Cont.})} \times 100$$

In the above equation, "Test Soln." means a solution wherein the test compound was added, "Neg. Cont." means a solution of negative control, and "Pos. Cont." means a solution of positive control.

c) Test Results:

The reference compound No. 5666 induced hemolytic activity in a concentration of 20 μg/ml (the hemolytic ratio: 38%), but on the other hand, all of the Test Compounds AA to BN of the present invention did not show any hemolytic activity in a concentration of 200 μg/ml (the hemolytic ratio: 0–3%).

Experiment 4

Acute toxicity:

a) Materials:
Test Animal: Male ddY mice (5 week old, five mice per group)
Test Compounds:

(1) 4-[(t-3,t-4-Dihydroxycyclopentan-r-1-yl)oxy]-2-(1-piperazinyl)quinazoline monohydrochloride (Compound AM of this invention)
(2) 4-[(3R)-(3,4-Dihydroxybutan-1-yl)oxy]-2-(1-piperazinyl)quinazoline monohydrochloride (Compound BJ of this invention)

b) Test Method:
To male ddY mice was administered a solution of a test compound in saline intravenously, or a solution of a test compound in distilled water orally. One week after the administration, the number of death of mice was counted, and the $LD_{50}$ was calculated therefrom by a probit method.

c) Test Results:
The above test results are shown in Table 3.

TABLE 3

|  | $LD_{50}$ (mg/kg) | |
| --- | --- | --- |
| Test compounds | Intravenous injection | Oral administration |
| Test Compound AM | 101 | >500 |
| Test Compound BJ | 118 | >1000 |

EXAMPLES

The present invention is illustrated by the following Examples and Reference Examples but should not be construed to be limited thereto.

Reference Example 1

4-Benzyloxycyclopent-1-ene:

To a solution of cyclopent-3-en-1-ol [cf. J. Org. Chem., 32, 4138 (1967)] (7.00 g) and benzyl bromide (10.5 ml) in dimethylformamide (35 ml) is added gradually 60% sodium hydride (in oil) (3.68 g) with stirring under ice-cooling, and the mixture is stirred at room temperature for 1.5 hour. The reaction mixture is diluted with ethyl acetate and washed with water six times. The ethyl acetate solution thus obtained is dried over anhydrous magnesium sulfate, evaporated to dryness under reduced pressure, and then purified by medium pressure liquid column chromatography (eluent; n-hexane, n-hexane:ethyl acetate—50:1, v/v) to give 4-benzyloxycyclopent-1-ene (11.22 g) as an oily substance.

NMR (60 MHz, CDCl$_3$, δppm): 2.4–2.7 (4H, m), 4.29 (1H, m), 4.46 (2H, s), 5.65 (2H, s), 7.26 (5H, s)

Reference Example 2 c-4-Benzyloxycyclopentane-r-1,c-2-diol and t-4-benzyloxycyclopentane-r-1,c-2-diol:

A mixture of 4-benzyloxycyclopent-1-ene (cf. Reference Example 1) (3.85 g), a solution of osmium tetraoxide in t-butanol (osmium tetroxide 106 mg/t-butanol 8.36 g) (1.10 g) and 4-methylmorpholine N-oxide (2.72 g) in water (20 ml)-acetone (50 ml) is stirred at room temperature for 15 hours. Acetone is distilled off from the reaction mixture under reduced pressure, and thereto is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=100:1, v/v), and there are obtained c-4-benzyloxycyclopentane-r-1,c-2-diol (1.50 g) as crystals from the first fraction, and further t-4-benzyloxycyclopentane-r-1,c-2-diol (1.50 g) as crystals from the latter fraction.

c-4-Benzyloxycyclopentane-r-1,c-2-diol:
NMR (300 MHz, CDCl$_3$, δppm): 1.9–2.2 (4H, m), 2.89 (2H, br), 3.9–4.1 (3H, m), 4.49 (2H, s), 7.2–7.4 (5H, m)

t-4-Benzyloxycyclopentane-r-1,c-2-diol:
NMR (300 MHz, CDCl$_3$, δppm): 2.02 (4H, m), 2.37 (2H, br), 4.19 (1H, m), 4.25 (2H, br), 4.44 (2H, s), 7.2–7.4 (5H, m)

Reference Example 3 r-1,c-2-Diacetoxy-t-4-benzyloxycyclopentane:

To a solution of t-4-benzyloxycyclopentane-r-1,c-2-diol (cf. Reference Example 2) (1.20 g) in pyridine (6 ml) is added acetic anhydride (2.2 ml) with stirring under ice-cooling, and the mixture is stirred at room temperature for 18 hours. The reaction mixture is diluted with ethyl acetate, and the mixture is washed with diluted hydrochloric acid and water. The ethyl acetate solution is dried over anhydrous magnesium sulfate and evaporated to dryness under reduced pressure to give r-1,c-2-diacetoxy-t-4-benzyloxycyclopentane (1.83 g) as crystals.

NMR (300 MHz, CDCl$_3$, δppm): 2.03 (6H, s), 2.0–2.2 (4H, m), 4.20 (1H, m), 4.46 (2H, s), 5.36 (2H, m), 7.2–7.4 (5H, m)

Reference Example 4 t-3,t-4-Diacetoxycyclopentan-r-1-ol:

To a solution of r-1,c-2-diacetoxy-t-4-benzyloxycyclopentane (cf. Reference Example 3) (1.83 g) in ethanol (40 ml) is added 10% palladium/carbon (300 mg), and the mixture is stirred under hydrogen atmosphere and under a pressure of 5 atm. at room temperature for 6 hours. The reaction mixture is filtered and the filtrate is evaporated to dryness under reduced pressure to give t-3,t-4-diacetoxycyclopentan-r-1-ol (1.13 g) as crystals.

NMR (300 MHz, CDCl$_3$, δppm): 2.04 (6H, s), 1.9–2.2 (5H, m), 4.54 (1H, m), 5.38 (2H, m)

Reference Example 5

1,2-O-Isopropylidene-c-4-benzyloxycyclopentane-r-1,c-2-diol:

To a solution of c-4-benzyloxycyclopentane-r-1,c-2-diol (cf. Reference Example 2) (10.45 g) and 2,2-dimethoxypropane (24.5 ml) in dry methylene chloride (144 ml) is added p-toluenesulfonic acid monohydrate (25 mg), and the mixture is stirred at room temperature for 2.5 hours. The reaction mixture is diluted with chloroform, and the mixture is washed with aqueous sodium hydrogen carbonate solution and water. The resulting solution is dried over anhydrous magnesium sulfate and evaporated to dryness under reduced pressure to give 1,2-O-isopropylidene-c-4-benzyloxycyclopentane-r-1,c-2-diol (11.28 g) as oil.

NMR (300 MHz, CDCl$_3$, δppm): 1.30 (3H, s), 1.47 (3H, s), 1.7–1.9 (2H, m), 2.1–2.3 (2H, m), 4.00 (1H, m), 4.50 (2H, s), 4.67 (2H, m), 7.2–7.4 (5H, m)

Reference Example 6

1,2-O-Isopropylidene-r-1,c-2,c-4-cyclopentanetriol:

To a solution of 1,2-O-isopropylidene-c-4-benzyloxycyclopentane-r-1,c-2-diol (cf. Reference Example 5) (11.00 g) in ethanol (230 ml) is added 10% palladium/carbon (1.73 g), and the mixture is stirred under hydrogen atmosphere and under a pressure of 6 atm. at room temperature for 24 hours. The reaction mixture is filtered and the filtrate is evaporated to dryness under reduced pressure to give 1,2-O-isopropylidene-r-1,c-2,c-4-cyclopentanetriol (6.63 g) as oil.

NMR (300 MHz, CDCl$_3$, δppm): 1.33 (3H, s), 1.51 (3H, s), 1.7–1.9 (2H, m), 2.1–2.3 (2H, m), 2.61 (1H, d, J=9.5 Hz), 4.2–4.3 (1H, br), 4.75 (2H, m)

Example 1

4-[trans-(2-Hydroxycyclopentan-1-yl)oxy]-2-(1-piperazinyl)quinazoline:

To a solution of trans-1,2-cyclopentanediol [manufactured by Aldrich Co., cf. J. Chem. Soc., 4026 (1952)] (5.39 g) and 2,4-dichloroquinazoline [cf. J. Am. Chem. Soc., 53, 3867 (1931)] (9.58 g) in dimethylformamide (50 ml) is added gradually 60% sodium hydride (in oil) (2.49 g) with stirring under ice-cooling, and the mixture is stirred at room temperature for 1 hour and 20 minutes. The reaction mixture is diluted with ethyl acetate and washed with water 6 times. The resulting ethyl acetate solution is dried over anhydrous magnesium sulfate and is evaporated to dryness under reduced pressure, and the residue is briefly purified with medium pressure liquid column chromatography (eluent, chloroform) to give an oily substance. The oily substance thus obtained is dissolved in dioxane (27 ml), and the mixture is slowly added dropwise to a solution of piperazine (9.67 g) in dioxane (36 ml) with stirring at 70° C., and the mixture is stirred at the same temperature for one hour and 10 minutes. The reaction mixture is diluted with ethyl acetate, washed with water, and dried over anhydrous magnesium sulfate. The resulting solution is evaporated to dryness under reduced pressure, and the residue is washed with acetone, and the resulting crystals are recrystallized from acetone to give 4-[trans-(2-hydroxycyclopentan-1-yl)oxy]-2-(1-piperazinyl)quinazoline (2.89 g) as crystals.

NMR (300 MHz, CDCl$_3$, δppm): 1.6–2.4 (6H, m), 2.95 (4H, m), 3.86 (4H, m), 4.32 (1H, m), 5.3–5.4 (1H, m), 7.12 (1H, ddd, J=1, 7, 8 Hz), 7.48 (1H, d, J=8.5 Hz), 7.59 (1H, ddd, J=1.5, 7, 8.5 Hz), 7.87 (1H, dd, J=1.5, 8 Hz)

Example 2

4-[trans-(2-Hydroxycyclopentan-1-yl)oxy]-2-(1-piperazinyl)quinazoline monoacetate:

4-[trans-(2-Hydroxycyclopentan-1-yl)oxy]-2-(1-piperazinyl)quinazoline (cf. Example 1) (2.70 g) is dissolved in acetone (55 ml) with heating, and the solution is filtered, and to the filtrate is added acetic acid (0.52 ml), and the mixture is allowed to stand at room temperature. The precipitated crystals are separated by filtration to give 4-[trans-(2-hydroxycyclopentan-1-yl)oxy]-2-(1-piperazinyl)quinazoline monoacetate (3.00 g) as crystals.

M.p.: around 165° C. (dec.)

NMR (300 MHz, DMSO-d$_6$, δppm): 1.5–2.1 (5H, m), 1.89 (3H, s), 2.1–2.3 (1H, m), 2.80 (4H, m), 3.79 (4H, m), 4.23 (1H, m), 5.28 (1H, m), 5.0–5.5 (3H, br), 7.16 (1H, ddd, J=1, 7, 8 Hz), 7.40 (1H, d, J=8.5 Hz), 7.63 (1H, ddd, J=1.5, 7, 8.5 Hz), 7.82 (1H, dd, J=1.5, 8 Hz)

Elementary analysis for $C_{19}H_{26}N_4O_4$:

Calcd. (%): C,60.95; H,7.00; N,14.96

Found (%): C,60.76; H,6.95; N,14.85

Example 3

4-[cis-(2-Hydroxycyclopentan-1-yl)oxy]-2-(1-piperazinyl)quinazoline:

2,4-Dichloroquinazoline (1.95 g) and ciscyclopentane-1,2-diol [manufactured by Aldrich Co.] (1.0 g) are dissolved in dioxane (20 ml), and thereto is added gradually 60% sodium hydride (in oil) (0.39 g) under water-cooling, and the mixture is stirred at room temperature for 1 hour. The reaction mixture is added to ice-water (100 ml) and extracted with ethyl acetate twice. The extract is washed with water, dried over anhydrous sodium sulfate and evaporated to dryness under reduced pressure. The resulting residue is dissolved in dioxane (20 ml), and the mixture is slowly added dropwise to a solution of piperazine (2.8 g) in dioxane (10 ml) with stirring at 70° C., and the mixture is stirred at the same temperature for one hour. The reaction mixture is poured into water and extracted with chloroform. The extract is washed with water, dried over anhydrous sodium sulfate, and evaporated to dryness under reduced pressure. The resulting residue is purified by medium pressure liquid column chromatography (eluent, chloroform:methanol=10:1, v/v) to give 4-[cis-(2-hydroxycyclopentan-1-yl)oxy]-2-(1-piperazinyl)-quinazoline (1.47 g).

NMR (300 MHz, CDCl$_3$, δppm): 1.6–2.3 (8H, m), 2.94 (4H, m), 3.86 (4H, m), 4.40 (1H, m), 5.41 (1H, m), 7.14 (1H, ddd, J=1, 7, 8 Hz), 7.49 (1H, dt, J=1, 8.5 Hz), 7.60 (1H, ddd, J=1.5, 7, 8.5 Hz), 7.91 (1H, ddd, J=0.5, 1.5, 8 Hz)

Example 4
4-[cis-(2-Hydroxycyclopentan-1-yl)oxy]-2-(1-piperazinyl)quinazoline monoacetate:

4-[cis-(2-Hydroxycyclopentan-1-yl)oxy]-2-(1-piperazinyl)quinazoline (cf. Example 3) (0.6 g) is dissolved in ethanol (10 ml), and thereto is added acetic acid (0.14 g). Undissolved material is filtered off, and the mixture is evaporated to dryness under reduced pressure. The resulting residue is further recrystallized from acetone to give 4-[cis-(2-hydroxycyclopentan-1-yl)oxy]-2-(1-piperazinyl) quinazoline monoacetate (0.45 g) as crystals.

M.p.: around 138° C. (dec.)

NMR (300 MHz, DMSO-d$_6$, δppm): 1.5–2.2 (6H, m), 1.88 (3H, s), 2.83 (4H, m), 3.79 (4H, m), 4.25 (1H, m), 5.28 (1H, m), 5.5–6.5 (3H, br), 7.17 (1H, ddd, J=1, 7, 8 Hz), 7.40 (1H, d, J=8.5 Hz), 7.63 (1H, ddd, J=1.5, 7, 8.5 Hz), 8.01 (1H, dd, J=1.5, 8 Hz)

Elementary analysis for C$_{19}$H$_{26}$N$_4$O$_4$:

Calcd. (%): C,60.95; H,7.00; N,14.96

Found (%): C,60.88; H,7.05; N,15.09

Example 5
4-[(1S,2S)-(2-Hydroxycyclopentan-1-yl)oxy]-2-(1-piperazinyl)quinazoline:

To a solution of (1S,2S)-cyclopentane-1,2-diol [manufactured by Fluka Co., cf. J. Org. Chem., 53, 1823 (1988)] (1.00 g) and 2,4-dichloroquinazoline (1.85 g) in dimethylformamide (9 ml) is added gradually 60% sodium hydride (in oil) (409 mg) with stirring under ice-cooling, and the mixture is stirred at room temperature for 1 hour and 20 minutes. The reaction mixture is diluted with ethyl acetate and washed with water 5 times. The resulting ethyl acetate solution is dried over anhydrous magnesium sulfate and evaporated to dryness under reduced pressure, and the residue is briefly purified with medium pressure column chromatography (eluent, chloroform) to give an oily substance. The oily substance thus obtained is dissolved in dioxane (8 ml), and the mixture is slowly added dropwise to a solution of piperazine (2.21 g) in dioxane (10 ml) with stirring at 70° C., and the mixture is stirred at the same temperature for 40 minutes. The reaction mixture is diluted with ethyl acetate, washed with water, and dried over anhydrous magnesium sulfate. The resulting solution is evaporated to dryness under reduced pressure, and the residue is purified by medium pressure liquid column chromatography (eluent, chloroform:methanol=10:1, 5:1, v/v) to give 4-[(1S,2S)-(2-hydroxycyclopentan-1-yl)oxy]-2-(1-piperazinyl)-quinazoline (1.03 g) as crystals.

NMR (300 MHz, CDCl$_3$, δppm): 1.6–2.4 (6H, m), 2.95 (4H, m), 3.86 (4H, m), 4.32 (1H, m), 5.3–5.4 (1H, m), 7.12 (1H, ddd, J=1, 7, 8 Hz), 7.49 (1H, d, J=8.5 Hz), 7.59 (1H, ddd, J=1.5, 7, 8.5 Hz), 7.87 (1H, dd, J=1.5, 8 Hz)

Example 6
4-[(1S,2S)-(2-Hydroxycyclopentan-1-yl)oxy]-2-(1-piperazinyl)quinazoline monoacetate:

4-[(1S,2S)-(2-Hydroxycyclopentan-1-yl)oxy]-2-(1-piperazinyl)quinazoline (cf. Example 5) (1.03 g) is dissolved in acetone (35 ml) with heating, and the solution is filtered, and to the filtrate is added acetic acid (0.20 ml), and the mixture is allowed to stand at room temperature. The precipitated crystals are separated by filtration to give 4-[(1S,2S)-(2-hydroxycyclopentan-1-yl)oxy]-2-(1-piperazinyl)quinazoline monoacetate (990 mg) as crystals.

M.p.: around 164° C. (dec.)

NMR (300 MHz, DMSO-d$_6$, δppm): 1.5–2.1 (5H, m), 1.89 (3H, s), 2.1–2.3 (1H, m), 2.80 (4H, m), 3.79 (4H, m), 4.23 (1H, m), 5.10 (3H, br), 5.27 (1H, m), 7.16 (1H, ddd, J=1, 7, 8 Hz), 7.39 (1H, d, J=8.5 Hz), 7.63 (1H, ddd, J=1.5, 7, 8.5 Hz), 7.82 (1H, dd, J=1.5, 8 Hz)

Elementary analysis for C$_{19}$H$_{26}$N$_4$O$_4$:

Calcd. (%): C,60.95; H,7.00; N,14.96

Found (%): C,60.83; H,6.96; N,14.92

Example 7
4-[(1R,2R)-(2-Hydroxycyclopentan-1-yl)oxy]-2-(1-piperazinyl)quinazoline:

To a solution of (1R,2R)-cyclopentane-1,2-diol [manufactured by Fluka Co.] (1.16 g) and 2,4-dichloroquinazoline (2.00 g) in dimethylformamide (40 ml) is added gradually 60% sodium hydride (in oil) (0.4 g) with stirring under ice-cooling, and the mixture is stirred at room temperature for 2 hours. The reaction mixture is poured into water and extracted with ethyl acetate twice, and the extract is washed with water, dried over anhydrous sodium sulfate and evaporated to dryness under reduced pressure. The resulting residue is briefly purified with medium pressure column chromatography (eluent, chloroform:methanol=100:1, v/v) to give an oily substance. The oily substance thus obtained is dissolved in dioxane (20 ml), and the mixture is slowly added dropwise to a solution of piperazine (1.9 g) in dioxane (20 ml) with stirring at 70° C., and the mixture is stirred at the same temperature for one hour. The reaction mixture is poured into ice-water and extracted with chloroform. The extract is wished with water, dried over anhydrous sodium sulfate, and evaporated to dryness under reduced pressure. The resulting residue is purified by medium pressure liquid column chromatography (eluent, chloroform:methanol=20:1, 5:1, v/v) to give 4-[(1R,2R)-(2-hydroxycyclopentan-1-yl)oxy]-2-(1-piperazinyl)-quinazoline (1.1 g).

NMR (300 MHz, CDCl$_3$, δppm): 1.6–2.4 (6H, m), 2.96 (4H, m), 3.7–4.0 (4H, m), 4.31 (1H, m), 5.34 (1H, m), 7.12 (1H, ddd, J=1, 7, 8 Hz), 7.48 (1H, dt, J=1, 8.5 Hz), 7.59 (1H, ddd, J=1.5, 7, 8.5 Hz), 7.89 (1H, ddd, J=0.5, 1.5, 8 Hz)

Example 8
4-[(1R,2R)-(2-Hydroxycyclopentan-1-yl)oxy]-2-(1-piperazinyl)quinazoline monoacetate:

4-[(1R,2R)-(2-Hydroxycyclopentan-1-yl)oxy]-2-(1-piperazinyl)quinazoline (cf. Example 7) (1.1 g) is dissolved in acetone (30 ml), and thereto is added acetic acid (0.23 g). The precipitated crystals are separated by filtration and recrystallized from acetone to give 4-[(1R,2R)-(2-hydroxycyclopentan-1-yl)oxy]-2-(1-piperazinyl) quinazoline monoacetate (0.77 g).

M.p.: around 164° C. (dec.)

NMR (300 MHz, DMSO-d$_6$, δppm): 1.5–2.0 (5H, m), 1.89 (3H, s), 2.2–2.3 (1H, m), 2.80 (4H, m), 3.79 (4H, m), 4.23 (1H, m), 5.28 (1H, m), 5.35 (3H, br), 7.16 (1H, ddd, J=1, 7, 8 Hz), 7.39 (1H, d, J=8.5 Hz), 7.63 (1H, ddd, J=1.5, 7, 8.5 Hz), 7.82 (1H, dd, J=1.5, 8 Hz)

Elementary analysis for C$_{19}$H$_{26}$N$_4$O$_4$:

Calcd. (%): C,60.95; H,7.00; N,14.96

Found (%): C,60.81; H,6.89; N,14.84

Example 9
4-[(3-Hydroxycyclopentan-1-yl)oxy]-2-(1-piperazinyl)quinazoline:

(1) 2-[4-(t-Butoxycarbonyl)piperazin-1-yl]-4-[(3-hydroxycyclopentan-1-yl)oxy] quinazoline:

2,4-Dichloroquinazoline (2.0 g) and cyclopentane-1,3-diol [manufactured by Aldrich Co.] (1.16 g) are dissolved in dimethylformamide (40 ml), and thereto is added gradually 60% sodium hydride (in oil) (0.4 g) underwater-cooling, and the mixture is exposed to ultrasonic treatment to some extent and is stirred at room temperature for 2 hours. The reaction mixture is poured into ice-water and extracted with ethyl acetate. The extract is washed with water, dried over anhydrous sodium sulfate and evaporated to dryness under reduced pressure. The resulting residue is briefly purified by medium pressure column chromatography (eluent, chloroform:methanol=100:1, v/v) to give an oily substance. The thus obtained oily substance is dissolved in dioxane (20 ml), and the mixture is slowly added dropwise to a solution of piperazine (2.3 g) in dioxane (20 ml) with stirring at 70° C., and the mixture is stirred at 70° C. for one hour. The reaction mixture is poured into water and extracted with chloroform. The extract is washed with water, dried over anhydrous sodium sulfate, and evaporated to dryness under reduced pressure. The resulting residue (1.8 g) is dissolved in chloroform (20 ml) and thereto is added di-t-butyl dicarbonate (1.2 g), and the mixture is stirred at room temperature for 30 minutes, and the reaction mixture is evaporated to dryness under reduced pressure. The resulting residue is purified by medium pressure liquid column chromatography (eluent, chloroform:methanol=100:1, v/v) to give 2-[4-(t-butoxycarbonyl)piperazin-1-yl]-4-[(3-hydroxycyclopentan-1-yl)oxy]quinazoline (0.95 g).

NMR (60 MHz, CDCl$_3$, δppm): 1.5 (9H, s), 1.7–2.7 (6H, m), 2.9 (1H, s), 3.6 (4H, m), 3.9 (4H, m), 4.6 (1H, m), 5.7 (1H, m), 6.9–8.0 (4H, m)

(2) 4-[(3-Hydroxycyclopentan-1-yl)oxy]-2-(1-piperazinyl) quinazoline:

Trifluoroacetic acid (10 ml) is added to 2-[4-(t-butoxycarbonyl)piperazin-1-yl]-4-[(3-hydroxycyclopentan-1-yl)oxy] quinazoline (0.95 g), and the mixture is stirred at room temperature for 30 minutes. The reaction mixture is evaporated to dryness under reduced pressure, and the resulting residue is dissolved in ethyl acetate. The solution is washed with aqueous sodium hydrogen carbonate solution and then with water, and dried over anhydrous sodium sulfate, and then is evaporated to dryness under reduced pressure to give 4-[(3-hydroxycyclopentan-1-yl)oxy]-2-(1-piperazinyl)quinazoline (0.55 g).

NMR (250 MHz, CDCl$_3$, δppm): 1.6–2.6 (6H, m), 2.92 (4H, m), 3.10 (2H, br), 3.88 (4H, m), 4.3–4.6 (1H, m), 5.4–5.8 (1H, m), 7.0–7.2 (1H, m), 7.4–7.6 (2H, m), 7.8–8.0 (1H, m)

Example 10
4-[(3-Hydroxycyclopentan-1-yl)oxy]-2-(1-piperazinyl)quinazoline monoacetate:

4-[(3-Hydroxycyclopentan-1-yl)oxy]-2-(1-piperazin-yl)quinazoline (cf. Example 9) (0.55 g) is dissolved in acetone (10 ml), and thereto is added acetic acid (0.11 g), and the mixture is evaporated to dryness under reduced pressure. The resulting residue is further recrystallized from acetone to give 4-[(3-hydroxycyclopentan-1-yl)oxy]-2-(1-piperazinyl)quinazoline monoacetate (0.45 g).

M.p.: 146–148° C.

NMR (300 MHz, DMSO-d$_6$, δppm): 1.5–2.5 (6H, m), 1.89 (3H, s), 2.80 (4H, m), 3.77 (4H, m), 4.1–4.4 (1H, m), 5.4–5.7 (1H, m), 4.0–5.5 (3H, br), 7.16 (1H, m), 7.38 (1H, m), 7.62 (1H, m), 7.83 (1H, m)

Elementary analysis for C$_{19}$H$_{26}$N$_4$O$_4$:

Calcd. (%): C,60.95; H,7.00; N,14.96

Found (%): C,60.69; H,6.94; N,14.94

Example 11
4-[trans-(4-Hydroxytetrahydrofuran-3-yl)oxy]-2-(1-piperazinyl)quinazoline:

To a solution of trans-tetrahydrofuran-3,4-diol [cf. J. Chem. Soc., 248 (1959)] (2.15 g) and 2,4-dichloroquinazoline (3.42 g) in dimethylformamide (30 ml) is added gradually 60% sodium hydride (in oil) (894 mg) with stirring under ice-cooling, and the mixture is stirred at room temperature for 50 minutes. The reaction mixture is diluted with ethyl acetate and washed with water 5 times. The resulting ethyl acetate solution is dried over anhydrous magnesium sulfate and is evaporated to dryness under reduced pressure, and the residue is dissolved in dioxane (20 ml). The mixture is slowly added dropwise to a solution of piperazine (7.40 g) in dioxane (40 ml) with stirring at 60° C., and the mixture is stirred at the same temperature for one hour. The reaction mixture is diluted with ethyl acetate, washed with water, and dried over anhydrous magnesium sulfate. The resulting solution is evaporated to dryness under reduced pressure, and the residue is purified by medium pressure column chromatography (eluent, chloroform:methanol=10:1, 5:1, v/v), and the resulting crystals are recrystallized from acetone-diethyl ether to give 4-[trans-(4-hydroxytetrahydrofuran-3-yl)oxy]-2-(1-piperazinyl) quinazoline (553 mg) as crystals.

M.p.: 148–154° C.

NMR (300 MHz, DMSO-d$_6$, δppm): 2.76 (4H, m), 3.32 (1H, br), 3.67 (1H, dd, J=2, 9.5 Hz), 3.75 (4H, m), 3.85 (1H, dd, J=1.5, 10.5 Hz), 3.99 (1H, dd, J=4.5, 9.5 Hz), 4.18 (1H, dd, J=4.5, 10.5 Hz), 4.42 (1H, m), 5.42 (1H, m), 5.49 (1H, br), 7.17 (1H, ddd, J=1, 7, 8 Hz), 7.40 (1H, d, J=8.5 Hz), 7.64 (1H, ddd, J=1.5, 7, 8.5 Hz), 7.83 (1H, dd, J=1.5, 8 Hz)

Elementary analysis for C$_{16}$H$_{20}$N$_4$O$_3$:

Calcd. (%): C,60.75; H,6.37; N,17.71

Found (%): C,60.78; H,6.41; N,17.52

Example 12
4-[trans-(4-Hydroxytetrahydrofuran-3-yl)oxy]-2-(1-piperazinyl)quinazoline monoacetate:

4-[trans-(4-Hydroxytetrahydrofuran-3-yl)oxy]-2-(1-piperazinyl)quinazoline (cf. Example 11) (200 mg) is dissolved in acetone (20 ml) with heating, and the solution is filtered, and the filtrate is concentrated and thereto is added acetic acid (50 mg), and the mixture is allowed to stand at room temperature. The precipitated crystals are separated by filtration to give 4-[trans-(4-hydroxytetrahydrofuran-3-yl)oxy]-2-(1-piperazinyl)quinazoline monoacetate (171 mg).

M.p.: around 182° C. (dec.)

NMR (300 MHz, DMSO-d$_6$, δppm): 1.89 (3H, s), 2.80 (4H, m), 3.66 (1H, dd, J=2, 9.5 Hz), 3.78 (4H, m), 3.86 (1H, dd, J=1.5, 10.5 Hz), 3.99 (1H, dd, J=4.5, 9.5 Hz), 4.18 (1H, dd, J=4.5, 10.5 Hz), 4.43 (1H, m), 5.31 (3H, br), 5.42 (1H, m), 7.17 (1H, ddd, J=1, 7, 8 Hz), 7.41 (1H, d, J=8.5 Hz), 7.65 (1H, ddd, J=1.5, 7, 8.5 Hz), 7.84 (1H, dd, J=1.5, 8 Hz)

Elementary analysis for C$_{18}$H$_{24}$N$_4$O$_5$:

Calcd. (%): C,57.44; H,6.43; N,14.88

Found (%): C,57.41; H,6.41; N,14.94

Example 13
4-[trans-(4-Hydroxytetrahydrofuran-3-yl)oxy]-2-(1-piperazinyl)quinazoline monohydrochloride:

To a solution of 4-[trans-(4-hydroxytetrahydrofuran-3-yl)oxy]-2-(1-piperazinyl)quinazoline monoacetate (cf. Example 12) (150 mg) in acetone (10 ml) is added 2N HCl-methanol (0.26 ml), and the mixture is evaporated to dryness under reduced pressure, and the residue is washed with acetone. The obtained crystals are recrystallized from methanol-acetone to give 4-[trans-(4-hydroxytetrahydrofuran-3-yl)oxy]-2-(1-piperazinyl)quinazoline monohydrochloride (96 mg) as crystals.

M.p.: around 240° C. (dec.)

NMR (300 MHz, DMSO-$d_6$, δppm): 3.18 (4H, m), 3.67 (1H, dd, J=2, 9.5 Hz), 3.88 (1H, dd, J=1.5, 10.5 Hz), 3.99 (1H, dd, J=4.5, 9.5 Hz), 4.08 (4H, m), 4.20 (1H, dd, J=4.5, 10.5 Hz), 4.45 (1H, br), 5.43 (1H, m), 5.61 (1H, d, J=4 Hz), 7.26 (1H, ddd, J=1, 7, 8 Hz), 7.48 (1H, d, J=8.5 Hz), 7.72 (1H, ddd, J=1.5, 7, 8.5 Hz), 7.89 (1H, dd, J=1.5, 8 Hz), 9.49 (2H, br)

Elementary analysis for $C_{16}H_{20}N_4O_3 \cdot HCl$:

Calcd. (%): C,54.47; H,6.00; N,15.88

Found (%): C,54.50; H,5.98; N,15.95

Example 14
4-[cis-(4-Hydroxytetrahydrofuran-3-yl)oxy]-2-(1-piperazinyl)quinazoline:

To a solution of 2,4-dichloroquinazoline (1.0 g) and 1,4-anhydroerythritol (manufactured by Aldrich Co.) (0.52 g) in dimethylformamide (20 ml) is added gradually 60% sodium hydride (in oil) (0.2 g) under water-cooling, and the mixture is stirred at room temperature for one hour. The reaction mixture is poured into ice-water, and extracted with ethyl acetate. The ethyl acetate solution is washed with water, dried over anhydrous sodium sulfate and evaporated to dryness under reduced pressure. The resulting residue is dissolved in dioxane (20 ml), and the mixture is slowly added dropwise to a solution of piperazine (2.2 g) in dioxane (20 ml) with stirring at 70° C., and the mixture is stirred at the same temperature for one hour. The reaction mixture is poured into ice-water and extracted with chloroform. The extract is washed with water, dried over anhydrous sodium sulfate, and is evaporated to dryness under reduced pressure. The resulting residue is purified by medium pressure column chromatography (eluent, chloroform:methanol=20:1, 5:1, v/v), and the resulting crystals are recrystallized from ethanol to give 4-[cis-(4-hydroxytetrahydrofuran-3-yl)oxy]-2-(1-piperazin-yl)quinazoline (0.31 g).

NMR (300 MHz, CDCl$_3$, δppm): 2.14 (2H, br), 2.93 (4H, m), 3.83 (4H, m), 3.90 (1H, dd, J=5, 9.5 Hz), 4.05 (1H, dd, J=5, 10 Hz), 4.10 (1H, dd, J=5.5, 9.5 Hz), 4.28 (1H, dd, J=6, 10 Hz), 4.63 (1H, q, J=5 Hz), 5.54 (1H, dt, J=5, 6 Hz), 7.16 (1H, ddd, J=1, 7, 8 Hz), 7.50 (1H, dt, J=1, 8.5 Hz), 7.61 (1H, ddd, J=1.5, 7, 8.5 Hz), 7.92 (1H, dd, J=1.5, 8 Hz)

Example 15
4-[cis-(4-Hydroxytetrahydrofuran-3-yl)oxy]-2-(1-piperazinyl)quinazoline monoacetate:

4-[cis-(4-Hydroxytetrahydrofuran-3-yl)oxy]-2-(1-piperazinyl)quinazoline (cf. Example 14) (0.95 g) is dissolved in methanol (20 ml), and thereto is added acetic acid (0.22 g), and the mixture is evaporated to dryness under reduced pressure. The resulting residue is recrystallized from acetonitrile-methanol to give 4-[cis-(4-hydroxytetrahydrofuran-3-yl)oxy]-2-(1-piperazinyl)quinazoline monoacetate (0.8 g) as crystals.

M.p.: 165–166° C.

NMR (300 MHz, DMSO-$d_6$, δppm): 1.89 (3H, s), 2.80 (4H, m), 3.67 (1H, dd, J=5, 9 Hz), 3.76 (4H, m), 3.82 (1H, dd, J=5, 9.5 Hz), 3.96 (1H, dd, J=5.5, 9 Hz), 4.17 (1H, dd, J=6, 9.5 Hz), 4.48 (1H, q, J=5.5 Hz), 5.0–6.0 (3H, br), 5.49 (1H, q, J=5.5 Hz), 7.16 (1H, ddd, J=1, 7, 8 Hz), 7.40 (1H, d, J=8.5 Hz), 7.65 (1H, ddd, J=1.5, 7, 8.5 Hz), 8.00 (1H, dd, J=1.5, 8 Hz)

Elementary analysis for $C_{18}H_{24}N_4O_5$:

Calcd. (%): C,57.44; H,6.43; N,14.88

Found (%): C,57.28; H,6.38; N,14.92

Example 16
4-[(3S,4S)-(4-Hydroxytetrahydrofuran-3-yl)oxy]-2-(1-piperazinyl)quinazoline:

To a solution of 1,4-anhydro-L-threitol [manufactured by Aldrich Co., cf. J. Am. Chem. Soc., 74, 5336 (1952)] (7.34 g) and 2,4-dichloroquinazoline (5.00 g) in dimethylformamide (42 ml) is added gradually 60% sodium hydride (in oil) (1.92 g) with stirring under ice-cooling, and the mixture is stirred at room temperature for one hour and 10 minutes. The reaction mixture is diluted with ethyl acetate and washed with water 5 times. The ethyl acetate solution is dried over anhydrous magnesium sulfate and evaporated to dryness under reduced pressure. The resulting residue is briefly purified by medium pressure liquid column chromatography [eluent, chloroform, (chloroform:methanol=200:1, v/v)] to give an oily substance. The oily substance is dissolved in dioxane (35 ml), and the mixture is slowly added dropwise to a solution of piperazine (9.61 g) in dioxane (70 ml) with stirring at 50° C., and the mixture is stirred at the same temperature for 1.5 hour. The reaction mixture is diluted with ethyl acetate, washed with water, and dried over anhydrous magnesium sulfate. The resulting solution is evaporated to dryness under reduced pressure, and the residue is purified by medium pressure column chromatography (eluent, chloroform:methanol=10:1, 5:1, v/v) to give 4-[(3S,4S)-(4-hydroxytetrahydrofuran-3-yl)oxy]-2-(1-piperazinyl)quinazoline (2.47 g) as crystals.

NMR (300 MHz, DMSO-$d_6$, δppm): 2.79 (4H, m), 3.24 (1H, br), 3.66 (1H, dd, J=2, 9.5 Hz), 3.77 (4H, m), 3.85 (1H, dd, J=1.5, 10.5 Hz), 3.99 (1H, dd, J=4.5, 9.5 Hz), 4.18 (1H, dd, J=4.5, 10.5 Hz), 4.42 (1H, br), 5.41 (1H, m), 5.50 (1H, br), 7.17 (1H, ddd, J=1, 7, 8 Hz), 7.41 (1H, d, J=8.5 Hz), 7.65 (1H, ddd, J=1.5, 7, 8.5 Hz), 7.84 (1H, dd, J=1.5, 8 Hz)

Example 17
4-[(3S,4S)-(4-Hydroxytetrahydrofuran-3-yl)oxy]-2-(1-piperazinyl)quinazoline monoacetate:

4-[(3S,4S)-(4-Hydroxytetrahydrofuran-3-yl)oxy]-2-(1-piperazinyl)quinazoline (cf. Example 16) (2.37 g) is dissolved in acetone (100 ml) with heating, and the mixture is filtered. The filtrate is concentrated to about 60 ml volume, and thereto is added acetic acid (495 mg), and the mixture is allowed to stand at room temperature. The precipitated crystals are separated by filtration to give 4-[(3S,4S)-(4-hydroxytetrahydrofuran-3-yl)oxy]-2-(1-piperazinyl)quinazoline monoacetate (2.37 g).

M.p.: around 183° C. (dec.)

NMR (300 MHz, DMSO-$d_6$, δppm): 1.89 (3H, s), 2.80 (4H, m), 3.67 (1H, dd, J=2, 9.5 Hz), 3.78 (4H, m), 3.85 (1H, dd, J=1.5, 10.5 Hz), 3.99 (1H, dd, J=4.5, 9.5 Hz), 4.18 (1H, dd, J=4.5, 10.5 Hz), 4.42 (1H, m), 5.42 (1H, m), 5.96 (3H, br), 7.17 (1H, ddd, J=1, 7, 8 Hz), 7.41 (1H, d, J=8.5 Hz), 7.65 (1H, ddd, J=1.5, 7, 8.5 Hz), 7.84 (1H, dd, J=1.5, 8 Hz)

Elementary analysis for $C_{18}H_{24}N_4O_5$:

Calcd. (%): C,57.44; H,6.43; N,14.88

Found (%): C,57.31; H,6.42; N,14.94

Example 18
4-[(3S,4S)-(4-Hydroxytetrahydrofuran-3-yl)oxy]-2-(1-piperazinyl)quinazoline monohydrochloride:

To a solution of 4-[(3S,4S)-(4-hydroxytetrahydrofuran-3-yl)oxy]-2-(1-piperazinyl)quinazoline monoacetate (cf. Example 17) (1.54 g) in methanol (44 ml) is added 2N HCl-methanol (2.25 ml), and the mixture is evaporated to dryness under reduced pressure. The residue is washed with acetone and recrystallized from methanol-acetone to give 4-[(3S,4S)-(4-hydroxytetrahydrofuran-3-yl)oxy]-2-(1-piperazinyl)quinazoline monohydrochloride (775 mg) as crystals.

M.p.: around 241° C. (dec.)

NMR (300 MHz, DMSO-$d_6$, δppm): 3.18 (4H, m), 3.67 (1H, dd, J=2, 9.5 Hz), 3.89 (1H, dd, J=1.5, 10.5 Hz), 3.99 (1H, dd, J=4.5, 9.5 Hz), 4.07 (4H, m), 4.20 (1H, dd, J=4.5, 10.5 Hz), 4.45 (1H, br), 5.43 (1H, m), 5.60 (1H, d, J=4 Hz), 7.26 (1H, ddd, J=1, 7, 8 Hz), 7.48 (1H, d, J=8.5 Hz), 7.72 (1H, ddd, J=1.5, 7, 8.5 Hz), 7.90 (1H, dd, J=1.5, 8 Hz), 9.39 (2H, br)

Elementary analysis for $C_{16}H_{20}N_4O_3 \cdot HCl$:

Calcd. (%): C,54.47; H,6.00; N,15.88

Found (%): C,54.62; H,5.98; N,15.94

Example 19
4-[(3R,4R)-(4-Hydroxytetrahydrofuran-3-yl)oxy]-2-(1-piperazinyl)quinazoline:

To a solution of 1,4-anhydro-D-threitol [prepared from D-threiol (manufactured by Fluka Co.) in the same manner as in the preparation of 1,4-anhydro-L-threitol (cf. J. Am. Chem. Soc., 74, 5336 (1952)] (11.43 g) and 2,4-dichloroquinazoline (16.8 g) in dimethylformamide (78 ml) is added gradually 60% sodium hydride (in oil) (4.39 g) with stirring under ice-cooling, and the mixture is stirred under ice-cooling for 15 minutes and further at room temperature for 30 minutes. The reaction mixture is diluted with ethyl acetate and washed with water 5 times. The ethyl acetate solution is dried over anhydrous magnesium sulfate and evaporated to dryness under reduced pressure. The resulting residue is briefly purified by medium pressure liquid column chromatography [eluent, chloroform] to give a crystalline substance. The crystalline substance is dividedly added to a solution of piperazine (20.7 g) in dioxane (95 ml) with stirring at 55° C., and the mixture is stirred at the same temperature for 30 minutes. The reaction mixture is diluted with ethyl acetate, washed with water, and dried over anhydrous magnesium sulfate. The resulting solution is evaporated to dryness under reduced pressure, and the residue is purified by medium pressure column chromatography (eluent, chloroform:methanol=10:1, 5:1, v/v) to give 4-[(3R,4R)-(4-hydroxytetrahydrofuran-3-yl)oxy]-2-(1-piperazinyl)quinazoline (5.83 g) as crystals. A part thereof is crystallized from ethanol-ether for obtaining the following physical data.

M.p. 164–166° C.

$[\alpha]_D^{20}$=−48° (c=1.0, methanol)

NMR (300 MHz, DMSO-$d_6$, δppm): 2.76 (4H, m), 3.33 (1H, br), 3.66 (1H, dd, J=2, 9.5 Hz), 3.75 (4H, m), 3.85 (1H, dd, J=1.5, 10.5 Hz), 3.99 (1H, dd, J=4.5, 9.5 Hz), 4.18 (1H, dd, J=4.5, 10.5 Hz), 4.42 (1H, br), 5.41 (1H, m), 5.51 (1H, br), 7.17 (1H, ddd, J=1, 7, 8 Hz), 7.40 (1H, d, J=8.5 Hz), 7.64 (1H, ddd, J=1.5, 7, 8.5 Hz), 7.83 (1H, dd, J=1.5, 8 Hz)

Elementary analysis for $C_{16}H_{20}N_4O_3$:

Calcd. (%): C,60.75; H,6.37; N,17.71

Found (%): C,60.76; H,6.32; N,17.71

Example 20
4-[(3R,4R)-(4-Hydroxytetrahydrofuran-3-yl)oxy]-2-(1-piperazinyl)quinazoline monoacetate:

4-[(3R,4R)-(4-Hydroxytetrahydrofuran-3-yl)oxy]-2-(1-piperazinyl)quinazoline (cf. Example 19) (758 mg) is dissolved in methanol, and the mixture is evaporated to dryness under reduced pressure. The residue is dissolved in acetone (15 ml), and the mixture is filtered, and to the filtrate is added acetic acid (202 mg), and the mixture is allowed to stand at room temperature. The precipitated crystals are separated by filtration to give 4-[(3R,4R)-(4-hydroxytetrahydrofuran-3-yl)oxy]-2-(1-piperazinyl) quinazoline monoacetate (796 mg) as crystals.

M.p.: around 182° C. (dec.)

NMR (300 MHz, DMSO-$d_6$, δppm): 1.89 (3H, s), 2.79 (4H, m), 3.66 (1H, dd, J=2, 9.5 Hz), 3.77 (4H, m), 3.85 (1H, dd, J=1.5, 10.5 Hz), 3.99 (1H, dd, J=4.5, 9.5 Hz), 4.18 (1H, dd, J=4.5, 10.5 Hz), 4.42 (1H, m), 4.98 (3H, br), 5.42 (1H, m), 7.17 (1H, ddd, J=1, 7, 8 Hz), 7.41 (1H, d, J=8.5 Hz), 7.65 (1H, ddd, J=1.5, 7, 8.5 Hz), 7.84 (1H, dd, J=1.5, 8 Hz)

Elementary analysis for $C_{18}H_{24}N_4O_5$:

Calcd. (%): C,57.44; H,6.43; N,14.88

Found (%): C,57.37; H,6.36; N,14.93

Example 21
4-[(3R,4R)-(4-Hydroxytetrahydrofuran-3-yl)oxy]-2-(1-piperazinyl)quinazoline ½ hydrochloride:

4-[(3R,4R)-(4-Hydroxytetrahydrofuran-3-yl)oxy]-2-(1-piperazinyl)quinazoline (cf. Example 19) (4.83 g) is dissolved in methanol (33 ml) with heating, and the mixture is filtered. To the filtrate is added 2N HCl-methanol (4.6 ml), and the mixture is allowed to stand at room temperature. The precipitated crystals are separated by filtration to give 4-[(3R,4R)-(4-hydroxytetrahydrofuran-3-yl)oxy]-2-(1-piperazinyl)quinazoline ½ hydrochloride (2.88 g) as crystals.

M.p.: around 219° C. (dec.)

$[\alpha]_D^{20}$=−35° (c=1.1, water)

NMR (300 MHz, DMSO-$d_6$, δppm): 2.98 (4H, m), 3.67 (1H, dd, J=2, 9.5 Hz), 3.8–4.0 (5H, m), 3.99 (1H, dd, J=4.5, 9.5 Hz), 4.19 (1H, dd, J=4.5, 10.5 Hz), 4.44 (1H, m), 5.43 (1H, m), 5.1–6.0 (1H, br), 7.22 (1H, ddd, J=1, 7, 8 Hz), 7.44 (1H, dt, J=1, 8.5 Hz), 7.68 (1H, ddd, J=1.5, 7, 8.5 Hz), 7.87 (1H, dd, J=1.5, 8 Hz)

Elementary analysis for $C_{16}H_{20}N_4O_3 \cdot$½ HCl:

Calcd. (%): C,57.44; H,6.18; N,16.74

Found (%): C,57.33; H,6.17; N,16.79

Example 22
4-[(3R,4R)-(4-Hydroxytetrahydrofuran-3-yl)oxy]-2-(1-piperazinyl)quinazoline monohydrochloride:

4-[(3R,4R)-(4-Hydroxytetrahydrofuran-3-yl)oxy]-2-(1-piperazinyl)quinazoline ½ hydrochloride (cf. Example 21) (178 mg) is dissolved in methanol (3 ml) with heating, and thereto is added 2N HCl-methanol (0.32 ml) and acetone (10 ml), and the mixture is allowed to stand at room temperature. The precipitated crystals are separated by filtration to give 4-[(3R,4R)-(4-hydroxytetrahydrofuran-3-yl)oxy]-2-(1-piperazinyl)quinazoline monohydrochloride (124 mg) as crystals.

M.p.: around 238° C. (dec.)

NMR (300 MHz, DMSO-$d_6$, δppm): 3.19 (4H, m), 3.67 (1H, dd, J=2, 9.5 Hz), 3.89 (1H, dd, J=1.5, 10.5 Hz), 3.99 (1H, dd, J=4.5, 9.5 Hz), 4.07 (4H, m), 4.20 (1H, dd, J=4.5, 10.5 Hz), 4.45 (1H, br), 5.43 (1H, m), 5.59 (1H, d, J=4 Hz), 7.26 (1H, ddd, J=1, 7, 8 Hz), 7.48 (1H, d, J=8.5 Hz), 7.72 (1H, ddd, J=1.5, 7, 8.5 Hz), 7.90 (1H, dd, J=1.5, 8 Hz), 9.37 (2H, br)

Elementary analysis for $C_{16}H_{20}N_4O_3 \cdot HCl$:

Calcd. (%): C,54.47; H,6.00; N,15.88

Found (%): C,54.59; H,5.07; N,16.04

Example 23

4-[(3R,4R)-(4-Hydroxytetrahydrofuran-3-yl)oxy]-2-(1-piperazinyl)quinazoline ½ fumarate:

4-[(3R,4R)-(4-Hydroxytetrahydrofuran-3-yl)oxy]-2-(1-piperazinyl)quinazoline (cf. Example 19) (499 mg) and fumaric acid (192 mg) are dissolved in ethanol (20ml), and the mixture is allowed to stand at room temperature. The precipitated crystals are separated by filtration, and recrystallized from water-acetone to give 4-[(3R,4R)-(4-hydroxytetrahydrofuran-3-yl)oxy]-2-(1-piperazinyl) quinazoline ½ fumarate (462 mg) as crystals.

M.p.: around 185° C. (dec.)

NMR (300 MHz, DMSO-$d_6$, δppm): 2.96 (4H, m), 3.67 (1H, dd, J=2, 9.5 Hz), 3.8–4.0 (5H, m), 3.99 (1H, dd, J=4.5, 9.5 Hz), 4.19 (1H, dd, J=4.5, 10.5 Hz), 4.44 (1H, m), 5.43 (1H, m), 5.2–6.8 (2H, br), 6.65 (1H, s), 7.22 (1H, ddd, J=1, 7, 8 Hz), 7.44 (1H, d, J=8.5 Hz), 7.68 (1H, ddd, J=1.5, 7, 8.5 Hz), 7.87 (1H, dd, J=1.5, 8 Hz)

Elementary analysis for $C_{18}H_{22}N_4O_5 \cdot ¾H_2O$:

Calcd. (%): C,55.73; H,6.11; N,14.44

Found (%): C,55.90; H,6.08; N,14.61

Example 24

4-[(t-2,t-3-Dihydroxycyclopentan-r-1-yl)oxy]-2-(1-piperazinyl)quinazoline:

(1) 4-[(Cyclopent-2-en-1-yl)oxy]-2-(1-piperazinyl)quinazoline:

To a solution of 2-cyclopenten-1-ol [cf. J. Org. Chem., 40, 1864 (1975)] (996 mg) and 2,4-dichloroquinazoline (2.36 g) in dimethylformamide (10 ml) is added 60% sodium hydride (in oil) (568 mg) with stirring at room temperature, and the mixture is stirred at room temperature for 2 hours. The reaction mixture is diluted with ethyl acetate, and washed with water 5 times. The ethyl acetate solution is dried over anhydrous magnesium sulfate and evaporated to dryness under reduced pressure. The resulting residue is briefly purified with medium pressure column chromatography (eluent, chloroform) to give a crystalline substance. The crystalline substance is added to a solution of piperazine (4.02 g) in dioxane (26 ml) with stirring at 70° C., and the mixture is stirred at the same temperature for one hour. The reaction mixture is diluted with ethyl acetate, washed with water, dried over anhydrous magnesium sulfate, and evaporated to dryness under reduced pressure. The resulting residue is purified by medium pressure liquid column chromatography (eluent, chloroform:methanol=10:1, 5:1, v/v) to give 4-[(cyclopent-2-en-1-yl)oxy]-2-(1-piperazinyl)quinazoline (1.57 g) as crystals.

NMR (300 MHz, CDCl$_3$, δppm): 2.0–2.2 (1H, m), 2.3–2.7 (3H, m), 2.70 (1H, s), 2.98 (4H, m), 3.93 (4H, m), 6.0–6.1 (1H, m), 6.1–6.2 (2H, m), 7.10 (1H, ddd, J=1, 7, 8 Hz), 7.48 (1H, dt, J=1, 8.5 Hz), 7.57 (1H, ddd, J=1.5, 7, 8.5 Hz), 7.89 (1H, dd, J=1.5, 8 Hz)

(2) 2-[(4-(Benzyloxycarbonyl)piperazin-1-yl)]-4-[(cyclopent-2-en-1-yl)oxy]quinazoline:

To a solution of 4-[(cyclopent-2-en-1-yl)oxy]-2-(1-piperazinyl) quinazoline (1.47 g) in dry methylene chloride (15 ml) is added triethylamine (1.39 ml) with stirring under ice-cooling, and thereto is further added dropwise a solution of benzyl chlorocarbonate (0.75 ml) in dry methylene chloride (3 ml). The mixture is stirred at 0° C. for 4 hours, and the reaction mixture is diluted with chloroform and washed with water, and then dried over anhydrous magnesium sulfate. The resulting solution is evaporated to dryness under reduced pressure, and the residue is purified by medium pressure liquid column chromatography (eluent, chloroform) to give 2-[4-(benzyloxycarbonyl) piperazin-1-yl]-4-[(cyclopent-2-en-1-yl)oxy] quinazoline (1.85 g) as crystals.

NMR (300 MHz, CDCl$_3$, δppm): 2.0–2.1 (1H, m), 2.3–2.6 (2H, m), 2.5–2.7 (1H, m), 3.62 (4H, m), 3.93 (4H, br), 5.18 (2H, s), 6.0–6.1 (1H, m), 6.1–6.3 (2H, m), 7.12 (1H, ddd, J=1, 7, 8 Hz), 7.2–7.4 (5H, m), 7.48 (1H, dt, J=1, 8.5 Hz), 7.58 (1H, ddd, J=1.5, 7, 8.5 Hz), 7.91 (1H, dd, J=1.5, 8 Hz)

(3) 2-[4-(Benzyloxycarbonyl)piperazin-1-yl]-4-[(t-2,t-3-dihydroxycyclopentan-r-1-yl)oxy]quinazoline:

A mixture of 2-[4-(benzyloxycarbonyl)piperazin-1-yl]-4-[(cyclopent-2-en-1-yl)oxy]quinazoline (1.75 g), a solution of osmium tetroxide in t-butanol (osmium tetroxide 106 mg/t-butanol 8.36 g) (817 mg) and 4-methylmorpholine N-oxide (502 mg) in water (2 ml)-acetone (15 ml) is stirred at room temperature for 14 hours. Acetone is distilled off from the reaction mixture under reduced pressure, and the mixture is diluted with ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=100:1, v/v) to give 2-[4-(benzyloxycarbonyl)piperazin-1-yl]-4-[(t-2,t-3-dihydroxycyclopentan-r-1-yl)oxy]quinazoline (1.59 mg) as crystals.

NMR (300 MHz, CDCl$_3$, δppm): 1.8–2.0 (2H, m), 2.0–2.2 (1H, m), 2.4–2.6 (1H, m), 3.60 (4H, m), 3.86 (4H, br), 4.17 (1H, dd, J=4.5, 5.5 Hz), 4.2–4.3 (1H, m), 5.17 (2H, s), 5.48 (1H, dt, J=5.5, 9 Hz), 7.15 (1H, ddd, J=1, 7, 8 Hz), 7.3–7.5 (5H, m), 7.50 (1H, dt, J=1, 8.5 Hz), 7.62 (1H, ddd, J=1.5, 7, 8.5 Hz), 7.88 (1H, dd, J=1.5, 8 Hz)

(4) 4-[(t-2,t-3-Dihydroxycyclopentan-r-1-yl)oxy]-2-(1-piperazinyl)quinazoline:

To a solution of 2-[4-(benzyloxycarbonyl) piperazin-1-yl]-4-[(t-2,t-3-dihydroxycyclopentan-r-1-yl)oxy] quinazoline (160 mg) in methanol (8 ml) is added 10% palladium/carbon (32 mg), and the mixture is stirred under a hydrogen atmosphere and under atmospheric pressure at room temperature for 18 hours. The reaction mixture is filtered, and the filtrate is evaporated to dryness under reduced pressure to give 4-[(t-2,t-3-dihydroxycyclopentan-r-1-yl)oxy]-2-(1-piperazinyl)-quinazoline (105 mg) as foam.

NMR (300 MHz, CDCl$_3$, δppm): 1.8–2.2 (3H, m), 2.5–2.6 (1H, m), 2.96 (4H, m), 3.49 (1H, s), 3.85 (4H, m), 4.16 (1H, dd, J=4.5, 5.5 Hz), 4.2–4.3 (1H, m), 5.52 (1H, dt, J=5.5, 8.5 Hz), 7.14 (1H, ddd, J=1, 7, 8 Hz), 7.49 (1H, d, J=8.5 Hz), 7.61 (1H, ddd, J=1.5, 7, 8.5 Hz), 7.89 (1H, dd, J=1.5, 8 Hz)

Example 25

4-[(t-2,t-3-Dihydroxycyclopentan-r-1-yl)oxy]-2-(1-piperazinyl)quinazoline monoacetate:

4-[(t-2,t-3-Dihydroxycyclopentan-r-1-yl)oxy]-2-(1-piperazinyl)quinazoline (cf. Example 24) (229 mg) is dissolved in methanol (4 ml), and thereto is added acetic acid (44 mg), and the mixture is filtered. The filtrate is evaporated to dryness under reduced pressure, and the residue is recrystallized from ethanol-ethyl acetate to give 4-[(t-2,t-3-dihydroxycyclopentan-r-1-yl)oxy]-2-(1-piperazinyl)quinazoline monoacetate (167 mg) as crystals.

M.p.: around 164° C. (dec.)

NMR (300 MHz, DMSO-$d_6$, δppm): 1.4–1.7 (2H, m), 1.89 (3H, s), 1.8–2.1 (1H, m),2.3–2.5 (1H, m),2.79 (4H, m),3.77 (4H, m),4.0–4.1 (2H, m), 5.03 (4H, br), 5.30 (1H, dt, J=5, 8.5 Hz), 7.17 (1H, ddd, J=1, 7, 8 Hz), 7.40 (1H, d, J=8.5 Hz), 7.64 (1H, ddd, J=1.5, 7, 8.5 Hz), 7.87 (1H, dd, J=1.5, 8 Hz)

Elementary analysis for $C_{19}H_{26}N_4O_5$:
Calcd. (%): C,58.45; H,6.71; N,14.35
Found (%): C,58.24; H,6.75; N,14.16

Example 26

4-[(t-3,t-4-Dihydroxycyclopentan-r-1-yl)oxy]-2-(1-piperazinyl)quinazoline:

(1) 4-[(t-3,t-4-Diacetoxycyclopentan-r-1-yl)oxy]-2-(1-piperazinyl) quinazoline:

To a solution of t-3,t-4-diacetoxycyclopentan-r-1-ol (cf. Reference Example 4) (12 g) and 2,4-dichloroquinazoline (11.8 g) in dioxane (100 ml) is added potassium t-butoxide (6.7 g) with stirring under ice-cooling, and the mixture is stirred under ice-cooling for 70 minutes. The reaction mixture is diluted with ethyl acetate, and washed with water. The ethyl acetate solution is dried over anhydrous magnesium sulfate and evaporated to dryness under reduced pressure. The resulting residue is briefly purified with medium pressure column chromatography (eluent, chloroform:methanol=100:1, 50:1, v/v) to give an oily substance. The oily substance is dissolved in dioxane (20 ml) and the solution is slowly added dropwise to a solution of piperazine (13.6 g) in dioxane (50 ml) with stirring at 70° C., and the mixture is stirred at the same temperature for one hour. The reaction mixture is poured into water, and extracted with ethyl acetate. The extract is washed with water, dried over anhydrous sodium sulfate, and evaporated to dryness under reduced pressure. The resulting residue is purified by medium pressure liquid column chromatography (eluent, chloroform:methanol=50:1, 20:1, v/v) to give 4-[(t-3,t-4-diacetoxycyclopentan-r-1-yl)oxy]-2-(1-piperazinyl)quinazoline (8.2 g) as crystals.

NMR (300 MHz, CDCl$_3$, δppm): 1.80 (1H, s), 2.08 (6H, s), 2.3–2.5 (4H, m), 2.96 (4H, m), 3.88 (4H, m), 5.47 (2H, m), 5.72 (1H, m), 7.13 (1H, ddd, J=1, 7, 8 Hz), 7.48 (1H, dt, J=1, 8.5 Hz), 7.59 (1H, ddd, J=1.5, 7, 8.5 Hz), 7.86 (1H, ddd, J=0.5, 1.5, 8 Hz)

(2) 2-[4-(Benzyloxycarbonyl)piperazin-1-yl]-4-[(t-3,t-4-diacetoxycyclopentan-r-1-yl)oxy]quinazoline:

To a solution of 4-[(t-3,t-4-diacetoxycyclopentan-r-1-yl)oxy]-2-(1-piperazinyl)quinazoline (4.00 g) in dry methylene chloride (40 ml) is added triethylamine (2.69 ml) with stirring under ice-cooling, and thereto is further added dropwise a solution of benzyl chlorocarbonate (1.52 ml) in dry methylene chloride (7 ml). The mixture is stirred under ice-cooling for 30 minutes, and the reaction mixture is evaporated to dryness under reduced pressure, and thereto is added ethyl acetate, and the mixture is washed with water, diluted hydrochloric acid, water and saturated saline solution in this order. The ethyl acetate solution is dried over anhydrous magnesium sulfate, and evaporated to dryness under reduced pressure. The residue is purified by medium pressure liquid column chromatography (eluent, chloroform) to give 2-[4-(benzyloxycarbonyl)piperazin-1-yl]-4-[(t-3,t-4-diacetoxycyclopentan-r-1-yl)oxy]quinazoline (5.48 g) as crystals.

NMR (300 MHz, CDCl$_3$, δppm): 2.08 (6H, s), 2.3–2.5 (4H, m), 3.61 (4H, m), 3.91 (4H, m), 5.18 (2H, s), 5.47 (2H, m), 5.71 (1H, m), 7.16 (1H, ddd, J=1, 7, 8 Hz), 7.3–7.4 (5H, m), 7.49 (1H, dd, J=1, 8.5 Hz), 7.61 (1H, ddd, J=1.5, 7, 8.5 Hz), 7.87 (1H, ddd, J=0.5, 1.5, 8 Hz)

(3) 2-[4-(Benzyloxycarbonyl)piperazin-1-yl]-4-[(t-3,t-4-dihydroxycyclopentan-r-1-yl)oxy]quinazoline:

To a solution of 2-[4-(benzyloxycarbonyl)piperazin-1-yl]-4-[(t-3,t-4-diacetoxycyclopentan-r-1-yl)oxy]quinazoline (7.7 g) in methanol (100 ml) is added potassium carbonate (5.5 g), and the mixture is stirred at room temperature for one hour. The reaction mixture is filtered, and the filtrate is extracted with chloroform to isolate the produced crystals, and the extract is washed with water, dried over anhydrous sodium sulfate and evaporated to dryness under reduced pressure. The resulting residue is purified by medium pressure liquid column chromatography (eluent, chloroform:methanol=100:1, v/v) to give 2-[4-(benzyloxycarbonyl)piperazin-1-yl]-4-[(t-3,t-4-dihydroxycyclopentan-r-1-yl)oxy]quinazoline (6.0 g).

NMR (300 MHz, CDCl$_3$, δppm): 2.1–2.3 (2H, m), 2.3–2.5 (2H, m), 2.51 (2H, br), 3.61 (4H, m), 3.91 (4H, br), 4.36 (2H, m), 5.18 (2H, s), 5.70 (1H, m), 7.14 (1H, ddd, J=1, 7, 8 Hz), 7.3–7.4 (5H, m), 7.49 (1H, d, J=8.5 Hz), 7.59 (1H, ddd, J=1.5, 7, 8.5 Hz), 7.86 (1H, ddd, J=0.5, 1.5, 8 Hz)

(4) 4-[(t-3,t-4-Dihydroxycyclopentan-r-1-yl)oxy]-2-(1-piperazinyl)quinazoline:

To a solution of 2-[4-(benzyloxycarbonyl)piperazin-1-yl]-4-[(t-3,t-4-dihydroxycyclopentan-r-1-yl)oxy]quinazoline (3.21 g) in methanol (73 ml) is added 10% palladium/carbon (640 mg), and the mixture is stirred under hydrogen atmosphere and under atmospheric pressure at room temperature for 15 hours. The reaction mixture is filtered, and the filtrate is evaporated to dryness under reduced pressure, and the resulting residue is washed with acetone to give 4-[(t-3,t-4-dihydroxycyclopentan-r-1-yl)-oxy]-2-(1-piperazinyl)-quinazoline (1.90 g) as crystals. A part of the product is recrystallized from methanol to give a product having the following physical properties.

M.p.: 205–208° C.

NMR (300 MHz, DMSO-$d_6$, δppm): 1.9–2.0 (2H, m), 2.1–2.3 (2H, m), 2.76 (4H, m), 3.33 (1H, br), 3.75 (4H, m), 4.08 (2H, br), 4.60 (2H, br), 5.57 (1H, m), 7.14 (1H, ddd, J=1, 7, 8 Hz), 7.38 (1H, d, J=8.5 Hz), 7.62 (1H, ddd, J=1.5, 7, 8.5 Hz), 7.82 (1H, dd, J=1.5, 8 Hz)

Elementary analysis for $C_{17}H_{22}N_4O_3$:
Calcd. (%): C,61.80; H,6.71; N,16.96
Found (%): C,61.70; H,6.77; N,16.84

Example 27

4-[(t-3,t-4-Dihydroxycyclopentan-r-1-yl)oxy]-2-(1-piperazinyl)quinazoline monohydrochloride:

4-[(t-3,t-4-Dihydroxycyclopentan-r-1-yl)oxy]-2-(1-piperazinyl)quinazoline (cf. Example 26) (1.70 g) is dissolved in methanol (75 ml) with heating, and thereto is added 2N HCl-methanol (2.7 ml), and the mixture is treated with active charcoal, and concentrated to a volume of about 50 ml under reduced pressure. To the mixture is added acetone (40 ml), and the mixture is allowed to stand at room temperature. The precipitated crystals are separated by filtration to give 4-[(t-3,t-4-dihydroxycyclopentan-r-1-yl)

oxy]-2-(1-piperazinyl) quinazoline monohydrochloride (1.29 g) as crystals.

M.p.: around 235° C. (dec.)

NMR (300 MHz, DMSO-$d_6$, δppm): 1.9–2.1 (2H, m), 2.1–2.3 (2H, m), 3.19 (4H, m), 4.0–4.2 (6H, m), 4.63 (2H, d, J=4 Hz), 5.60 (1H, m), 7.24 (1H, ddd, J=1, 7, 8 Hz), 7.46 (1H, d, J=8.5 Hz), 7.69 (1H, ddd, J=1.5, 7, 8.5 Hz), 7.88 (1H, dd, J=1.5, 8 Hz), 9.32 (2H, br)

Elementary analysis for $C_{17}H_{22}N_4O_3 \cdot HCl$:

Calcd. (%): C,55.66; H,6.32; N,15.27

Found (%): C,55.40; H,6.34; N,15.24

Example 28

4-[(t-3,t-4-Dihydroxycyclopentan-r-1-yl)oxy]-2-(1-piperazinyl)quinazoline ½ fumarate:

To a solution of 4-[(t-3,t-4-dihydroxycyclopentan-r-1-yl)oxy]-2-(1-piperazinyl)quinazoline (cf. Example 26) (0.2 g) in ethanol (20 ml) is added fumaric acid (70 mg), and the mixture is stirred at room temperature for one hour and evaporated to dryness under reduced pressure. The resulting residue is recrystallized from ethanol-water to give 4-[(t-3,t-4-dihydroxycyclopentan-r-1-yl)oxy]-2-(1-piperazinyl)quinazoline ½ fumarate (70 mg) as crystals.

M.p.: around 235° C. (dec.)

NMR (300 MHz, DMSO-$d_6$, δppm): 1.9–2.0 (2H, m), 2.1–2.3 (2H, m), 2.92 (4H, m), 3.0–4.0 (4H, br), 3.85 (4H, m), 4.06 (2H, m), 5.58 (1H, m), 6.45 (1H, s), 7.18 (1H, ddd, J=1, 7, 8 Hz), 7.40 (1H, d, J=8.5 Hz), 7.65 (1H, ddd, J=1.5, 7, 8.5 Hz), 7.84 (1H, dd, J=1.5, 8 Hz)

Elementary analysis for $C_{19}H_{24}N_4O_5$:

Calcd. (%): C,58.75; H,6.23; N,14.42

Found (%): C,58.66; H,6.29; N,14.35

Example 29

4-[(c-3,c-4-Dihydroxycyclopentan-r-1-yl)oxy]-2-(1-piperazinyl)quinazoline:

(1) 4-[(3,4-O-Isopropylidene-c-3,c-4-dihydroxycyclopentan-r-1-yl)oxy]-2-(1-piperazinyl)quinazoline:

To a solution of 1,2-O-isopropylidene-r-1,c-2,c-4-cyclopentanetriol (cf. Reference Example 6) (6.50 g) and 2,4-dichloroquinazoline (8.18 g) in tetrahydrofuran (80 ml) is added potassium t-butoxide (5.54 g) with stirring under ice-cooling, and the mixture is stirred under ice-cooling for 2 hours and 20 minutes. The reaction mixture is diluted with ethyl acetate, and washed with water. The ethyl acetate solution is dried over anhydrous magnesium sulfate and evaporated to dryness under reduced pressure. The resulting residue is briefly purified with medium pressure column chromatography (eluent, chloroform) to give a crystalline substance. The crystalline substance is added to a solution of piperazine (13.43 g) in dioxane (100 ml) with stirring at 50° C., and the mixture is stirred at the same temperature for 75 minutes. The reaction mixture is diluted with ethyl acetate and washed with water. The ethyl acetate solution is dried over anhydrous magnesium sulfate and evaporated to dryness under reduced pressure, and the resulting residue is purified by medium pressure liquid column chromatography (eluent, chloroform:methanol=10:1, 5:1, v/v) to give 4-[(3,4-O-isopropylidene-c-3,c-4-dihydroxycyclopentan-r-1-yl)oxy]-2-(1-piperazinyl)quinazoline (10.23 g) as crystals.

NMR (300 MHz, CDCl$_3$, δppm): 1.32 (3H, s), 1.50 (3H, s), 1.80 (1H, s), 2.0–2.2 (2H, m), 2.52 (2H, dd, J=1.5, 15.5 Hz), 2.94 (4H, m), 3.88 (4H, m), 4.80 (2H, m), 5.51 (1H, m), 7.10 (1H, ddd, J=1, 7, 8 Hz), 7.47 (1H, dt, J=1, 8.5 Hz), 7.56 (1H, ddd, J=1.5, 7, 8.5 Hz), 7.98 (1H, dd, J=1.5, 8 Hz)

(2) 2-[4-(Benzyloxycarbonyl)piperazin-1-yl]-4-[(3,4-O-isopropylidene-c-3,c-4-dihydroxycyclopentan-r-1-yl)oxy]quinazoline:

To a solution of 4-[(3,4-O-isopropylidene-c-3,c-4-dihydroxycyclopentan-r-1-yl)oxy]-2-(1-piperazinyl)quinazoline (8.99 g) in dry methylene chloride (80 ml) is added triethylamine (6.8 ml) with stirring under ice-cooling, and thereto is further added dropwise a solution of benzyl chlorocarbonate (3.65 ml) in dry methylene chloride (10 ml). The mixture is stirred under ice-cooling for 95 minutes, and to the reaction mixture is added chloroform, and the mixture is washed with water. The resulting solution is dried over anhydrous magnesium sulfate, and evaporated to dryness under reduced pressure, and the residue is washed with ethanol to give 2-[4-(benzyloxycarbonyl)piperazin-1-yl]-4-[(3,4-O-isopropylidene-c-3,c-4-dihydroxycyclopentan-r-1-yl)oxy]quinazoline (11.03 g) as crystals.

NMR (300 MHz, CDCl$_3$, δppm): 1.32 (3H, s), 1.49 (3H, s), 2.0–2.2 (2H, m), 2.51 (2H, dd, J=1, 15.5 Hz), 3.60 (4H, m), 3.91 (4H, m), 4.81 (2H, m), 5.18 (2H, s), 5.50 (1H, t, J=5.5 Hz), 7.13 (1H, ddd, J=1, 7, 8 Hz), 7.3–7.4 (5H, m), 7.48 (1H, dd, J=1, 8.5 Hz), 7.58 (1H, ddd, J=1.5, 7, 8.5 Hz), 7.99 (1H, ddd, J=0.5, 1.5, 8 Hz)

(3) 2-[4-(Benzyloxycarbonyl)piperazin-1-yl]-4-[(c-3,c-4-dihydroxycyclopentan-r-1-yl)oxy]quinazoline:

A mixture of 2-[4-(benzyloxycarbonyl)piperazin-1-yl]-4-[(3,4-O-isopropylidene-c-3,c-4-dihydroxycyclopentan-r-1-yl)oxy]quinazoline (10.4 g) in acetic acid (40 ml)-water (10 ml) is stirred at 60° C. for 30 hours. The reaction mixture is diluted with ethyl acetate, and the mixture is washed with water, aqueous sodium carbonate, and water, and then dried over anhydrous magnesium sulfate. The ethyl acetate solution is evaporated to dryness under reduced pressure, and the resulting residue is purified by medium pressure liquid column chromatography (eluent, chloroform:methanol= 100:1, 50:1, v/v) to give 2-[4-(benzyloxycarbonyl)piperazin-1-yl]-4-[(c-3,c-4-dihydroxycyclopentan-r-1-yl)oxy]quinazoline (4.83 g) as crystals.

NMR (300 MHz, CDCl$_3$, δppm): 2.10 (2H, dt, J=5, 14.5 Hz), 2.4–2.6 (2H, m), 2.78 (2H, br), 3.60 (4H, m), 3.89 (4H, br), 4.13 (2H, m), 5.17 (2H, s), 5.45 (1H, m), 7.14 (1H, ddd, J=1, 7, 8 Hz), 7.3–7.4 (5H, m), 7.48 (1H, dd, J=1, 8.5 Hz), 7.58 (1H, ddd, J=1.5, 7, 8.5 Hz), 7.91 (1H, ddd, J=0.5, 1.5, 8 Hz)

(4) 4-[(c-3,c-4-Dihydroxycyclopentan-r-1-yl)oxy]-2-(1-piperazinyl)quinazoline:

To a solution of 2-[4-(benzyloxycarbonyl)piperazin-1-yl]-4-[(c-3,c-4-dihydroxycyclopentan-r-1-yl)oxy]quinazoline (2.14 g) in methanol (50 ml)-dioxane (40 ml) is added 10% palladium/carbon (321 mg), and the mixture is stirred under hydrogen atmosphere and under atmospheric pressure at room temperature for 16.5 hours. The reaction mixture is filtered, and the filtrate is evaporated to dryness under reduced pressure, and the resulting residue is crystallized from acetone to give 4-[(c-3,c-4-dihydroxycyclopentan-r-1-yl)oxy]-2-(1-piperazinyl)quinazoline (1.20 g) as crystals.

NMR (300 MHz, DMSO-$d_6$, δppm): 1.87 (2H, dt, J=5.5, 14 Hz), 2.3–2.5 (2H, m), 2.81 (4H, m), 3.45 (1H, br), 3.78 (4H, m), 3.86 (2H, m), 4.54 (2H, br), 5.35 (1H, m), 7.16 (1H, ddd, J=1, 7, 8 Hz), 7.39 (1H, d, J=8.5 Hz), 7.63 (1H, ddd, J=1.5, 7, 8.5 Hz), 7.84 (1H, dd, J=1.5, 8 Hz)

EXAMPLE 30

4-[(c-3,c-4-Dihydroxycyclopentan-r-1-yl)oxy]-2-(1-piperazinyl)quinazoline monohydrochloride:

4-[(c-3,c-4-Dihydroxycyclopentan-r-1-yl)oxy]-2-(1-piperazinyl)quinazoline (cf. Example 29) (1.10 g) is dissolved in methanol, and thereto is added 2N HCl-methanol (1.83 ml), and the mixture is evaporated to dryness under reduced pressure, and the residue is washed with acetone. The resulting crystals are recrystallized from methanol to give 4-[(c-3,c-4-dihydroxycyclopentan-r-1-yl)oxy]-2-(1-piperazinyl)quinazoline monohydrochloride (697 mg) as crystals.

M.p.: around 230° C. (dec.) NMR (300 MHz, DMSO-$d_6$, δppm): 1.89 (2H, dt, J=5.5, 14 Hz), 2.3–2.5 (2H, m), 3.18 (4H, m), 3.87 (2H, br), 4.07 (4H, m), 4.65 (2H, d, J=3.5 Hz), 5.38 (1H, m), 7.25 (1H, ddd, J=1, 7, 8 Hz), 7.47 (1H, d, J=8.5 Hz), 7.69 (1H, ddd, J=1.5, 7, 8.5 Hz), 7.89 (1H, dd, J=1.5, 8 Hz), 9.51 (2H, br) Elementary analysis for $C_{17}H_{22}N_4O_3 \cdot HCl$: Calcd. (%): C,55.66; H,6.32; N,15.27 Found (%): C,55.76; H,6.37; N, 15.40

EXAMPLE 31

4-[(t-2,t-3,c-4-Trihydroxycyclopentan-r-1-yl)oxy]-2-(1-piperazinyl)quinazoline:

(1) 4-[(c-4-Hydroxycyclopent-2-en-r-1-yl)oxy]-2-(1-piperazinyl) quinazoline:

To a solution of cis-4-cyclopenten-1,3-diol [manufactured by Fluka Co., cf. Synthesis, 876 (1974)] (820 mg) and 2,4-dichloroquinazoline (1.63 g) in dimethylformamide is added 60% sodium hydride (in oil) (393 mg) with stirring at room temperature, and the mixture is stirred at room temperature for 3 hours. The reaction mixture is diluted with ethyl acetate, and washed with water 5 times. The ethyl acetate solution is dried over anhydrous magnesium sulfate and evaporated to dryness under reduced pressure. The resulting residue is dissolved in dioxane (10 ml) and the solution is added dropwise to a solution of piperazine (3.5 g) in dioxane (10 ml) with stirring at 70° C., and the mixture is stirred at the same temperature for 2 hours. The reaction mixture is diluted with ethyl acetate, washed with water, dried over anhydrous magnesium sulfate, and evaporated to dryness under reduced pressure. The resulting residue is purified by medium pressure liquid column chromatography (eluent, chloroform: methanol=10:1, 5:1, v/v) to give 4-[(c-4-hydroxycyclopent-2-en-r-1-yl)oxy]-2-(1-piperazinyl) quinazoline (1.38 g) as crystals.

NMR (300 MHz, DMSO-$d_6$, δppm): 1.66 (1H, dt, J=5, 13.5 Hz), 2.78 (4H, m), 2.97 (1H, dt, J=7.5, 13.5 Hz), 3.23 (1H, br), 3.76 (4H, m), 4.65 (1H, m), 5.19 (1H, br), 5.89 (1H, m), 6.12 (2H, m), 7.16 (1H, ddd, J=1, 7, 8 Hz), 7.40 (1H, d, J=8.5 Hz), 7.63 (1H, ddd, J=1.5, 7, 8.5 Hz), 7.83 (1H, dd, J=1.5, 8 Hz)

(2) 2-[4-(Benzyloxycarbonyl)piperazin-1-yl]-4-[(c-4-hydroxycyclopent-2-en-r-1-yl)oxy]quinazoline:

To a solution of 4-[(c-4-hydroxycyclopent-2-en-r-1-yl)oxy]-2-(1-piperazinyl) quinazoline (1.30 g) in dry methylene chloride (30 ml) is added triethylamine (1.16 ml) with stirring under ice-cooling, and thereto is further added dropwise a solution of benzyl chlorocarbonate (0.73 ml) in dry methylene chloride (6 ml). The mixture is stirred for 14 hours under ice-cooling, and the reaction mixture is diluted with chloroform and washed with water, and then dried over anhydrous magnesium sulfate. The resulting solution is evaporated to dryness under reduced pressure, and the residue is purified by medium pressure liquid column chromatography [eluent, chloroform, (chloroform:methanol= 100:1, v/v)] to give 2-[4-(benzyloxycarbonyl)piperazin-1-yl]-4-[(c-4hydroxycyclopent-2-en-r-1-yl)oxy]quinazoline (1.02 g) as crystals.

NMR (300 MHz, CDCl$_3$, δppm): 1.7–2.0 (1H, br), 1.89 (1H, dt, J=4, 14.5 Hz), 3.00 (1H, dt, J=7.5, 14.5 Hz), 3.62 (4H, m), 3.92 (4H, m), 4.82 (1H, br), 5.18 (2H, s), 5.96 (1H, m), 6.22 (2H, m), 7.14 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.91 (1H, ddd, J=0.5, 1.5, 8 Hz)

(3) 2-[4-(Benzyloxycarbonyl)piperazin-1-yl]-4-[(t-2,t-3, c-4-trihydroxycyclopentan-r-1-yl)oxy]quinazoline:

A mixture of 2-[4-(benzyloxycarbonyl)piperazin-1-yl]-4-[(c-4-hydroxycyclopent-2-en-r-1-yl)oxy]quinazoline (1.02 g), a solution of osmium tetroxide in t-butanol (osmium tetroxide 106 mg/t-butanol 8.36 g) (458 mg) and 4-methylmorpholine N-oxide (281 mg) in water (2 ml)—acetone (20 ml) is stirred at room temperature for 5 hours. Acetone is distilled off from the reaction mixture under reduced pressure, and to the resultant product is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=50:1, v/v) to give 2-[4-(benzyloxycarbonyl)piperazin-1-yl]-4-[(t-2,t-3,c-4-trihydroxycyclopentan-r-1-yl)oxy]quinazoline (736 mg) as foam.

NMR (300 MHz, CDCl$_3$, δppm): 1.65 (1H, br), 1.92 (1H, dt, J=5.5, 14.5 Hz), 2.22 (1H, br), 2.86 (1H, ddd, J=7, 8.5, 14.5 Hz), 2.96 (1H, br), 3.61 (4H, m), 3.88 (4H, br), 4.10 (1H, t, J=4.5 Hz), 4.2–4.4 (1H, m), 4.40 (1H, t, J=5 Hz), 5.17 (2H, s), 5.41 (1H, ddd, J=4.5, 5.5, 8.5 Hz), 7.17 (1H, ddd, J=1, 7, 8 Hz), 7.3–7.4 (5H, m), 7.50 (1H, d, J=8.5 Hz), 7.62 (1H, ddd, J=1.5, 7, 8.5 Hz), 7.91 (1H, dd, J=1.5, 8 Hz)

(4) 4-[(t-2,t-3,c-4-Trihydroxycyclopentan-r-1-yl)oxy]-2-(1-piperazinyl)quinazoline:

To a solution of 2-[4-(benzyloxycarbonyl)piperazin-1-yl]-4-[(t-2,t-3,c-4-trihydroxycyclopentan-r-1-yl)oxy] quinazoline (710 mg) in methanol is added 10% palladium/carbon (142 mg), and the mixture is stirred under hydrogen atmosphere and under atmospheric pressure at room temperature for 3.25 hours. The reaction mixture is filtered, and the filtrate is evaporated to dryness under reduced pressure to give 4-[(t-2,t-3,c-4-trihydroxycyclopentan-r-1-yl)oxy]-2-(1-piperazinyl)quinazoline (483 mg) as foam.

NMR (300 MHz, DMSO-$d_6$-$D_2O$, δppm): 1.46 (1H, dt, J=4.5, 14.5 Hz), 2.7–2.9 (5H, m), 3.7–3.9 (5H, m), 3.98 (1H, m), 4.34 (1H, t, J=5 Hz), 5.26 (1H, dt, J=5, 8.5 Hz), 7.24 (1H, ddd, J=1, 7, 8 Hz), 7.46 (1H, d, J=8.5 Hz), 7.69 (1H, ddd, J=1.5, 7, 8.5 Hz), 7.93 (1H, dd, J=1.5, 8 Hz)

EXAMPLE 32

4-[(t-2,t-3,c-4-Trihydroxycyclopentan-r-1-yl)oxy]-2-(1-piperazinyl)quinazoline ½ fumarate:

4-[(t-2,t-3,c-4-Trihydroxycyclopentan-r-1-yl)oxy]-2-(1-piperazinyl)quinazoline (cf. Example 31) (443 mg) is dissolved in ethanol (25 ml), and the solution is filtered, and to the filtrate is added fumaric acid (155 mg), and the mixture is stirred at room temperature. The precipitated crystals are separated by filtration to give a crystalline product (417 mg). To the crystalline product is added fumaric acid (57 ml) and dissolved by adding water (6 ml). The mixture is filtered, and the filtrate is concentrated until about 2 ml. To the concentrated mixture is added ethanol (13 ml), and the mixture is allowed to stand at room temperature. The precipitated recrystals are separated by filtration to give 4-[(t-2,t-3,c-4-trihydroxycyclopentan-r-1-yl)oxy]-2-(1-piperazinyl)quinazoline½ fumarate (313 mg) as crystals.

M.p.: around 221° C. (dec.) NMR (300 MHz, DMSO-$d_6$, δppm): 1.42 (1H, dt, J=4, 14.5 Hz), 2.74 (1H, m), 2.98 (4H, m), 3.75 (1H, t, J=4 Hz), 3.8–4.0 (5H, m), 4.29 (1H, t, J=5 Hz), 5.23 (1H, dt, J=5, 8.5 Hz), 4.5–6.0 (5H, br), 6.45 (1H, s), 7.22 (1H, ddd, J=1, 7, 8 Hz), 7.43 (1H, d, J=8.5 Hz), 7.67 (1H, ddd, J=1.5, 7, 8.5 Hz), 7.90 (1H, dd, J=1.5, 8 Hz) Elementary analysis for $C_{19}H_{24}N_4O_6$ ¼$H_2O$: Calcd. (%): C,55.81; H,6.04; N,13.70 Found (%): C,56.03; H,6.09; N,13.58

EXAMPLE 33

4-[(1S,2S,3S,4R)-(2,3,4-Trihydroxycyclopentan-1-yl)oxy]-2-(1-piperazinyl)quinazoline:

(1) 4-[(1S,4R)-(4-Acetoxycyclopent-2-en-1-yl)oxy]-2-(1-piperazinyl) quinazoline:

To a solution of (1S,4R)-4-acetoxycyclopent-2-en-1-ol [manufactured by Fluka Co., cf. Tetrahedron, 46, 3155 (1990)] (2.00 g) and 2,4-dichloroquinazoline (2.80 g) in tetrahydrofuran (52 ml) is added potassium t-butoxide (1.90 g) with stirring under ice-cooling, and the mixture is stirred under ice-cooling for 70 minutes. The reaction mixture is diluted with ethyl acetate, and washed with water. The ethyl acetate solution is dried over anhydrous magnesium sulfate and evaporated to dryness under reduced pressure. The resulting residue is briefly purified with medium pressure column chromatography (eluent, chloroform) to give an oily substance. The oily substance is dissolved in dioxane (16 ml), and the solution is added dropwise to a solution of piperazine (3.25 g) in dioxane (19 ml) with stirring at 50° C., and the mixture is stirred at the same temperature for 1.5 hour. The reaction mixture is diluted with ethyl acetate and washed with water. The ethyl acetate solution is dried over anhydrous magnesium sulfate and evaporated to dryness under reduced pressure, and the resulting residue is purified by medium pressure liquid column chromatography (eluent, chloroform:methanol=10:1, v/v) to give 4-[(1S,4R)-(4-acetoxycyclopent-2-en-1-yl)oxy]-2-(1-piperazinyl)quinazoline (2.12 g) as oil.

NMR (300 MHz, CDCl$_3$, δppm): 1.80 (1H, s), 1.98 (1H, dt, J=4, 15 Hz), 2.08 (3H, s), 2.96 (4H, m), 3.11 (1H, dt, J=7.5, 15 Hz), 3.89 (4H, m), 5.66 (1H, m), 6.00 (1H, m), 6.17 (1H, ddd, J=1, 2, 5.5 Hz), 6.34 (1H, ddd, J=1, 2, 5.5 Hz), 7.12 (1H, ddd, J=1, 7, 8 Hz), 7.49 (1H, dt, J=1, 8.5 Hz), 7.59 (1H, ddd, J=1.5, 7, 8.5 Hz), 7.91 (1H, ddd, J=0.5, 1.5, 8 Hz)

(2) 4-[(1S,4R)-(4-Acetoxycyclopent-2-en-1-yl)oxy]-2-[4-(benzyloxycarbonyl)piperazin-1-yl]quinazoline:

To a solution of 4-[(1S,4R)-(4-acetoxycyclopent-2-en-1-yl)oxy]-2-(1-piperazinyl)quinazoline (2.07 g) in dry methylene chloride (15 ml) is added triethylamine (1.63 ml) with stirring under ice-cooling, and thereto is further added dropwise a solution of benzyl chlorocarbonate (0.92 ml) in dry methylene chloride (5 ml). The mixture is stirred under ice-cooling for 2 hours, and the reaction mixture is diluted with chloroform, washed with water, and dried over anhydrous magnesium sulfate. The solution is evaporated to dryness under reduced pressure, and the residue is purified by medium pressure liquid column chromatography (eluent, chloroform) to give 4-[(1S,4R)-(4-acetoxycyclopent-2-en-1-yl)oxy]-2-[4-(benzyloxycarbonyl)piperazin-1-yl]quinazoline (2.36 g) as crystals.

NMR (300 MHz, CDCl$_3$, δppm): 1.98 (1H, dt, J=4, 15 Hz), 2.08 (3H, s), 3.09 (1H, dt, J=7.5, 15 Hz), 3.62 (4H, m), 3.92 (4H, m), 5.18 (2H, s), 5.66 (1H, m), 5.99 (1H, m), 6.18 (1H, ddd, J=1, 2, 5.5 Hz), 6.32 (1H, ddd, J=1.5, 2, 5.5 Hz), 7.15 (1H, ddd, J=1, 7, 8 Hz), 7.3–7.4 (5H, m), 7.50 (1H, d, J=8.5 Hz), 7.61 (1H, ddd, J=1.5, 7, 8.5 Hz), 7.93 (1H, dd, J=1.5, 8 Hz)

(3) 2-[4-(Benzyloxycarbonyl)piperazin-1-yl]-4-[(1S,4R)-(4-hydroxycyclopent-2-en-1-yl)oxy]quinazoline:

A solution of 4-[(1S,4R)-(4-acetoxycyclopent-2-en-1-yl)oxy]-2-[4-(benzyloxycarbonyl)piperazin-1-yl]quinazoline (2.30 g) and 2N aqueous sodium hydroxide (4.9 ml) in acetone (20 ml) is stirred at room temperature for 18 hours. Acetone is distilled off from the reaction mixture under reduced pressure, and thereto is added ethyl acetate, and the mixture is washed with water, and then dried over anhydrous magnesium sulfate. The solution is evaporated to dryness under reduced pressure, and the resulting residue is purified by medium pressure liquid column chromatography [eluent, chloroform, (chloroform:methanol=200 1, v/v)] to give 2-[4-(benzyloxycarbonyl)piperazin-1-yl]-4-[(1S,4R)-(4-hydroxycyclopent-2-en-1-yl)oxy]quinazoline (1.26 g) as crystals.

NMR (300 MHz, CDCl$_3$, δppm): 1.76 (1H, br), 1.89 (1H, dt, J=4, 14.5 Hz), 3.01 (1H, dt, J=7.5, 14.5 Hz), 3.61 (4H, m), 3.92 (4H, m), 4.82 (1H, br), 5.18 (2H, s), 5.96 (1H, m), 6.22 (2H, m), 7.15 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.91 (1H, ddd, J=0.5, 1.5, 8 Hz)

(4) 2-[4-(Benzyloxycarbonyl)piperazin-1-yl]-4-[(1S,2S,3S,4R)-(2,3,4-trihydroxycyclopentan-1-yl)oxy] quinazoline:

A mixture of 2-[4-(benzyloxycarbonyl)piperazin-1-yl]-4-[(1S,4R)-(4-hydroxycyclopent-2-en-1-yl)oxy]quinazoline (1.30 g), a solution of osmium tetroxide in t-butanol (osmium tetroxide 252 mg/t-butanol 18.1 g) (532 mg) and 4-methylmorpholine N-oxide (375 mg) in water (3 ml)—acetone (25 ml) is stirred at room temperature for 17 hours. Acetone is distilled off from the reaction mixture under reduced pressure, and to the resultant is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=50:1, 10:1, v/v) to give 2-[4-(benzyloxycarbonyl) piperazin-1-yl]-4-[(1S,2S,3S,4R)-(2,3,4-trihydroxycyclopentan-1-yl)oxy]quinazoline (1.05 mg) as foam.

NMR (300 MHz, CDCl$_3$, δppm): 1.71 (1H, br), 1.90 (1H, dt, J=5.5, 14.5 Hz), 2.41 (1H, br), 2.85 (1H, ddd, J=7, 8.5, 14.5 Hz), 3.08 (1H, br), 3.60 (4H, m), 3.88 (4H, br), 4.09 (1H, t, J=4.5 Hz), 4.2–4.4 (1H, m), 4.40 (1H, t, J=5 Hz), 5.17 (2H, s), 5.40 (1H, ddd, J=4.5, 5.5, 8.5 Hz), 7.15 (1H, ddd, J=1, 7, 8 Hz), 7.3–7.4 (5H, m), 7.50 (1H, dt, J=1, 8.5 Hz), 7.61 (1H, ddd, J=1.5, 7, 8.5 Hz), 7.90 (1H, dd, J=1.5, 8 Hz)

(5) 4-[(1S,2S,3S,4R)-(2,3,4-Trihydroxycyclopentan-1-yl)oxy]-2-(1-piperazinyl)quinazoline:

To a solution of 2-[4-(benzyloxycarbonyl)piperazin-1-yl]-4-[(1S,2S,3S,4R)-(2,3,4-trihydroxycyclopentan-1-yl)oxy] quinazoline (270 mg) in methanol (5 ml) is added 10% palladium/carbon (54 mg), and the mixture is stirred under hydrogen atmosphere and under atmospheric pressure at room temperature for 15 hours. The reaction mixture is filtered, and the filtrate is evaporated to dryness under reduced pressure to give 4-[(1S,2S,3S,4R)-(2,3,4- trihydroxycyclopentan-1-yl)oxy]-2-(1-piperazinyl) quinazoline (180 mg) as foam.

NMR (300 MHz, DMSO-$d_6$-$D_2O$, δppm): 1.44 (1H, dt, J=4.5, 14.5 Hz), 2.7–2.9 (5H, m), 3.7–3.9 (5H, m), 3.95 (1H, m), 4.32 (1H, t, J=5 Hz), 5.25 (1H, dt, J=5, 8.5 Hz), 7.21 (1H, ddd, J=1, 7, 8 Hz), 7.44 (1H, d, J=8.5 Hz), 7.67 (1H, ddd, J=1.5, 7, 8.5 Hz), 7.91 (1H, dd, J=1.5, 8 Hz)

EXAMPLE 34

4-[(1S,2S,3S,4R)-(2,3,4-Trihydroxycyclopentan-1-yl) oxy]-2-(1-piperazinyl)quinazoline ½ fumarate:

To a solution of 2-[4-(benzyloxycarbonyl)piperazin-1-yl]-4-[(1S,2S,3S,4R)-(2,3,4-trihydroxycyclopentan-1-yl)oxy] quinazoline [cf. Example 33(4)] (1.00 g) in methanol (15 ml) is added 10% palladium/carbon (200 mg), and the mixture is stirred under hydrogen atmosphere and under atmospheric pressure at room temperature for 3 hours. The reaction mixture is filtered, and the filtrate is evaporated to dryness under reduced pressure, and the residue is dissolved in ethanol (35 ml) and thereto is added fumaric acid (242 mg). The precipitated crystals are dissolved by adding water to the mixture. The mixture is filtered and the filtrate is evaporated to dryness under reduced pressure, and the resulting residue is recrystallized from water-ethanol to give 4-[(1S,2S,3S,4R)-(2,3,4-trihydroxycyclopentan-1-yl)oxy]-2-(1-piperazinyl)quinazoline ½ fumarate (390 mg) as crystals.

M.p.: around 214° C. (dec.) NMR (300 MHz, DMSO-$d_6$, δppm): 1.42 (1H, dt, J=4, 14.5 Hz), 2.74 (1H, m), 2.95 (4H, m), 3.75 (1H, t, J=4 Hz), 3.8–4.0 (5H, m), 4.29 (1H, t, J=5 Hz), 5.23 (1H, dt, J=5, 8.5 Hz), 4.3–5.9 (5H, br), 6.45 (1H, s), 7.21 (1H, ddd, J=1, 7, 8 Hz), 7.43 (1H, d, J=8.5 Hz), 7.67 (1H, ddd, J=1.5, 7, 8.5 Hz), 7.90 (1H, dd, J=1.5, 8 Hz) Elementary analysis for $C_{19}H_{24}N_4O_6 \cdot ¾H_2O$: Calcd. (%): C,54.60; H,6.15; N,13.41 Found (%): C,54.74; H,6.11; N,13.36

EXAMPLE 35

4-[(1R,2R,3R,4S)-(2,3,4-Trihydroxycyclopentan-1 -yl) oxy]-2-(1-piperazinyl)quinazoline:

(1) 4-[(1R,4S)-[4-[(RS)-(Tetrahydropyran-2-yl) oxy] cyclopent-2-en-1-yl]oxy]-2-(1-piperazinyl) quinazoline:

To a solution of (1R,4S)-4-[(RS)-(tetrahydropyran-2-yl) oxy]cyclopent-2-en-1-ol [cf. J. Chem. Soc., Chem. Commun., 1298 (1986)] (7.00 g) and 2,4-dichloroquinazoline (6.64 g) in tetrahydrofuran (73 ml) is added potassium t-butoxide (5.26 g) with stirring under ice-cooling, and the mixture is stirred under ice-cooling for 40 minutes. The reaction mixture is diluted with ethyl acetate, and washed with water. The ethyl acetate solution is dried over anhydrous magnesium sulfate and evaporated to dryness under reduced pressure. The resulting residue is dissolved in dioxane (20 ml), and the solution is added dropwise to a solution of piperazine (12.10 g) in dioxane (50 ml) with stirring at 50° C., and the mixture is stirred at the same temperature for 30 minutes.

The reaction mixture is diluted with ethyl acetate and washed with water. The ethyl acetate solution is dried over anhydrous magnesium sulfate and evaporated to dryness under reduced pressure, and the resulting residue is purified by medium pressure liquid column chromatography (eluent, chloroform:methanol=10:1, 5:1, v/v) to give 4-[(1R,4S)-[4-[(RS)-(tetrahydropyran-2-yl)oxy]cyclopent-2-en-1-yl] oxy]-2-(1-piperazinyl) quinazoline (11.07 g) as oil.

NMR (300 MHz, CDCl$_3$, δppm): 1.5–2.1 (8H, m), 2.9–3.2 (5H, m), 3.5–3.6 (1H, m), 3.8–4.0 (5H, m), 4.7–4.9 (2H, m), 5.96 (1H, m), 6.22 (2H, m), 7.11 (1H, ddd, J=1, 7, 8 Hz), 7.48 (1H, dt, J=1, 8.5 Hz), 7.57 (1H, ddd, J=1.5, 7, 8.5 Hz), 7.91 (1H, ddd, J=0.5, 1.5, 8 Hz)

(2) 2-[4-(Benzyloxycarbonyl)piperazin-1-yl]-4-[(1R,4S)-[4-[(RS)-(tetrahydropyran-2-yl)oxy]cyclopent-2-en-1-yl] oxy]quinazoline:

To a solution of 4-[(1R,4S)-[4-[(RS)-(tetrahydropyran-2-yl)oxy]cyclopent-2-en-1-yl]oxy]-2-(1-piperazinyl) quinazoline (11.07 g) in dry methylene chloride (110 ml) is added triethylamine (7.75 ml) with stirring under ice-cooling, and thereto is further added dropwise a solution of benzyl chlorocarbonate (4.40 ml) in dry methylene chloride (20 ml). The mixture is stirred under ice-cooling for one hour. The reaction mixture is washed with water, and dried over anhydrous magnesium sulfate. The solution is evaporated to dryness under reduced pressure, and the residue is purified by medium pressure liquid column chromatography (eluent, chloroform) to give 2-[4-(benzyloxycarbonyl) piperazin-1-yl]-4-[(1R,4S)-[4-[(RS)-(tetrahydropyran-2-yl) oxy]cyclopent-2-en-1-yl]oxy]quinazoline (12.57 g) as oil.

NMR (300 MHz, CDCl$_3$, δppm): 1.5–2.1 (7H, m), 2.9–3.1 (1H, m), 3.5–3.7 (5H, m), 3.8–4.0 (5H, m), 4.7–4.9 (2H, m), 5.18 (2H, s), 5.95 (1H, m), 6.1–6.3 (2H, m), 7.14 (1H, ddd, J=1, 7, 8 Hz), 7.3–7.4 (5H, m), 7.49 (1H, dt, J=1, 8.5 Hz), 7.59 (1H, ddd, J=1.5, 7, 8.5 Hz), 7.93 (1H, dt, J=1.5, 8 Hz)

(3) 2-[4-(Benzyloxycarbonyl)piperazin-1-yl]-4-[(1R,4S)-(4-hydroxycyclopent-2-en-1-yl)oxy]quinazoline:

A solution of 2-[4-(benzyloxycarbonyl)piperazin-1-yl]-4-[(1R,4S)-[4-[(RS)-(tetrahydropyran-2-yl)oxy]cyclopent-2-en-1-yl]oxy]quinazoline (12.57 g) in acetic acid (50 ml)—water (12.6 ml) is stirred at 60° C. for 4.5 hours. The reaction mixture is diluted with ethyl acetate and washed with aqueous sodium hydrogen carbonate and water, and then dried over anhydrous magnesium sulfate. The solution is evaporated to dryness under reduced pressure, and the resulting residue is purified by medium pressure liquid column chromatography [eluent, chloroform, (chloroform:methanol=500:1, v/v)] to give 2-[4-(benzyloxycarbonyl) piperazin-1-yl]-4-[(1R,4S)-(4-hydroxycyclopent-2-en-1-yl) oxy] quinazoline (6.31 g) as crystals.

NMR (300 MHz, CDCl$_3$, δppm): 1.7–2.0 (1H, br), 1.88 (1H, dt, J=4, 14.5 Hz), 3.01 (1H, dt, J=7.5, 14.5 Hz), 3.61 (4H, m), 3.91 (4H, m), 4.82 (1H, br), 5.18 (2H, s), 5.96 (1H, m), 6.21 (2H, m), 7.14 (1H, ddd, J=1, 7, 8 Hz), 7.3–7.4 (5H, m), 7.49 (1H, dt, J=1, 8.5 Hz), 7.61 (1H, ddd, J=1.5, 7, 8.5 Hz), 7.91 (1H, ddd, J=0.5, 1.5, 8 Hz)

(4) 2-[4-(Benzyloxycarbonyl)piperazin-1-yl]-4-[(1R,2R, 3R,4S)-(2,3,4-trihydroxycyclopentan-1-yl)oxy]quinazoline:

A mixture of 2-[4-(benzyloxycarbonyl)piperazin-1-yl]-4-[(1R,4S)-(4-hydroxycyclopent-2-en-1-yl)oxy]quinazoline (1.00 g), a solution of osmium tetroxide in t-butanol (osmium tetroxide 252 mg/t-butanol 18.1 g) (409 mg) and 4-methylmorpholine N-oxide (281 mg) in water (2 ml)—acetone (20 ml) is stirred at room temperature for 8 hours. Acetone is distilled off from the reaction mixture under reduced pressure, and to the resultant is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=50:1, 10:1, v/v) to give 2-[4-(benzyloxycarbonyl)piperazin-1-yl]-4-[(1R,2R,3R,4S)-(2,3, 4-trihydroxycyclopentan-1-yl)oxy]quinazoline (954 mg) as foam.

NMR (300 MHz, CDCl$_3$, δppm): 1.7–2.0 (1H, br), 1.89 (1H, dt, J=5.5, 14.5 Hz), 2.60 (1H, br), 2.85 (1H, ddd, J=7, 8.5, 14.5 Hz), 3.21 (1H, br), 3.60 (4H, m), 3.87 (4H, br), 4.09 (1H, t, J=4.5 Hz), 4.2–4.4 (1H, m), 4.39 (1H, t, J=5 Hz), 5.16 (2H, s), 5.39 (1H, ddd, J=4.5, 5.5, 8.5 Hz), 7.14 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.89 (1H, dd, J=1.5, 8 Hz)

(5) 4-[(1R,2R,3R,4S)-(2,3,4-Trihydroxycyclopentan-1-yl)oxy]-2-(1-piperazinyl)quinazoline:

To a solution of 2-[4-(benzyloxycarbonyl)piperazin-1-yl]-4-[(1R,2R,3R,4S)-(2,3,4-trihydroxycyclopentan-1-yl)oxy]quinazoline (854 mg) in methanol (15 ml) is added 10% palladium/carbon (200 mg), and the mixture is stirred under hydrogen atmosphere and under atmospheric pressure at room temperature for 14.5 hours. The reaction mixture is filtered, and the filtrate is evaporated to dryness under reduced pressure to give 4-[(1R,2R,3R,4S)-(2,3,4-trihydroxycyclopentan-1-yl)oxy]-2-(1-piperazinyl)quinazoline (545 mg) as foam.

NMR (300 MHz, DMSO-d$_6$-D$_2$O, δppm): 1.46 (1H, dt, J=4.5, 14.5 Hz), 2.7–2.9 (5H, m), 3.7–3.9 (5H, m), 3.99 (1H, m), 4.34 (1H, t, J=5 Hz), 5.27 (1H, dt, J=5, 8.5 Hz), 7.24 (1H, ddd, J=1, 7, 8 Hz), 7.46 (1H, d, J=8.5 Hz), 7.69 (1H, ddd, J=1.5, 7, 8.5 Hz), 7.93 (1H, dd, J=1.5, 8 Hz)

EXAMPLE 36

4-[(1R,2R,3R,4S)-(2,3,4-Trihydroxycyclopentan-1-yl)oxy]-2-(1-piperazinyl)quinazoline ½ fumarate:

To a solution of 4-[(1R,2R,3R,4S)-(2,3,4-trihydroxycyclopentan-1-yl)oxy]-2-(1-piperazinyl)quinazoline [cf. Example 35] (520 mg) in ethanol (15 ml) is added fumaric acid (96 mg), and the mixture is stirred at room temperature for 15 minutes. The precipitated crystals are separated by filtration to give a crystalline product (478 mg). To the crystalline product is added fumaric acid (68 mg) and dissolved by adding water to the mixture. The mixture is filtered and the filtrate is concentrated until about 1 ml volume. To the concentrated product is added ethanol (10 ml), and the mixture is allowed to stand at room temperature, and the precipitated crystals are separated by filtration to give 4-[(1R,2R,3R,4S)-(2,3,4-trihydroxycyclopentan-1-yl)oxy]-2-(1-piperazinyl)quinazoline ½ fumarate (327 mg) as crystals.

M.p.: around 226° C. (dec.) NMR (300 MHz, DMSO-d$_6$, δppm): 1.41 (1H, dt, J=4, 14.5 Hz), 2.74 (1H, m), 2.95 (4H, m), 3.75 (1H, t, J=4 Hz), 3.8–4.0 (5H, m), 4.29 (1H, t, J=5 Hz), 4.86 (5H, br), 5.23 (1H, dt, J=5, 8.5 Hz), 6.45 (1H, s), 7.21 (1H, ddd, J=1, 7, 8 Hz), 7.43 (1H, d, J=8.5 Hz), 7.67 (1H, ddd, J=1.5, 7, 8.5 Hz), 7.89 (1H, dd, J=1.5, 8 Hz) Elementary analysis for C$_{19}$H$_{24}$N$_4$O$_6$: Calcd. (%): C,56.43; H,5.98; N,13.85 Found (%): C,56.20; H,5.91; N,13.75

EXAMPLE 37

4-[(1S,2S,3R,4R)-(2,3-Dihydroxy-4-methoxycyclopentan-1-yl)oxy]-2-(1-piperazinyl)quinazoline:

(1) 2-[4-(Benzyloxycarbonyl)piperazin-1-yl]-4 -[(1S,4R)-(4-methoxycyclopent-2-en-1-yl)oxy]quinazoline:

To a solution of 2-[4-(benzyloxycarbonyl)piperazin-1-yl]-4-[(1S,4R)-(4-hydroxycyclopent-2-en-1-yl)oxy]quinazoline [cf. Example 33(3)] (750 mg) and methyl iodide (445 mg) in dimethylformamide (6 ml) is added 60% sodium hydride (oil) (94 mg) with stirring at room temperature, and the mixture is stirred for 3 hours. The reaction mixture is diluted with ethyl acetate, and washed with water 5 times. The ethyl acetate solution is dried over anhydrous magnesium sulfate and evaporated to dryness under reduced pressure. The resulting residue is purified by medium pressure liquid column chromatography [eluent, chloroform, (chloroform:methanol=200:1, v/v)] to give 2-[4-(benzyloxycarbonyl)piperazin-1-yl]-4-[(1S,4R)-(4-methoxycyclopent-2-en-1-yl)oxy]quinazoline (710 mg) as oil.

NMR (300 MHz, CDCl$_3$, δppm): 1.92 (1H, dt, J=4.5, 14.5 Hz), 2.95 (1H, dt, J=7.5, 14.5 Hz), 3.40 (3H, s), 3.62 (4H, m), 3.92 (4H, m), 4.44 (1H, m), 5.18 (2H, s), 5.97 (1H, m), 6.24 (1H, d, J=6.5 Hz), 6.24 (1H, d, J=6.5 Hz), 7.14 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.92 (1H, dd, J=1.5, 8 Hz)

(2) 2-[4-(Benzyloxycarbonyl)piperazin-1-yl]-4-[(1S,2S,3R,4R)-(2,3-dihydroxy-4-methoxycyclopentan-1-yl)oxy]quinazoline:

A mixture of 2-[4-(benzyloxycarbonyl)piperazin-1-yl]-4-[(1S,4R)-(4-methoxycyclopent-2-en-1-yl)oxy]quinazoline (742 mg), a solution of osmium tetroxide in t-butanol (osmium tetroxide 252 mg/t-butanol 18.1 g) (316 mg) and 4-methylmorpholine N-oxide (222 mg) in water (1.4 ml)—acetone (14 ml) is stirred at room temperature for 14 hours. Acetone is distilled off from the reaction mixture under reduced pressure, and to the resultant is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=100:1, v/v) to give 2-[4-(benzyloxycarbonyl)piperazin-1-yl]-4-[(1S,2S,3R,4R)-(2,3-dihydroxy-4-methoxycyclopentan-1-yl)oxy]quinazoline (657 mg) as foam.

NMR (300 MHz, CDCl$_3$, δppm): 1.95 (1H, m), 2.83 (1H, m), 2.7–3.0 (1H, br), 3.41 (3H, s), 3.62 (4H, m), 3.80 (1H, m), 3.87 (4H, br), 4.19 (1H, m), 4.34 (1H, t, J=5.5 Hz), 4.2–4.5 (1H, br), 5.18 (2H, s), 5.44 (1H, dt, J=6, 8.5 Hz), 7.17 (1H, ddd, J=1, 7, 8Hz), 7.3–7.4 (5H, m), 7.50 (1H, d, J=8.5 Hz), 7.63 (1H, ddd, J=1.5, 7, 8.5 Hz), 7.92 (1H, ddd, J=0.5, 1.5, 8 Hz)

(3) 4-[(1S,2S,3R,4R)-(2,3-Dihydroxy-4-methoxycyclopentan-1-yl)oxy]-2-(1-piperazinyl)quinazoline:

To a solution of 2-[4-(benzyloxycarbonyl)piperazin-1-yl]-4-[(1S,2S,3R,4R)-(2,3-dihydroxy-4-methoxycyclopentan-1-yl)oxy]quinazoline (600 mg) in methanol (12 ml) is added 10% palladium/carbon (120 mg), and the mixture is stirred under hydrogen atmosphere and under atmospheric pressure at room temperature for 20 hours. The reaction mixture is filtered, and the filtrate is evaporated to dryness under reduced pressure to give 4-[(1S,2S,3R,4R)-(2,3-dihydroxy-4-methoxycyclopentan-1-yl)oxy]-2-(1-piperazinyl)quinazoline (415 mg) as foam.

NMR (300 MHz, CDCl$_3$, δppm): 1.93 (1H, dt, J=5.5, 14.5 Hz), 2.82 (1H, ddd, J=7, 8.5, 14.5 Hz), 2.97 (4H, m), 2.6–3.2 (3H, br), 3.41 (3H, s), 3.7–4.0 (5H, m), 4.17 (1H, m), 4.32 (1H, t, J=5 Hz), 5.44 (1H, dt, J=6, 8.5 Hz), 7.12 (1H, ddd, J=1, 7, 8 Hz), 7.48 (1H, d, J=8.5 Hz), 7.59 (1H, ddd, J=1.5, 7, 8.5 Hz), 7.88 (1H, ddd, J=0.5, 1.5, 8 Hz)

EXAMPLE 38

4-[(1S,2S,3R,4R)-(2,3-Dihydroxy-4-methoxycyclopentan-1-yl)oxy]-2-(1-piperazinyl)quinazoline ½ fumarate:

To a solution of 4-[(1S,2S,3R,4R)-(2,3-dihydroxy-4-methoxycyclopentan-1-yl)oxy]-2-(1-piperazinyl)quinazoline [cf. Example 37] (397 mg) in ethanol (4 ml) is added fumaric acid (68 mg), and the mixture is stirred at room temperature for 15 minutes. The precipitated crystals are separated by filtration, and the crystals are recrystallized from water-ethanol to give 4-[(1S,2S,3R,4R)-(2,3-dihydroxy-4-methoxycyclopentan-1-yl)oxy]-2-(1-piperazinyl)quinazoline ½ fumarate (318 mg) as crystals.

M.p.: 153–156° C. NMR (300 MHz, DMSO-$d_6$, δppm): 1.51 (1H, dt, J=4, 14.5 Hz), 2.75 (1H, dt, J=8, 14.5 Hz), 2.95 (4H, m), 3.26 (3H, s), 3.63 (1H, m), 3.88 (4H, m), 3.93 (1H, t, J=4 Hz), 4.16 (1H, t, J=5 Hz), 5.26 (1H, dt, J=5, 8.5 Hz), 4.5–6.2 (4H, br), 6.45 (1H, s), 7.21 (1H, ddd, J=1, 7, 8 Hz), 7.43 (1H, d, J=8.5 Hz), 7.67 (1H, ddd, J=1.5, 7, 8.5 Hz), 7.87 (1H, dd, J=1.5, 8 Hz) Elementary analysis for $C_{20}H_{26}N_4O_6 \cdot H_2O$: Calcd. (%): C,55.04; H,6.47; N,12.84 Found (%): C,55.18; H,6.45; N,12.54

EXAMPLE 39

4-[(1R,2R,3S,4S)-(2,3-Dihydroxy-4-methoxycyclopentan-1-yl)oxy]-2-(1-piperazinyl)quinazoline:

(1) 2-[4-(Benzyloxycarbonyl)piperazin-1-yl]-4-[(1R,4S)-(4-methoxycyclopent-2-en-1-yl)oxy]quinazoline:

To a solution of 2-[4-(benzyloxycarbonyl)piperazin-1-yl]-4-[(1R,4S)-(4-hydroxycyclopent-2-en-1-yl)oxy]quinazoline [cf. Example 35(3)] (6.31 g) and methyl iodide (4.00 g) in dimethylformamide (52 ml) is added 60% sodium hydride (in oil) (678 mg) with stirring under ice-cooling, and the mixture is stirred at room temperature for 4 hours. The reaction mixture is diluted with ethyl acetate, and washed with water 5 times. The ethyl acetate solution is dried over anhydrous magnesium sulfate and evaporated to dryness under reduced pressure. The resulting residue is purified by medium pressure liquid column chromatography (eluent, chloroform:methanol=500:1, v/v) to give 2-[4-(benzyloxycarbonyl)piperazin-1-yl]-4-[(1R,4S)-(4-methoxycyclopent-2-en-1-yl)oxy]quinazoline (5.92 g) as oil.

NMR (300 MHz, CDCl$_3$, δppm): 1.92 (1H, dt, J=4.5, 14.5 Hz), 2.95 (1H, dt, J=7.5, 14.5 Hz), 3.40 (3H, s), 3.62 (4H, m), 3.92 (4H, m), 4.44 (1H, m), 5.18 (2H, s), 5.97 (1H, m), 6.24 (1H, d, J=6.5 Hz), 6.24 (1H, d, J=6.5 Hz), 7.14 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.92 (1H, dd, J=1.5, 8 Hz)

(2) 2-[4-(Benzyloxycarbonyl)piperazin-1-yl]-4-[(1R,2R,3S,4S)-(2,3-dihydroxy-4-methoxycyclopentan-1-yl)oxy]quinazoline:

A mixture of 2-[4-(benzyloxycarbonyl)piperazin-1-yl]-4-[(1R,4S)-(4-methoxycyclopent-2-en-1-yl)oxy]quinazoline (5.92 g), a solution of osmium tetroxide in t-butanol (osmium tetroxide 252 mg/t-butanol 18.1 g) (2.53 g) and 4-methylmorpholine N-oxide (1.78 g) in water (11 ml)—acetone (110 ml) is stirred at room temperature for 18.5 hours. Acetone is distilled off from the reaction mixture under reduced pressure, and to the resultant is added ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=100:1, v/v) to give 2-[4-(benzyloxycarbonyl)piperazin-1-yl]-4-[(1R,2R,3S,4S)-(2,3-dihydroxy-4-methoxycyclopentan-1-yl)oxy]quinazoline (5.93 g) as crystals.

NMR (300 MHz, CDCl$_3$, δppm): 1.96 (1H, m), 2.80 (1H, br), 2.7–2.9 (1H, m), 3.41 (3H, s), 3.62 (4H, m), 3.80 (1H, m), 3.88 (4H, br), 4.19 (1H, m), 4.34 (1H, t, J=5.5 Hz), 4.2–4.5 (1H, br), 5.18 (2H, s), 5.45 (1H, dt, J=6, 8.5 Hz), 7.17 (1H, ddd, J=1, 7, 8 Hz), 7.3–7.4 (5H, m), 7.50 (1H, d, J=8.5 Hz), 7.63 (1H, ddd, J=1.5, 7, 8.5 Hz), 7.92 (1H, ddd, J=0.5, 1.5, 8 Hz)

(3) 4-[(1R,2R,3S,4S)-(2,3-Dihydroxy-4-methoxycyclopentan-1-yl)oxy]-2-(1-piperazinyl)quinazoline:

To a solution of 2-[4-(benzyloxycarbonyl)piperazin-1-yl]-4-[(1R,2R,3S,4S)-(2,3-dihydroxy-4-methoxycyclopentan-1-yl)oxy]quinazoline (5.40 g) in methanol (108 ml) is added 10% palladium/carbon (1.00 g), and the mixture is stirred under hydrogen atmosphere and under atmospheric pressure at room temperature for 16.5 hours. The reaction mixture is filtered, and the filtrate is evaporated to dryness under reduced pressure, and the residue is crystallized from diethyl ether to give 4-[(1R,2R,3S,4S)-(2,3-dihydroxy-4-methoxycyclopentan-1-yl)oxy]-2-(1-piperazinyl)quinazoline (2.95 g) as crystals. A part of this product is recrystallized from ethanol-diethyl ether to give a pure crystalline product, which has the following physical properties.

M.p.: 164–167° C. $[\alpha]_D^{20}$=−50° (c=1.0, methanol) NMR (300 MHz, CDCl$_3$, δppm): 1.94 (1H, dt, J=5.5, 14.5 Hz), 2.82 (1H, ddd, J=7, 8.5, 14.5 Hz), 2.96 (4H, m), 2.4–3.1 (3H, br), 3.41 (3H, s), 3.7–4.0 (5H, m), 4.17 (1H, m), 4.32 (1H, t, J=5 Hz), 5.44 (1H, dt, J=6, 8.5 Hz), 7.12 (1H, ddd, J=1, 7, 8 Hz), 7.48 (1H, d, J=8.5 Hz), 7.60 (1H, ddd, J=1.5, 7, 8.5 Hz), 7.88 (1H, ddd, J=0.5, 1.5, 8 Hz) Elementary analysis for $C_{18}H_{24}N_4O_4$: Calcd. (%): C,59.99; H,6.71; N,15.55 Found (%): C,59.80; H,6.74; N,15.36

EXAMPLE 40

4-[(1R,2R,3S,4S)-(2,3-Dihydroxy-4-methoxycyclopentan-1-yl)oxy]-2-(1-piperazinyl)quinazoline ½ fumarate:

To a solution of 4-[(1R,2R,3S,4S)-(2,3-dihydroxy-4-methoxycyclopentan-1-yl)oxy]-2-(1-piperazinyl)quinazoline [cf. Example 39] (550 mg) in ethanol (5.5 ml) is added fumaric acid (94 mg), and the mixture is stirred at room temperature for 10 minutes. The precipitated crystals are separated by filtration, and the crystals are recrystallized from water-ethanol to give 4-[(1R,2R,3S,4S)-(2,3-dihydroxy-4-methoxycyclopentan-1-yl)oxy]-2-(1-piperazinyl)quinazoline ½ fumarate (387 mg) as crystals.

M.p.: 154–158° C. NMR (300 MHz, DMSO-$d_6$, δppm): 1.51 (1H, dt, J=4, 14.5 Hz), 2.75 (1H, dt, J=8, 14.5 Hz), 2.95 (4H, m), 3.25 (3H, s), 3.63 (1H, dt, J=3.5, 7.5 Hz), 3.88 (4H, m), 3.93 (1H, t, J=4 Hz), 4.16 (1H, t, J=5 Hz), 5.26 (1H, dt, J=5, 8.5 Hz), 4.4–5.6 (4H, br), 6.45 (1H, s), 7.21 (1H, ddd, J=1, 7, 8 Hz), 7.43 (1H, d, J=8.5 Hz), 7.66 (1H, ddd, J=1.5, 7, 8.5 Hz), 7.87 (1H, dd, J=1.5, 8 Hz) Elementary analysis for $C_{20}H_{26}N_4O_6 \cdot H_2O$: Calcd. (%): C,55.04; H,6.47; N,12.85 Found (%): C,55.16; H,6.41; N,12.66

EXAMPLE 41

4-[(1R,2R,3S,4S)-(2,3-Dihydroxy-4-methoxycyclopentan-1-yl)oxy]-2-(1-piperazinyl)quinazoline monohydrochloride:

4-[(1R,2R,3S,4S)-(2,3-Dihydroxy-4-methoxycyclopentan-1-yl)oxy]-2-(1-piperazinyl)quinazoline [cf. Example 39] (2.60 g) is dissolved in methanol (35 ml) with heating, and the solution is filtered, and to the filtrate is added 2N HCl-methanol (4.0 ml), and the mixture is concentrated until about 25 ml volume under reduced pressure. To the mixture is added acetone (100 ml) and the mixture is allowed to stand at room temperature. The precipitated crystals are separated by filtration and dried in the presence of phosphorus pentoxide at room temperature to give 4-[(1R,2R,3S,4S)-(2,3-dihydroxy-4-methoxycyclopentan-1-yl)oxy]-2-(1-piperazinyl)quinazoline monohydrochloride (1.35 g) as crystals.

M.p.: around 216° C. (dec.) $[\alpha]_D^{20}=-25°$ (c=1.0, water) NMR (300 MHz, DMSO-$d_6$, δppm): 1.53 (1H, dt, J=4, 15 Hz), 2.77 (1H, dt, J=8, 15 Hz), 3.19 (4H, m), 3.26 (3H, s), 3.64 (1H, dt, J=3.5, 7.5 Hz), 3.94 (1H, q, J=3.5 Hz), 4.07 (4H, m), 4.17 (1H, q, J=5 Hz), 5.05 (1H, d, J=4.5 Hz), 5.15 (1H, d, J=5.5 Hz), 5.27 (1H, dt, J=5, 8.5 Hz), 7.26 (1H, ddd, J=1, 7, 8 Hz), 7.48 (1H, dt, J=1, 8.5 Hz), 7.71 (1H, ddd, J=1.5, 7, 8.5 Hz), 7.91 (1H, dd, J=1.5, 8 Hz), 9.42 (2H, br) Elementary analysis for $C_{18}H_{24}N_4O_4 \cdot HCl$: Calcd. (%): C,54.48; H,6.35; N,14.12 Found (%): C,54.33; H,6.28; N,14.12

EXAMPLE 42

4-[(2-Hydroxyethyl)oxy]-2-(1-piperazinyl)quinazoline:

To a solution of 2,4-dichloroquinazoline (1.0 g) and ethylene glycol (0.31 g) in dimethylformamide (20 ml) is added gradually 60% sodium hydride (in oil) (0.2 g) with stirring under ice-cooling, and the mixture is stirred at room temperature for 2 hours. The reaction mixture is poured into ice-water and extracted with ethyl acetate. The extract is washed with water, dried over anhydrous sodium sulfate and is evaporated to dryness under reduced pressure. The residue is dissolved in chloroform (10 ml)—dioxane (10 ml), and the solution is slowly added dropwise to a solution of piperazine (2.2 g) in dioxane (50 ml) with stirring at 70° C., and the mixture is stirred at the same temperature for one hour. The reaction mixture is poured into water, and extracted with chloroform. The extract is washed with water, dried over anhydrous sodium sulfate, and evaporated to dryness under reduced pressure. The resulting residue is purified by medium pressure liquid column chromatography (eluent, chloroform:methanol=10:1, 3:1, v/v) to give 4-[(2-hydroxyethyl)oxy]-2-(1-piperazinyl)quinazoline (0.46 g).

NMR (300 MHz, CDCl$_3$, δppm): 2.66 (2H, br), 2.96 (4H, m), 3.88 (4H, m), 4.04 (2H, m), 4.63 (2H, m), 7.12 (1H, ddd, J=1, 7, 8 Hz), 7.50 (1H, dt, J=1, 8.5 Hz), 7.58 (1H, ddd, J=1.5, 7, 8.5 Hz), 7.91 (1H, dd, J=1.5, 8 Hz)

EXAMPLE 43

4-[(2-Hydroxyethyl)oxy]-2-(1-piperazinyl)quinazoline monoacetate:

To a solution of 4-[(2-hydroxyethyl)oxy]-2-(1-piperazinyl)quinazoline (cf. Example 42) (1.2 g) in methanol (20 ml) is added acetic acid (0.3 g), and the mixture is evaporated to dryness under reduced pressure. The residue is recrystallized from acetonitrile to give 4-[(2-hydroxyethyl)oxy]-2-(1-piperazinyl)quinazoline monoacetate (0.2 g) as crystals.

M.p.: 148–150° C. NMR (300 MHz, DMSO-$d_6$, δppm): 1.89 (3H, s), 2.81 (4H, m), 3.7–3.9 (6H, m), 4.49 (2H, m), 5.20 (3H, br), 7.18 (1H, ddd, J=1, 7, 8 Hz), 7.40 (1H, d, J=8.5 Hz), 7.64 (1H, ddd, J=1.5, 7, 8.5 Hz), 7.92 (1H, dd, J=1.5, 8 Hz)

Elementary analysis for $C_{16}H_{22}N_4O_4 \cdot \frac{1}{4}H_2O$: Calcd. (%): C,56.71; H,6.69; N,16.53 Found (%): C,56.83; H,6.58; N,16.92

EXAMPLE 44

4-[(RS)-(2,3-Dihydroxypropyl)oxy]-2-(1-piperazinyl)quinazoline:

(1) 4-[(2-Propen-1-yl)oxy]-2-(1-piperazinyl)quinazoline:

To a solution of allyl alcohol (322 mg) and 2,4-dichloroquinazoline (1.00 g) in dioxane (8 ml) is added potassium t-butoxide (677 mg) with stirring under ice-cooling, and the mixture is stirred under ice-cooling for 15 minutes and further at room temperature for 30 minutes. The reaction mixture is diluted with ethyl acetate, and washed with water. The ethyl acetate solution is dried over anhydrous magnesium sulfate and evaporated to dryness under reduced pressure. The resulting residue is added to a solution of piperazine (2.17 g) in dioxane (11 ml) with stirring at 55° C., and the mixture is stirred at the same temperature for one hour. The reaction mixture is diluted with ethyl acetate, washed with water, and dried over anhydrous magnesium sulfate. The solution is evaporated to dryness under reduced pressure, and the resulting residue is purified by medium pressure liquid column chromatography (eluent, chloroform:methanol=10:1, 5:1, v/v) to give 4-[(2-propen-1-yl)oxy]-2-(1-piperazinyl)quinazoline (889 mg) as crystals.

NMR (300 MHz, CDCl$_3$, δppm): 1.85 (1H, s), 2.95 (4H, m), 3.89 (4H, m), 5.00 (2H, dt, J=1.5, 5.5 Hz), 5.31 (1H, dq, J=1, 10.5 Hz), 5.47 (1H, dq, J=1.5, 17.5 Hz), 6.0–6.3 (1H, m), 7.13 (1H, ddd, J=1, 7, 8 Hz), 7.49 (1H, dt, J=1, 8.5 Hz), 7.58 (1H, ddd, J=1.5, 7, 8.5 Hz), 7.94 (1H, ddd, J=0.5, 1.5, 8 Hz)

(2) 2-[4-(Benzyloxycarbonyl)piperazin-1-yl]-4-[(2-propen-1-yl)oxy]quinazoline:

To a solution of 4-[(2-propen-1-yl)oxy]-2-(1-piperazinyl)quinazoline (1.80 g) in dry methylene chloride (18 ml) is added triethylamine (1.88 ml) with stirring under ice-cooling, and thereto is further added dropwise a solution of benzyl chlorocarbonate (1.04 ml) in dry methylene chloride (3 ml). The mixture is stirred under ice-cooling for 2 hours. The reaction mixture is diluted with chloroform, washed with diluted hydrochloric acid and water, and dried over anhydrous magnesium sulfate. The solution is evaporated to dryness under reduced pressure, and the residue is purified by medium pressure liquid column chromatography (eluent, chloroform) to give 2-[4-(benzyloxycarbonyl)piperazin-1-yl]-4-[(2-propen-1-yl)oxy]quinazoline (1.76 g) as crystals.

NMR (300 MHz, CDCl$_3$, δppm): 3.63 (4H, m), 3.97 (4H, br), 5.02 (2H, dt, J=1.5, 5.5 Hz), 5.18 (2H, s), 5.34 (1H, dd, J=1, 10.5 Hz), 5.47 (1H, dq, J=1.5, 17.5 Hz), 6.0–6.2 (1H, m), 7.20 (1H, br), 7.3–7.4 (5H, m), 7.64 (2H, br), 7.98 (1H, dt, J=1.5, 8 Hz)

(3) 2-[4-(Benzyloxycarbonyl)piperazin-1-yl]-4-[(RS)-(2,3-dihydroxypropyl)oxy]quinazoline:

A mixture of 2-[4-(benzyloxycarbonyl)piperazin-1-yl]-4-[(2-propen-1-yl)oxy]quinazoline (1.00 g), a solution of osmium tetroxide in t-butanol (osmium tetroxide 106 mg/t-butanol 8.36 g) (248 mg) and 4-methylmorpholine N-oxide (305 mg) in water (9 ml)—acetone (28 ml) is stirred at room temperature for 21 hours. Acetone is distilled off from the reaction mixture under reduced pressure, and the resultant is diluted with ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=50:1, v/v) to give 2-[4-(benzyloxycarbonyl)piperazin-1-yl]-4-[(RS)-(2,3-dihydroxypropyl)oxy]quinazoline (1.03 g) as crystals.

NMR (300 MHz, CDCl₃, δppm): 3.59 (4H, m), 3.75 (1H, dd, J=5.5, 11.5 Hz), 3.8–3.9 (5H, m), 4.19 (1H, m), 4.5–4.6 (2H, m), 5.17 (2H, s), 7.14 (1H, ddd, J=1, 7, 8 Hz), 7.3–7.4 (5H, m), 7.50 (1H, d, J=8.5 Hz), 7.60 (1H, ddd, J=1.5, 7, 8.5 Hz), 7.88 (1H, dd, J=1.5, 8 Hz)

(4) 4-[(RS)-(2,3-Dihydroxypropyl)oxy]-2-(1-piperazinyl)quinazoline:

To a solution of 2-[4-(benzyloxycarbonyl)piperazin-1-yl]-4-[(RS)-(2,3-dihydroxypropyl)oxy]quinazoline (930 mg) in methanol (10 ml) is added 10% palladium/carbon (280 mg), and the mixture is stirred under hydrogen atmosphere and under atmospheric pressure at room temperature for 15 hours. To the reaction mixture is added chloroform (30 ml), and the mixture is filtered, and the filtrate is evaporated to dryness under reduced pressure. The residue is dissolved in methanol-chloroform, and the solution is filtered, and the filtrate is evaporated to dryness under reduced pressure. The residue is dissolved in acetone, and the solution is allowed to stand at room temperature, and the precipitated crystals are separated by filtration to give 4-[(RS)-(2,3-dihydroxypropyl)oxy]-2-(1-piperazinyl)quinazoline (355 mg) as crystals.

NMR (300 MHz, DMSO-d₆, δppm): 2.79 (4H, m), 3.51 (2H, d, J=5.5 Hz), 3.77 (4H, m), 3.93 (1H, m), 4.36 (1H, dd, J=6.5, 11 Hz), 4.52 (1H, dd, J=4, 11 Hz), 7.18 (1H, ddd, J=1, 7, 8 Hz), 7.40 (1H, d, J=8.5 Hz), 7.64 (1H, ddd, J=1.5, 7, 8.5 Hz), 7.93 (1H, dd, J=1.5, 8 Hz)

EXAMPLE 45

4-[(RS)-(2,3-Dihydroxypropyl)oxy]-2-(1-piperazinyl)quinazoline monoacetate:

To a solution of 4-[(RS)-(2,3-dihydroxypropyl)oxy]-2-(1-piperazinyl)quinazoline (cf. Example 44) (300 mg) in acetone-methanol is added acetic acid (65 mg), and the mixture is filtered, and the filtrate is evaporated to dryness under reduced pressure. The residue is recrystallized from methanol-acetone to give 4-[(RS)-(2,3-dihydroxypropyl)oxy]-2-(1-piperazinyl)quinazoline monoacetate (237 mg) as crystals.

M.p.: around 149° C. (dec.) NMR (300 MHz, DMSO-d₆, δppm): 1.89 (3H, s), 2.81 (4H, m), 3.51 (2H, d, J=6 Hz), 3.79 (4H, m), 3.92 (1H, m), 4.35 (1H, dd, J=6.5, 11 Hz), 4.52 (1H, dd, J=4, 11 Hz), 5.52 (4H, br), 7.18 (1H, ddd, J=1, 7, 8 Hz), 7.40 (1H, d, J=8.5 Hz), 7.64 (1H, ddd, J=1.5, 7, 8.5 Hz), 7.93 (1H, dd, J=1.5, 8 Hz) Elementary analysis for $C_{17}H_{24}N_4O_5$: Calcd. (%): C,56.03; H,6.64; N,15.38 Found (%): C,55.88; H,6.56; N,15.57

EXAMPLE 46

4-[(2RS,3SR)-(3-Hydroxybutan-2-yl)oxy]-2-(1-piperazinyl)quinazoline:

To a solution of meso-2,3-butanediol [manufactured by Aldrich Co.] (1.00 g) and 2,4-dichloroquinazoline (2.00 g) in dimethylformamide (10 ml) is added gradually 60% sodium hydride (in oil) (523 mg) with stirring under ice-cooling, and the mixture is stirred at room temperature for 4 hours. The reaction mixture is diluted with ethyl acetate and washed with water 5 times. The ethyl acetate solution is dried over anhydrous magnesium sulfate and evaporated to dryness under reduced pressure, and the residue is briefly purified by medium pressure liquid column chromatography (eluent, chloroform). The resulting crystalline substance is dissolved in dioxane (10 ml), and the mixture is added dropwise to a solution of piperazine (1.87 g) in dioxane (6 ml) with stirring at 80° C., and the mixture is stirred at the same temperature for 2.5 hours. The reaction mixture is diluted with ethyl acetate, washed with water, and dried over anhydrous magnesium sulfate. The solution is evaporated to dryness under reduced pressure, and the residue is purified by medium pressure liquid column chromatography (eluent, chloroform:methanol=10:1, 5:1, v/v) to give 4-[(2RS,3SR)-(3-hydroxybutan-2-yl)oxy]-2-(1-piperazinyl)quinazoline (750 mg) as crystals.

NMR (300 MHz, CDCl₃, δppm): 1.31 (3H, d, J=6.5 Hz), 1.42 (3H, d, J=6.5 Hz), 2.45 (2H, br), 2.97 (4H, m), 3.88 (4H, m), 4.10 (1H, dq, J=3, 6.5 Hz), 5.41 (1H, dq, J=3, 6.5 Hz), 7.13 (1H, ddd, J=1, 7, 8 Hz), 7.49 (1H, dd, J=1, 8.5 Hz), 7.59 (1H, ddd, J=1.5, 7, 8.5 Hz), 7.91 (1H, dd, J=1.5, 8 Hz)

EXAMPLE 47

4-[(2RS,3SR)-(3-Hydroxybutan-2-yl)oxy]-2-(1-piperazinyl)quinazoline monoacetate:

To a suspension of 4-[(2RS,3SR)-(3-hydroxybutan-2-yl)oxy]-2-(1-piperazinyl)quinazoline (cf. Example 46) (600 mg) in acetone (20 ml) is added acetic acid (136 mg), and the mixture is filtered, and the filtrate is allowed to stand at room temperature, and the precipitated crystals are separated by filtration to give 4-[(2RS,3SR)-(3-hydroxybutan-2-yl)oxy]-2-(1-piperazinyl)quinazoline monoacetate (478 mg) as crystals.

M.p.: around 144° C. (dec.) NMR (300 MHz, DMSO-d₆, δppm): 1.18 (3H, d, J=6.5 Hz), 1.34 (3H, d, J=6.5 Hz), 1.89 (3H, s), 2.81 (4H, m), 3.78 (4H, m), 3.88 (1H, dq, J=4.5, 6.5 Hz), 5.19 (1H, dq, J=4.5, 6.5 Hz), 5.74 (3H, br), 7.17 (1H, ddd, J=1, 7, 8 Hz), 7.40 (1H, d, J=8.5 Hz), 7.64 (1H, ddd, J=1.5, 7, 8.5 Hz), 7.91 (1H, ddd, J=0.5, 1.5, 8 Hz) Elementary analysis for $C_{18}H_{26}N_4O_4$: Calcd. (%): C,59.65; H,7.23; N,15.46 Found (%): C,59.29; H,7.19; N,15.31

EXAMPLE 48

4-[(2S,3S)-(3-Hydroxybutan-2-yl)oxy]-2-(1-piperazinyl)quinazoline:

To a solution of (2S,3S)-2,3-butanediol [manufactured by Tokyo Kasei Kogyo K.K.] (1.00 g) and 2,4-dichloroquinazoline (2.00 g) in dimethylformamide (10 ml) is added gradually 60% sodium hydride (in oil) (523 mg) with stirring under ice-cooling, and the mixture is stirred at room temperature for 4 hours. The reaction mixture is diluted with ethyl acetate and washed with water 5 times. The ethyl acetate solution is dried over anhydrous magnesium sulfate and evaporated to dryness under reduced pressure, and the residue is washed with n-hexane. The resulting crystalline substance is added to a solution of piperazine (2.82 g) in dioxane (17 ml) with stirring at 60° C., and the mixture is stirred at the same temperature for 25 minutes. The reaction mixture is diluted with ethyl acetate, washed with water, and dried over anhydrous magnesium sulfate. The solution is evaporated to dryness under reduced pressure, and the residue is purified by medium pressure liquid column chromatography (eluent, chloroform:methanol=10:1, 5:1, v/v) to give 4-[(2S,3S)-(3-hydroxybutan-2-yl)oxy]-2-(1-piperazinyl) quinazoline (1.08 g) as crystals.

NMR (300 MHz, DMSO-d₆, δppm): 1.15 (3H, d, J=6.5 Hz), 1.32 (3H, d, J=6.5 Hz), 2.78 (4H, m), 3.26 (1H, br), 3.75 (4H, m), 3.88 (1H, dq, J=5, 6.5 Hz), 4.90 (1H, br), 5.25 (1H, dq, J=5, 6.5 Hz), 7.15 (1H, ddd, J=1, 7, 8 Hz), 7.38 (1H, dd, J=1, 8.5 Hz), 7.63 (1H, ddd, J=1.5, 7, 8.5 Hz), 7.92 (1H, dd, J=1.5, 8 Hz)

EXAMPLE 49

4-[(2S,3S)-(3-Hydroxybutan-2-yl)oxy]-2-(1-piperazinyl) quinazoline monoacetate:

4-[(2S,3S)-(3-Hydroxybutan-2-yl)oxy]-2-(1-piperazinyl) quinazoline (cf. Example 48) (650 mg) is dissolved in a solution of acetic acid (147 mg) in acetone (20 ml), and the mixture is filtered. The filtrate is evaporated to dryness under reduced pressure, and the residue is dissolved in ethyl acetate (8 ml), and the solution is allowed to stand at room temperature. The precipitated crystals are separated by filtration to give 4-[(2S,3S)-(3-hydroxybutan-2-yl)oxy]-2-(1-piperazinyl)quinazoline monoacetate (546 mg) as crystals.

M.p.: 120–122° C. NMR (300 MHz, DMSO-$d_6$, δppm): 1.15 (3H, d, J=6.5 Hz), 1.32 (3H, d, J=6.5 Hz), 1.89 (3H, s), 2.81 (4H, m), 3.77 (4H, m), 3.88 (1H, dq, J=5, 6.5 Hz), 5.25 (1H, dq, J=5, 6.5 Hz), 5.76 (3H, br), 7.17 (1H, ddd, J=1, 7, 8 Hz), 7.39 (1H, d, J=8.5 Hz), 7.63 (1H, ddd, J=1.5, 7, 8.5 Hz), 7.93 (1H, dd, J=1.5, 8 Hz) Elementary analysis for $C_{18}H_{26}N_4O_4$: Calcd. (%): C,59.65; H,7.23; N,15.46 Found (%): C,59.40; H,7.21; N,15.44

EXAMPLE 50

4-[(2R,3R)-(3-Hydroxybutan-2-yl)oxy]-2-(1-piperazinyl) quinazoline:

To a solution of (2R,3R)-2,3-butanediol [manufactured by Tokyo Kasei Kogyo K.K.] (1.00 g) and 2,4-dichloroquinazoline (2.00 g) in dimethylformamide (10 ml) is added gradually 60% sodium hydride (in oil) (523 mg) with stirring under ice-cooling, and the mixture is stirred at room temperature for 2 hours. The reaction mixture is diluted with ethyl acetate and washed with water 5 times. The ethyl acetate solution is dried over anhydrous magnesium sulfate and evaporated to dryness under reduced pressure, and the residue is washed with isopropyl ether-n-hexane (2:5). The resulting crystalline substance is added to a solution of piperazine (2.33 g) in dioxane (14 ml) with stirring at 60° C., and the mixture is stirred at the same temperature for 30 minutes. The reaction mixture is diluted with ethyl acetate, washed with water, and dried over anhydrous magnesium sulfate. The solution is evaporated to dryness under reduced pressure, and the residue is purified by medium pressure liquid column chromatography (eluent, chloroform:methanol=15:1, v/v) to give 4-[(2R,3R)-(3-hydroxybutan-2-yl)oxy]-2-(1-piperazinyl) quinazoline (0.97 g) as crystals.

NMR (300 MHz, DMSO-$d_6$, δppm): 1.15 (3H, d, J=6.5 Hz), 1.32 (3H, d, J=6.5 Hz), 2.77 (4H, m), 3.16 (1H, br), 3.75 (4H, m), 3.89 (1H, dq, J=5, 6.5 Hz), 4.92 (1H, br), 5.25 (1H, dq, J=5, 6.5 Hz), 7.16 (1H, ddd, J=1, 7, 8 Hz), 7.39 (1H, dd, J=1, 8.5 Hz), 7.63 (1H, ddd, J=1.5, 7, 8.5 Hz), 7.93 (1H, dd, J=1.5, 8 Hz)

EXAMPLE 51

4-[(2R,3R)-(3-Hydroxybutan-2-yl)oxy]-2-(1-piperazinyl) quinazoline monoacetate:

4-[(2R,3R)-(3-Hydroxybutan-2-yl)oxy]-2-(1-piperazinyl) quinazoline (cf. Example 50) (600 mg) is dissolved in acetone (30 ml), and the mixture is filtered. To the filtrate is added acetic acid (135 mg), and the mixture is evaporated to dryness under reduced pressure, and the residue is dissolved in ethyl acetate (6 ml), and the solution is allowed to stand at room temperature. The precipitated crystals are separated by filtration to give 4-[(2R,3R)-(3-hydroxybutan-2-yl)oxy]-2-(1-piperazinyl)quinazoline monoacetate (443 mg) as crystals.

M.p.: 120–122° C. NMR (300 MHz, DMSO-$d_6$, δppm): 1.15 (3H, d, J=6.5 Hz), 1.32 (3H, d, J=6.5 Hz), 1.89 (3H, s), 2.81 (4H, m), 3.78 (4H, m), 3.88 (1H, dq, J=5, 6.5 Hz), 5.26 (1H, dq, J=5, 6.5 Hz), 5.82 (3H, br), 7.17 (1H, ddd, J=1, 7, 8 Hz), 7.40 (1H, d, J=8.5 Hz), 7.63 (1H, ddd, J=1.5, 7, 8.5 Hz), 7.93 (1H, dd, J=1.5, 8 Hz) Elementary analysis for $C_{18}H_{26}N_4O_4$: Calcd. (%): C,59.65; H,7.23; N,15.46 Found (%): C,59.50; H,7.13; N,15.46

EXAMPLE 52

4-[(2RS,3RS)-(2,3-Dihydroxybutan-1-yl)oxy]-2-(1-piperazinyl)quinazoline:

(1) 4-[trans-(2-Buten-1-yl)oxy]-2-(1-piperazinyl) quinazoline:

To a solution of trans-crotyl alcohol (manufactured by Tokyo Kasei Kogyo K.K.) (638 mg) and 2,4-dichloroquinazoline (1.60 g) in dimethylformamide (8 ml) is added 60% sodium hydride (in oil) (386 mg) with stirring at room temperature, and the mixture is stirred at room temperature for 3.5 hours. The reaction mixture is diluted with ethyl acetate and washed with water 5 times. The ethyl acetate solution is dried over anhydrous magnesium sulfate and evaporated to dryness under reduced pressure. The resulting residue is added to a solution of piperazine (3.46 g) in dioxane (15 ml) with stirring at 60° C., and the mixture is stirred at the same temperature for 2 hours. The reaction mixture is diluted with ethyl acetate, washed with water, and dried over anhydrous magnesium sulfate. The solution is evaporated to dryness under reduced pressure, and the residue is purified by medium pressure liquid column chromatography (eluent, chloroform:methanol=20:1, 10:1, v/v) to give 4-[trans-(2-buten-1-yl)oxy]-2-(1-piperazinyl) quinazoline (1.36 g) as crystals.

NMR (300 MHz, CDCl$_3$, δppm): 1.78 (3H, dd, J=1, 6 Hz), 2.75 (1H, s), 2.99 (4H, m), 3.93 (4H, m), 4.93 (2H, m), 5.7–6.0 (2H, m), 7.12 (1H, ddd, J=1, 7, 8 Hz), 7.48 (1H, dt, J=1, 8.5 Hz), 7.58 (1H, ddd, J=1.5, 7, 8.5 Hz), 7.93 (1H, ddd, J=0.5, 1.5, 8 Hz)

(2) 2-[4-(Benzyloxycarbonyl)piperazin-1-yl]-4-[trans-(2-buten-1-yl)oxy]quinazoline:

To a solution of 4-[trans-(2-buten-1-yl)oxy]-2-(1-piperazinyl) quinazoline (1.20 g) in dry methylene chloride (12 ml) is added triethylamine (1.77 ml) with stirring under ice-cooling, and thereto is further added dropwise a solution of benzyl chlorocarbonate (0.73 ml) in dry methylene chloride (5 ml). The mixture is stirred under ice-cooling for 3 hours. The reaction mixture is diluted with chloroform, washed with water, and dried over anhydrous magnesium sulfate. The solution is evaporated to dryness under reduced pressure, and the residue is purified by medium pressure liquid column chromatography (elutant, chloroform) to give 2-[4-(benzyloxycarbonyl)piperazin-1-yl]-4-[trans-(2-buten-1-yl)oxy]quinazoline (1.57 g) as crystals.

NMR (300 MHz, CDCl$_3$, δppm): 1.78 (3H, dd, J=1, 6 Hz), 3.61 (4H, m), 3.92 (4H, br), 4.92 (2H, m), 5.18 (2H, s), 5.7–6.0 (2H, m), 7.14 (1H, ddd, J=1, 7, 8 Hz), 7.3–7.4 (5H, m), 7.49 (1H, dt, J=1, 8.5 Hz), 7.59 (1H, ddd, J=1.5, 7, 8.5 Hz), 7.94 (1H, ddd, J=0.5, 1.5, 8 Hz)

(3) 2-[4-(Benzyloxycarbonyl)piperazin-1-yl]-4-[(2RS, 3RS)-(2,3-dihydroxybutan-1-yl)oxy]quinazoline:

A mixture of 2-[4-(benzyloxycarbonyl)piperazin-1-yl]-4-[trans-(2-buten-1-yl)oxy]quinazoline (1.30 g), a solution of osmium tetroxide in t-butanol (osmium tetroxide 106 mg/t-butanol 8.36 g) (312 mg) and 4-methylmorpholine N-oxide (382 mg) in water (2 ml)—acetone (15 ml) is stirred at room temperature for 14 hours. Acetone is distilled off from the reaction mixture under reduced pressure, and the resultant product is diluted with ethyl acetate, and the mixture is washed with 10% aqueous sodium sulfite solution and water. The ethyl acetate solution is dried over anhydrous magnesium sulfate and evaporated to dryness under reduced pressure, and the residue is purified by medium pressure liquid column chromatography (eluent, chloroform:methanol=100:1, v/v) to give 2-[4-(benzyloxycarbonyl)piperazin-1-yl]-4-[(2RS,3RS)-(2,3-dihydroxybutan-1-yl)oxy]quinazoline (1.02 g) as foam.

NMR (300 MHz, CDCl$_3$—D$_2$O, δppm): 1.32 (3H, d, J=6 Hz), 3.60 (4H, m), 3.8–4.0 (6H, m), 4.54 (1H, dd, J=6, 11.5 Hz), 4.63 (1H, dd, J=4, 11.5 Hz), 5.17 (2H, s), 7.16 (1H, ddd, J=1, 7, 8 Hz), 7.3–7.4 (5H, m), 7.51 (1H, dt, J=1, 8.5 Hz), 7.62 (1H, ddd, J=1.5, 7, 8.5 Hz), 7.89 (1H, dd, J=1.5, 8 Hz)

(4) 4-[(2RS,3RS)-(2,3-Dihydroxybutan-1-yl)oxy]-2-(1-piperazinyl)quinazoline:

To a solution of 2-[4-(benzyloxycarbonyl)piperazin-1-yl]-4-[(2RS,3RS)-(2,3-dihydroxybutan-1-yl)oxy]quinazoline (950 mg) in methanol (21 ml) is added 10% palladium/carbon (109 mg), and the mixture is stirred under hydrogen atmosphere and under atmospheric pressure at room temperature for 8 hours. The reaction mixture is filtered, and the filtrate is evaporated to dryness under reduced pressure, and the residue is crystallized from acetone-diethyl ether. The crystals thus obtained are recrystallized from ethanol - diethyl ether to give 4-[(2RS,3RS)-(2,3-dihydroxybutan-1-yl)oxy]-2-(1-piperazinyl)quinazoline (235 mg) as crystals.

NMR (300 MHz, DMSO-d$_6$, δppm): 1.14 (3H, d, J=6 Hz), 2.78 (4H, m), 3.26 (1H, br), 3.6–3.8 (6H, m), 4.2–4.8 (1H, br), 4.37 (1H, dd, J=6.5, 11 Hz), 4.52 (1H, dd, J=4, 11 Hz), 4.95 (1H, br), 7.17 (1H, ddd, J=1, 7, 8 Hz), 7.40 (1H, d, J=8.5 Hz), 7.64 (1H, ddd, J=1.5, 7, 8.5 Hz), 7.90 (1H, dd, J=1.5, 8 Hz)

EXAMPLE 53

4-[(2S,3S)-(2,3-Dihydroxybutan-1-yl)oxy]-2-(1-piperazinyl)quinazoline:

(1) 2-[4-(Benzyloxycarbonyl)piperazin-1-yl]-4-[(2S,3S)-(2,3-dihydroxybutan-1-yl) oxy]quinazoline:

AD-mix-α (manufactured by Aldrich Co.) (35 g) and methanesulfonamide (2.4 g) are suspended in t-butanol (150 ml)—water (150 ml), and after cooling to 5° C., to the mixture is added 2-[4-(benzyloxycarbonyl)piperazin-1-yl)-4-[trans-(2-buten-1-yl) oxy]quinazoline [cf. Example 52(2)] (10.5 g) with vigorously stirring, and the mixture is vigorously stirred under cooling at 5° C. for one day. The reaction mixture is allowed to warm to room temperature, and thereto is added sodium sulfite (37.5 g), and the mixture is stirred for one hour and extracted with ethyl acetate. The extract is washed with 10% aqueous sodium hydroxide and with water, dried over anhydrous sodium sulfate, and evaporated to dryness under reduced pressure. The resulting residue is purified by medium pressure liquid column chromatography (eluent, chloroform:methanol=100:1, v/v), and recrystallized twice from isopropyl alcohol to give 2-[4-(benzyloxycarbonyl)piperazin-1-yl]-4-[(2S,3S)-(2,3-dihydroxybutan-1-yl)oxy]quinazoline (5.7 g).

NMR (300 MHz, CDCl$_3$, δppm): 1.32 (3H, d, J=6.5 Hz), 2.5–3.5 (2H, br), 3.61 (4H, m), 3.8–4.1 (6H, m), 4.54 (1H, dd, J=6, 11.5 Hz), 4.63 (1H, dd, J=4, 11.5 Hz), 5.18 (2H, s), 7.16 (1H, ddd, J=1, 7, 8 Hz), 7.2–7.4 (5H, m), 7.50 (1H, d, J=8.5 Hz), 7.62 (1H, ddd, J=1.5, 7, 8.5 Hz), 7.90 (1H, dd, J=1.5, 8 Hz)

(2) 4-[(2S,3S)-(2,3-Dihydroxybutan-1-yl)oxy]-2-(1-piperazinyl)quinazoline:

2-[4-(Benzyloxycarbonyl)piperazin-1-yl]-4-[(2S,3S)-(2,3-dihydroxybutan-1-yl)oxy]quinazoline (5.1 g) is dissolved in methanol (90 ml)—dioxane (10 ml), and thereto is added 10% palladium/carbon (0.5 g), and the mixture is stirred under hydrogen atmosphere and under atmospheric pressure at room temperature for 16 hours. The reaction mixture is filtered, and the filtrate is evaporated to dryness under reduced pressure to give 4-[(2S,3S)-(2,3-dihydroxybutan-1-yl)oxy]-2-(1-piperazinyl)quinazoline (3.3 g).

NMR (300 MHz, CDCl$_3$, δppm): 1.32 (3H, d, J=6.5 Hz), 2.2–2.8 (3H, br), 2.93 (4H, m), 3.7–4.0 (6H, m), 4.52 (1H, dd, J=6, 11.5 Hz), 4.61 (1H, dd, J=4.5, 11.5 Hz), 7.11 (1H, ddd, J=1, 7, 8 Hz), 7.48 (1H, dt, J=1, 8.5 Hz), 7.59 (1H, ddd, J=1.5, 7, 8.5 Hz), 7.85 (1H, dd, J=1.5, 8 Hz)

EXAMPLE 54

4-[(2S,3S)-(2,3-Dihydroxybutan-1-yl)oxy]-2-(1-piperazinyl]quinazoline monohydrochloride:

4-[(2S,3S)-(2,3-Dihydroxybutan-1-yl)oxy]-2-(1-piperazinyl]quinazoline (cf. Example 53) (3.1 g) is dissolved in methanol (20 ml), and thereto is added 2N NCl-methanol (4.8 ml), and the mixture is evaporated to dryness under reduced pressure. The resulting residue is recrystallized from ethanol to give 4-[(2S,3S)-(2,3-dihydroxybutan-1-yl)oxy]-2-(1-piperazinyl)quinazoline monohydrochloride (1.9 g).

M.p.: 165–169° C. NMR (300 MHz, DMSO-d$_6$, δppm): 1.14 (3H, d, J=6 Hz), 3.18 (4H, m), 3.78 (2H, m), 4.06 (4H, m), 4.40 (1H, dd, J=6.5, 11 Hz), 4.55 (1H, dd, J=4, 11 Hz), 4.65 (1H, d, J=5 Hz), 5.03 (1H, d, J=5.5 Hz), 7.26 (1H, ddd, J=1, 7, 8 Hz), 7.47 (1H, d, J=8.5 Hz), 7.71 (1H, ddd, J=1.5, 7, 8.5 Hz), 7.96 (1H, dd, J=1.5, 8 Hz), 9.46 (2H, br) Elementary analysis for C$_{16}$H$_{22}$N$_4$O$_3$ HCl ⅔H$_2$O: Calcd. (%): C,52.40; H,6.68; N,15.28 Found (%): C,52.43; H,6.49; N,15.42

EXAMPLE 55

4-[(2R,3R)-(2,3-Dihydroxybutan-1-yl)oxy]-2-(1-piperazinyl)quinazoline:

(1) 2-[4-(Benzyloxycarbonyl)piperazin-1-yl]-4-[(2R,3R)-(2,3-dihydroxybutan-1-yl)oxy]quinazoline:

AD-mix-β (manufactured by Aldrich Co.) (35 g) and methanesulfonamide (2.4 g) are suspended in t-butanol (150 ml)—water (150 ml), and after cooling to 5° C., to the mixture is added 2-[4-(benzyloxycarbonyl)piperazin-1-yl)-4-[trans-(2-buten-1-yl) oxy]quinazoline [cf. Example 52(2)] (10.5 g) with vigorously stirring, and the mixture is vigorously stirred under cooling at 5° C. for one day. The reaction mixture is allowed to warm to room temperature, and thereto is added sodium sulfite (37.5 g), and the mixture is stirred for one hour and extracted with ethyl acetate. The extract is washed with 10% aqueous sodium hydroxide and with water, dried over anhydrous sodium sulfate, and evaporated to dryness under reduced pressure. The resulting residue is purified by medium pressure liquid column chromatography (eluent, chloroform:methanol=100:1, v/v), and recrystallized from isopropyl alcohol to give 2-[4-(benzyloxycarbonyl)piperazin-1-yl]-4-[(2R,3R)-(2,3-dihydroxybutan-1-yl)oxy]quinazoline (7.6 g).

NMR (300 MHz, CDCl$_3$, δppm): 1.32 (3H, d, J=6.5 Hz), 2.3–3.5 (2H, br), 3.61 (4H, m), 3.8–4.1 (6H, m), 4.54 (1H, dd, J=6, 11.5 Hz), 4.62 (1H, dd, J=4, 11.5 Hz), 5.17 (2H, s), 7.16 (1H, ddd, J=1, 7, 8 Hz), 7.2–7.4 (5H, m), 7.50 (1H, d, J=8.5 Hz), 7.62 (1H, ddd, J=1.5, 7, 8.5 Hz), 7.89 (1H, dd, J=1.5, 8 Hz)

(2) 4-[(2R,3R)-(2,3-Dihydroxybutan-1-yl)oxy]-2-(1-piperazinyl)quinazoline:

2-[4-(Benzyloxycarbonyl)piperazin-1-yl]-4-[(2R,3R)-(2,3-dihydroxybutan-1-yl)oxy]quinazoline (1.3 g) is dissolved in methanol (20 ml), and thereto is added 10% palladium/carbon (0.4 g), and the mixture is stirred under hydrogen atmosphere and under atmospheric pressure at room temperature for 16 hours. The reaction mixture is filtered, and the filtrate is evaporated to dryness under reduced pressure to give 4-[(2R,3R)-(2,3-dihydroxybutan-1-yl)oxy]-2-(1-piperazinyl)quinazoline (0.9 g).

NMR (300 MHz, CDCl$_3$, δppm): 1.32 (3H, d, J=6.5 Hz), 2.5–2.8 (3H, br), 2.94 (4H, m), 3.8–4.0 (6H, m), 4.52 (1H, dd, J=6, 11.5 Hz), 4.61 (1H, dd, J=4.5, 11.5 Hz), 7.11 (1H, ddd, J=1, 7, 8 Hz), 7.48 (1H, dt, J=1, 8.5 Hz), 7.59 (1H, ddd, J=1.5, 7, 8.5 Hz), 7.85 (1H, dd, J=1.5, 8 Hz)

EXAMPLE 56

4-[(2R,3R)-(2,3-Dihydroxybutan-1-yl)oxy]-2-(1-piperazinyl)quinazoline monohydrochloride:

4-[(2R,3R)-(2,3-Dihydroxybutan-1-yl)oxy]-2-(1-piperazinyl)quinazoline (cf. Example 55) (0.85 g) is dissolved in methanol (10 ml), and thereto is added 2N HCl-methanol (1.6 ml), and the mixture is evaporated to dryness under reduced pressure. The resulting residue is recrystallized from ethanol to give 4-[(2R,3R)-(2,3-dihydroxybutan-1-yl)oxy]-2-(1-piperazinyl)quinazoline monohydrochloride (0.3 g).

M.p.: 160–165° C. NMR (300 MHz, DMSO-d$_6$, δppm): 1.14 (3H, d, J=6 Hz), 3.18 (4H, m), 3.77 (2H, m), 4.06 (4H, m), 4.40 (1H, dd, J=6.5, 11 Hz), 4.56 (1H, dd, J=4, 11 Hz), 4.64 (1H, m), 5.03 (1H, m), 7.26 (1H, ddd, J=1, 7, 8 Hz), 7.47 (1H, d, J=8.5 Hz), 7.71 (1H, ddd, J=1.5, 7, 8.5 Hz), 7.96 (1H, dd, J=1.5, 8 Hz), 9.43 (2H, br)

Elementary analysis for C$_{16}$H$_{22}$N$_4$O$_3$ HCl: Calcd. (%): C,54.16; H,6.53; N,15.79 Found (%): C,54.11; H,6.57; N,15.92

EXAMPLE 57

4-[(3S)-(3,4-Dihydroxybutan-1-yl)oxy]-2-(1-piperazinyl)quinazoline:

(1) 4-[(3-Buten-1-yl)oxy]-2-(1-piperazinyl)quinazoline:

To a solution of 3-buten-1-ol (8.4 g) and 2,4-dichloroquinazoline (21.0 g) in dimethylformamide (105 ml) is added 60% sodium hydride (in oil) (5.51 g) with stirring under ice-cooling, and the mixture is stirred under ice-cooling for 20 minutes and at room temperature for 3.5 hours. The reaction mixture is diluted with ethyl acetate and washed with water 5 times. The ethyl acetate solution is dried over anhydrous magnesium sulfate and evaporated to dryness under reduced pressure. The resulting residue is dissolved in dioxane (70 ml) and the solution is added dropwise to a solution of piperazine (36.5 g) in dioxane (300 ml) with stirring at 50° C., and the mixture is stirred at the same temperature for one hour and 20 minutes. The reaction mixture is diluted with ethyl acetate, washed with water, and thereto is added acetic acid (9.6 g), and the mixture is extracted with water twice. The aqueous solution is made alkaline with aqueous sodium carbonate and then extracted with ethyl acetate twice. The ethyl acetate solution is washed with water, dried over anhydrous magnesium sulfate, and evaporated to dryness under reduced pressure to give 4-[(3-buten-1-yl)oxy]-2-(1-piperazinyl)quinazoline (23.8 g) as crystals.

NMR (300 MHz, CDCl$_3$, δppm): 2.64 (2H, tq, J=1.5, 6.5 Hz), 3.14 (4H, m), 4.09 (4H, m), 4.53 (2H, t, J=6.5 Hz), 5.13 (1H, m), 5.21 (1H, dq, J=1.5, 17 Hz), 5.93 (1H, m), 5.8–6.1 (1H, br), 7.17 (1H, ddd, J=1, 7, 8 Hz), 7.50 (1H, dt, J=1, 8.5 Hz), 7.61 (1H, ddd, J=1.5, 7, 8.5 Hz), 7.93 (1H, ddd, J=0.5, 1.5, 8 Hz)

(2) 2-[4-(Benzyloxycarbonyl)piperazin-1-yl]-4-[(3-buten-1-yl) oxy]quinazoline:

To a solution of 4-[(3-buten-1-yl)oxy]-2-(1-piperazinyl) quinazoline (23.3 g) in dry methylene chloride (200 ml) is added triethylamine (22.9 ml) with stirring under ice-cooling, and thereto is further added dropwise a solution of benzyl chlorocarbonate (12.3 ml) in dry methylene chloride (30 ml). The mixture is stirred under ice-cooling for 5 hours. The reaction mixture is diluted with chloroform, washed with water, and dried over anhydrous magnesium sulfate. The solution is evaporated to dryness under reduced pressure, and the residue is purified by medium pressure liquid column chromatography (eluent, chloroform) to give 2-[4-(benzyloxycarbonyl) piperazin-1-yl]-4-[(3-buten-1-yl)oxy]quinazoline (26.7 g) as crystals.

NMR (300 MHz, CDCl$_3$, δppm): 2.63 (3H, tq, J=1.5, 6.5 Hz), 3.61 (4H, m), 3.92 (4H, br), 4.52 (2H, t, J=6.5 Hz), 5.13 (1H, m), 5.17 (2H, s), 5.20 (1H, dq, J=1.5, 17.5 Hz), 5.8–6.0 (1H, m), 7.15 (1H, ddd, J=1, 7, 8 Hz), 7.3–7.4 (5H, m), 7.49 (1H, dt, J=1, 8.5 Hz), 7.60 (1H, ddd, J=1.5, 7, 8.5 Hz), 7.92 (1H, ddd, J=0.5, 1.5, 8 Hz)

(3) 2-[4-(Benzyloxycarbonyl)piperazin-1-yl]-4-[(3S)-(3,4-dihydroxybutan-1-yl)oxy]quinazoline:

To a mixture of AD-mix-α (manufactured by Aldrich Co.) (29.74 g), t-butanol (106 ml) and water (106 ml) is added 2-[4-(benzyloxycarbonyl)piperazin-1-yl]-4-[(3-buten-1-yl) oxy]-quinazoline (8.88 g) with stirring under ice-cooling, and the mixture is stirred under ice-cooling for 22 hours. To the reaction mixture is added sodium sulfite (31.8 g), and the mixture is stirred at room temperature for 35 minutes. The reaction mixture is separated into an organic layer and an aqueous layer, and the aqueous layer is extracted with ethyl acetate. The organic layer is combined with the ethyl acetate extract, and washed with water. The ethyl acetate solution is dried over anhydrous magnesium sulfate, evaporated to dryness under reduced pressure, and the residue is purified by medium pressure liquid column chromatography (eluent, chloroform:methanol=50:1, v/v), and the resulting crystalline product is recrystallized twice from acetone-diethyl ether to give 2-[4-(benzyloxycarbonyl)piperazin-1-yl]-4-[(3S)-(3,4-dihydroxybutan-1-yl)oxy]quinazoline (2.15 g) as crystals.

NMR (300 MHz, CDCl$_3$—D$_2$O, δppm): 1.9–2.2 (2H, m), 3.5–3.7 (5H, m), 3.75 (1H, dd, J=3.5, 11 Hz), 3.8–4.1 (5H, m), 4.61 (1H, m), 4.75 (1H, m), 5.18 (2H, s), 7.15 (1H, ddd, J=1, 7, 8 Hz), 7.3–7.4 (5H, m), 7.50 (1H, dt, J=1, 8.5 Hz), 7.61 (1H, ddd, J=1.5, 7, 8.5 Hz), 7.88 (1H, ddd, J=0.5, 1.5, 8 Hz) Elementary analysis for C$_{24}$H$_{28}$N$_4$O$_5$: Calcd. (%): C,63.70; H,6.24; N,12.38 Found (%): C,63.62; H,6.19; N,12.40

(4) 4-[(3S)-(3,4-Dihydroxybutan-1-yl)oxy]-2-(1-piperazinyl)quinazoline:

To a solution of 2-[4-(benzyloxycarbonyl)piperazin-1-yl]-4-[(3S)-(3,4-dihydroxybutan-1-yl)oxy]quinazoline (2.00 g) in methanol (40 ml) is added 10% palladium/carbon (300 mg), and the mixture is stirred under hydrogen atmosphere and under atmospheric pressure at room temperature for 21.5 hours. The reaction mixture is filtered, and the filtrate is evaporated to dryness under reduced pressure, and the residue is washed with acetone to give 4-[(3S)-(3,4-dihydroxybutan-1-yl)oxy]-2-(1-piperazinyl)quinazoline (1.10 g) as crystals.

NMR (300 MHz, DMSO-d$_6$—D$_2$O, δppm): 1.7–1.9 (1H, m), 2.0–2.2 (1H, m), 2.77 (4H, m), 3.39 (2H, m), 3.7–3.9 (5H, m), 4.58 (2H, m), 7.20 (1H, ddd, J=1, 7, 8 Hz), 7.44 (1H, d, J=8.5 Hz), 7.67 (1H, ddd, J=1.5, 7, 8.5 Hz), 7.88 (1H, dd, J=1.5, 8 Hz)

EXAMPLE 58

4-[(3S)-(3,4-Dihydroxybutan-1-yl)oxy]-2-(1-piperazinyl]quinazoline monohydrochloride:

To a solution of 4-[(3S)-(3,4-dihydroxybutan-1-yl)oxy]-2-(1-piperazinyl)quinazoline (cf. Example 57) (1.00 g) in methanol (20 ml) is added 2N HCl-methanol (1.89 ml), and the mixture is evaporated to dryness under reduced pressure. The resulting residue is washed with acetone and recrystallized from methanol-acetone to give 4-[(3S)-(3,4-dihydroxybutan-1-yl)oxy]-2-(1-piperazinyl)quinazoline monohydrochloride (697 mg) as crystals.

M.p.: 197–200° C. NMR (300 MHz, DMSO-d$_6$—D$_2$O, δppm): 1.7–1.9 (1H, m), 2.0–2.2 (1H, m), 3.22 (4H, m), 3.41 (2H, m), 3.74 (1H, m), 4.07 (4H, m), 4.63 (2H, m), 7.31 (1H, ddd, J=1, 7, 8 Hz), 7.52 (1H, d, J=8.5 Hz), 7.74 (1H, ddd, J=1.5, 7, 8.5 Hz), 7.95 (1H, dd, J=1.5, 8 Hz) Elementary analysis for C$_{16}$H$_{22}$N$_4$O$_3$ HCl ⅛H$_2$O: Calcd. (%): C,53.82; H,6.56; N,15.69 Found (%): C,53.82; H,6.50; N,15.81

EXAMPLE 59

4-[(3R)-(3,4-Dihydroxybutan-1-yl)oxy]-2-(1-piperazinyl)quinazoline:

(1) 2-[4-(Benzyloxycarbonyl)piperazin-1-yl]-4-[(3R)-(3,4-dihydroxybutan-1-yl)oxy]quinazoline:

To a mixture of AD-mix-β (manufactured by Aldrich Co.) (35.0 g), t-butanol (125 ml) and water (125 ml) is added 2-[4-(benzyloxycarbonyl)piperazin-1-yl]-4-[(3-buten-1-yl)oxy]quinazoline [cf. Example 57(2)] (10.46 g) with stirring under ice-cooling, and the mixture is stirred under ice-cooling for 60.5 hours. To the reaction mixture is added sodium sulfite (37.5 g), and the mixture is stirred at room temperature for 30 minutes. The reaction mixture is separated into an organic layer and an aqueous layer, and the aqueous layer is extracted with ethyl acetate. The organic layer is combined with the ethyl acetate extract, and washed with water. The ethyl acetate solution is dried over anhydrous magnesium sulfate, evaporated to dryness under reduced pressure, and the residue is purified by medium pressure liquid column chromatography [eluent, chloroform, (chloroform:methanol=50:1, v/v)], and the resulting crystalline product is recrystallized twice from acetone-diethyl ether to give 2-[4-(benzyloxycarbonyl)piperazin-1-yl]-4-[(3R)-(3,4-dihydroxybutan-1-yl)oxy]quinazoline (4.53 g) as crystals.

NMR (300 MHz, CDCl$_3$—D$_2$O, δppm): 1.9–2.2 (2H, m), 3.5–3.7 (5H, m), 3.75 (1H, dd, J=3.5, 11 Hz), 3.8–4.1 (5H, m), 4.61 (1H, m), 4.74 (1H, m), 5.18 (2H, s), 7.15 (1H, ddd, J=l, 7, 8 Hz), 7.3–7.4 (5H, m), 7.50 (1H, dt, J=1, 8.5 Hz), 7.61 (1H, ddd, J=1.5, 7, 8.5 Hz), 7.88 (1H, ddd, J=0.5, 1.5, 8 Hz) Elementary analysis for C$_{24}$H$_{28}$N$_4$O$_5$: Calcd. (%): C,63.70; H,6.24; N,12.38 Found (%): C,63.62; H,6.20; N,12.41

(2) 4-[(3R)-(3,4-Dihydroxybutan-1-yl)oxy]-2-(1-piperazinyl)quinazoline:

To a solution of 2-[4-(benzyloxycarbonyl)piperazin-1-yl]-4-[(3R)-(3,4-dihydroxybutan-1-yl)oxy]quinazoline (4.23 g) in methanol (40 ml) is added 10% palladium/carbon (634 mg), and the mixture is stirred under hydrogen atmosphere and under atmospheric pressure at room temperature for 18.5 hours. The reaction mixture is filtered, and the filtrate is evaporated to dryness under reduced pressure, and the residue is washed with acetone to give 4-[(3R)-(3,4-dihydroxybutan-1-yl)oxy]-2-(1-piperazinyl)quinazoline (2.13 g) as crystals. A part of the product is recrystallized from ethanol to give a product having the following physical properties.

M.p.: 151–156° C. [α]$_D^{20}$=+22° (c=1.0, methanol) NMR (300 MHz, DMSO-d$_6$—D$_2$O, δppm): 1.7–1.9 (1H, m), 2.0–2.2 (1H, m), 2.77 (4H, m), 3.40 (2H, m), 3.7–3.9 (5H, m), 4.58 (2H, m), 7.21 (1H, ddd, J=1, 7, 8 Hz), 7.44 (1H, d, J=8.5 Hz), 7.67 (1H, ddd, J=1.5, 7, 8.5 Hz), 7.88 (1H, dd, J=1.5, 8 Hz) Elementary analysis for C$_{16}$H$_{22}$N$_4$O$_3$: Calcd. (%): C,60.36; H,6.96; N,17.60 Found (%): C,60.20; H,7.01; N,17.70

EXAMPLE 60

4-[(3R)-(3,4-Dihydroxybutan-1-yl)oxy]-2-(1-piperazinyl)quinazoline monohydrochloride:

To a solution of 4-[(3R)-(3,4-dihydroxybutan-1-yl)oxy]-2-(1-piperazinyl)quinazoline (cf. Example 59) (1.90 g) in methanol (38 ml) is added 2N HCl-methanol (3.59 ml), and the mixture is evaporated to dryness under reduced pressure. The resulting residue is washed with acetone and recrystallized from methanol-acetone to give 4-[(3R)-(3,4-dihydroxybutan-1-yl)oxy]-2-(1-piperazinyl)quinazoline monohydrochloride (1.61 g) as crystals.

M.p.: 198–201° C. [α]$_D^{20}$=+13° (c=1.0, water) NMR (300 MHz, DMSO-d$_6$—D$_2$O, δppm): 1.7–1.9 (1H, m), 2.0–2.2 (1H, m), 3.23 (4H, m), 3.42 (2H, m), 3.75 (1H, m), 4.08 (4H, m), 4.63 (2H, m), 7.31 (1H, ddd, J=1, 7, 8 Hz), 7.52 (1H, d, J=8.5 Hz), 7.74 (1H, ddd, J=1.5, 7, 8.5 Hz), 7.95 (1H, dd, J=1.5, 8 Hz) Elementary analysis for C$_{16}$H$_{22}$N$_4$O$_3$ HCl: Calcd. (%): C,54.16; H,6.53; N,15.79 Found (%): C,53.94; H,6.50; N,15.79

EXAMPLE 61

4-[(2RS,3SR)-(2,3,4-Trihydroxybutan-1-yl)oxy]-2-(1-piperazinyl)quinazoline:

(1) 4-[cis-(4-Hydroxybut-2-en-1-yl)oxy]-2-(1-piperazinyl) quinazoline:

To a solution of cis-2-butene-1,4-diol (1.60 g) and 2,4-dichloroquinazoline (1.80 g) in dimethylformamide (18 ml) is added gradually 60% sodium hydride (in oil) (434 mg) with stirring under ice-cooling, and the mixture is stirred at room temperature for 2 hours. The reaction mixture is diluted with ethyl acetate and washed with water 5 times. The ethyl acetate solution is dried over anhydrous magnesium sulfate and evaporated to dryness under reduced pressure, and the residue is briefly purified by medium pressure liquid column chromatography (eluent, chloroform:methanol=100:1, v/v). The resulting oily substance is dissolved in dioxane (10 ml), and the solution is added dropwise to a solution of piperazine (3.89 g) in dioxane (40 ml) with stirring at 60° C., and the mixture is stirred at the same temperature for 1.5 hour. The reaction mixture is diluted with ethyl acetate, washed with water, and dried over anhydrous magnesium sulfate. The solution is evaporated to dryness under reduced pressure, and the residue is purified by medium pressure liquid column chromatography (eluent, chloroform:methanol=10:1, 5:1, v/v) to give 4-[cis-(4-hydroxybut-2-en-1-yl)oxy]-2-(1-piperazinyl) quinazoline (1.09 g) as crystals.

NMR (300 MHz, DMSO-d$_6$, δppm): 2.77 (4H, m), 3.22 (1H, br), 3.76 (4H, m), 4.15 (2H, d, J=4.5 Hz), 4.81 (1H, br), 5.09 (2H, m), 5.76 (2H, m), 7.16 (1H, ddd, J=1, 7, 8 Hz), 7.40 (1H, d, J=8.5 Hz), 7.64 (1H, ddd, J=1.5, 7, 8.5 Hz), 7.85 (1H, dd, J=1.5, 8 Hz)

(2) 2-[4-(Benzyloxycarbonyl)piperazin-1-yl]-4-[cis-(4-hydroxybut-2-en-1-yl)oxy]quinazoline:

To a solution of 4-[cis-(4-hydroxybut-2-en-1-yl)oxy]-2-(1-piperazinyl)quinazoline (1.09 g) in dry methylene chloride (25 ml) is added triethylamine (1.52 ml) with stirring under ice-cooling, and thereto is further added dropwise a solution of benzyl chlorocarbonate (0.62 ml) in dry methylene chloride (5 ml). The mixture is stirred under ice-cooling for 1.5 hour. The reaction mixture is diluted with chloroform, washed with water, and dried over anhydrous magnesium sulfate. The solution is evaporated to dryness under reduced pressure, and the residue is purified by medium pressure liquid column chromatography (eluent, chloroform:methanol=50:1, v/v) to give 2-[4-(benzyloxycarbonyl)piperazin-1-yl]-4-[cis-(4-hydroxybut-2-en-1-yl)oxy]quinazoline (1.52 g) as oil.

NMR (300 MHz, CDCl$_3$, δppm): 1.66 (1H, s), 3.62 (4H, m), 3.91 (4H, br), 4.36 (2H, m), 5.09 (2H, m), 5.18 (2H, s), 5.90 (2H, m), 7.15 (1H, ddd, J=1, 7, 8 Hz), 7.3–7.4 (5H, m), 7.50 (1H, d, J=8.5 Hz), 7.60 (1H, ddd, J=1.5, 7, 8.5 Hz), 7.92 (1H, ddd, J=0.5, 1.5, 8 Hz)

(3) 2-[4-(Benzyloxycarbonyl)piperazin-1-yl]-4-[(2RS,3SR)-(2,3,4-trihydroxybutan-1-yl)oxy]quinazoline:

A mixture of 4-[cis-(4-hydroxybut-2-en-1-yl)oxy]-2-(1-piperazinyl)quinazoline (1.40 g), a solution of osmium tetroxide in t-butanol (osmium tetroxide 106 mg/t-butanol 8.36 g) (686 mg) and 4-methylmorpholine N-oxide (434 mg) in water (3 ml)—acetone (28 ml) is stirred at room temperature for 6 hours. Acetone is distilled off from the reaction mixture under reduced pressure, and the resultant is diluted with ethyl acetate, and the mixture is washed with 10% aqueous sodium sulfite solution and water. The ethyl acetate solution is dried over anhydrous magnesium sulfate and evaporated to dryness under reduced pressure, and the residue is crystallized from methanol - isopropyl ether to give 2-[4-(benzyloxycarbonyl)piperazin-1-yl]-4-[(2RS,3SR)-(2,3,4 -trihydroxybutan-1-yl)oxy]quinazoline (891 mg) as crystals.

NMR (300 MHz, CDCl$_3$—D$_2$O, δppm): 3.60 (4H, m), 3.8–4.0 (7H, m), 4.11 (1H, dt, J=4.5, 7 Hz), 4.74 (2H, d, J=4.5 Hz), 5.17 (2H, s), 7.17 (1H, ddd, J=1, 7, 8 Hz), 7.2–7.4 (5H, m), 7.51 (1H, d, J=8.5 Hz), 7.62 (1H, ddd, J=1.5, 7, 8.5 Hz), 7.92 (1H, ddd, J=0.5, 1.5, 8 Hz)

(4) 4-[(2RS,3SR)-(2,3,4-Trihydroxybutan-1-yl)oxy]-2-(1-piperazinyl)quinazoline:

To a solution of 2-[4-(benzyloxycarbonyl)piperazin-1-yl]-4-[(2,3,4-trihydroxybutan-1-yl)oxy]quinazoline (800 mg) in methanol (6 ml)—dioxane (6 ml) is added 10% palladium/carbon (160 mg), and the mixture is stirred under hydrogen atmosphere and under atmospheric pressure at room temperature for 17 hours. The reaction mixture is filtered, and the filtrate is evaporated to dryness under reduced pressure. The residue is crystallized from acetone, and the resulting crystalline substance is recrystallized from ethanol-diethyl ether to give 4-[(2RS,3SR)-(2,3,4-trihydroxybutan-1-yl)oxy]-2-(1-piperazinyl)quinazoline (316 mg) as crystals.

M.p.: 168–172° C. NMR (300 MHz, DMSO-d$_6$—D$_2$O, δppm): 2.77 (4H, m), 3.4–3.9 (8H, m), 4.44 (1H, dd, J=6.5, 11.5 Hz), 4.66 (1H, dd, J=3, 11 Hz), 7.22 (1H, ddd, J=1, 7, 8 Hz), 7.45 (1H, d, J=8.5 Hz), 7.68 (1H, ddd, J=1.5, 7, 8.5 Hz), 7.98 (1H, dd, J=1.5, 8 Hz) Elementary analysis for C$_{16}$H$_{22}$N$_4$O$_4$: Calcd. (%): C,57.47; H,6.63; N,16.76 Found (%): C,57.30; H,6.81; N,16.56

EXAMPLE 62

4-[(2S,3S)-(2,3,4-Trihydroxybutan-1-yl)oxy]-2-(1-piperazinyl)quinazoline:

(1) 4-[(2S,3S)-(2,3-O-Isopropylidene-2,3,4-trihydroxybutan-1-yl)oxy]-2-(1-piperazinyl) quinazoline:

To a solution of 2,4-dichloroquinazoline (6.0 g) and (+)-2,3-O-isopropylidene-L-threitol (manufactured by Tokyo Kasei Kogyo K.K.) (5.0 g) in dimethylformamide (50 ml) is added gradually 60% sodium hydride (in oil) (1.2 g) with stirring under ice-cooling, and the mixture is stirred at room temperature for 2 hours. The reaction mixture is poured into ice-water and extracted with ethyl acetate. The extract is washed with water, dried over anhydrous sodium sulfate and evaporated to dryness under reduced pressure. The resulting residue is briefly purified by medium pressure liquid column chromatography (eluent, chloroform:methanol=100:1, v/v). The resulting crystalline substance is dissolved in dioxane (20 ml), and the solution is added dropwise to a solution of piperazine (6.9 g) in dioxane (100 ml) with stirring at 70° C., and the mixture is stirred at the same temperature for 1 hour. The reaction mixture is poured into water and extracted with chloroform. The extract is washed with water, dried over anhydrous sodium sulfate, and evaporated to dryness under reduced pressure. The resulting residue is purified by medium pressure liquid column chromatography (eluent, chloroform: methanol=5:1, v/v) to give 4-[(2S,3S)-(2,3-O-isopropylidene-2,3,4-trihydroxybutan-1-yl)oxy]-2-(1-piperazinyl)quinazoline (4.8 g) as oil.

NMR (300 MHz, CDCl$_3$, δppm): 1.50 (6H, s), 2.0–2.4 (2H, br), 2.96 (4H, m), 3.76 (1H, dd, J=4.5, 12 Hz), 3.8–4.0 (5H, m), 4.16 (1H, ddd, J=3.5, 4.5, 8 Hz), 4.38 (1H, dt, J=5, 8 Hz), 4.59 (1H, dd, J=5, 11.5 Hz), 4.70 (1H, dd, J=5, 11.5 Hz), 7.13 (1H, ddd, J=1, 7, 8 Hz), 7.49 (1H, dt, J=1, 8.5 Hz), 7.59 (1H, ddd, J=1.5, 7, 8.5 Hz), 7.90 (1H, ddd, J=0.5, 1.5, 8 Hz)

(2) 2-[4-(Benzyloxycarbonyl)piperazin-1-yl]-4-[(2S,3S)-(2,3-O-isopropylidene-2,3,4-trihydroxybutan-1-yl)oxy] quinazoline:

To a solution of 4-[(2S,3S)-(2,3-O-isopropylidene-2,3,4-trihydroxybutan-1-yl)oxy]-2-(1-piperazinyl)quinazoline (4.8 g) and triethylamine (2.6 g) in chloroform (50 ml) is added dropwise a solution of benzyl chlorocarbonate (2.1 g) in chloroform (10 ml) under ice-cooling, and the mixture is stirred at room temperature for 30 minutes. The reaction mixture is washed with water, dried over anhydrous sodium sulfate, and evaporated to dryness under reduced pressure. The resulting residue is purified by medium pressure liquid column chromatography (eluent, chloroform:methanol=100:1, v/v) to give 2-[4-(benzyloxycarbonyl)piperazin-1-yl]-4-[(2S,3S)-(2,3-O-isopropylidene-2,3,4-trihydroxybutan-1-yl)oxy]quinazoline (5.0 g) as oil.

NMR (300 MHz, CDCl$_3$, δppm): 1.49 (6H, s), 2.24 (1H, br), 3.60 (4H, m), 3.7–4.0 (6H, m), 4.16 (1H, ddd, J=3.5, 4, 8 Hz), 4.39 (1H, dt, J=5, 8 Hz), 4.59 (1H, dd, J=5, 11.5 Hz), 4.67 (1H, dd, J=5, 11.5 Hz), 5.17 (2H, s), 7.15 (1H, ddd, J=1, 7, 8 Hz), 7.2–7.4 (5H, m), 7.50 (1H, dt, J=1, 8.5 Hz), 7.60 (1H, ddd, J=1.5, 7, 8.5 Hz), 7.91 (1H, ddd, J=0.5, 1.5, 8 Hz)

(3) 2-[4-(Benzyloxycarbonyl)piperazin-1-yl]-4-[(2S,3S)-(2,3,4-trihydroxybutan-1-yl)oxy]quinazoline:

2-[4-(Benzyloxycarbonyl)piperazin-1-yl]-4-[(2S,3S)-(2,3-O-isopropylidene-2,3,4-trihydroxybutan-1-yl)oxy]-quinazoline (5.0 g) is dissolved in 80% aqueous acetic acid (50 ml), and the mixture is stirred at 100° C. overnight. To the reaction mixture is added water, and the mixture is made alkaline with 10% aqueous sodium hydroxide, and extracted with ethyl acetate. The extract is washed with water, dried over anhydrous sodium sulfate and evaporated to dryness under reduced pressure. The resulting residue is purified by medium pressure liquid column chromatography (eluent, chloroform:methanol=50:1, 30:1, v/v) to give 2-[4-(benzyloxycarbonyl)piperazin-1-yl]-4-[(2S,3S)-(2,3,4-trihydroxybutan-1-yl)oxy]quinazoline (2.3 g). A part of this product is recrystallized from chloroform to give a product having the following physical properties.

NMR (300 MHz, CDCl$_3$, δppm): 2.0–3.5 (3H, br), 3.60 (4H, m), 3.7–4.0 (7H, m), 4.19 (1H, m), 4.63 (2H, d, J=6 Hz), 5.17 (2H, s), 7.16 (1H, ddd, J=1, 7, 8 Hz), 7.2–7.4 (5H, m), 7.50 (1H, d, J=8.5 Hz), 7.62 (1H, ddd, J=1.5, 7, 8.5 Hz), 7.89 (1H, dd, J=1.5, 8 Hz)

(4) 4-[(2S,3S)-(2,3,4-Trihydroxybutan-1-yl)oxy]-2-(1-piperazinyl)quinazoline:

2-[4-(Benzyloxycarbonyl)piperazin-1-yl]-4-[(2S,3S)-(2,3,4-trihydroxybutan-1-yl)oxy]quinazoline (1.5 g) is dissolved in methanol (30 ml), and thereto is added 10% palladium/carbon (0.15 g), and the mixture is stirred under hydrogen atmosphere and under atmospheric pressure at room temperature for 17 hours. The reaction mixture is filtered, and the filtrate is evaporated to dryness under reduced pressure to give 4-[(2S,3S)-(2,3,4-trihydroxybutan-1-yl)oxy]-2-(1-piperazinyl)quinazoline (0.8 g).

NMR (300 MHz, DMSO-d$_6$, δppm): 2.76 (4H, m), 3.32 (1H, br), 3.4–3.7 (3H, m), 3.75 (4H, m), 4.00 (1H, m), 4.42 (1H, dd, J=7, 11 Hz), 4.50 (1H, dd, J=5, 11 Hz), 4.5–4.8 (2H, br), 4.87 (1H, br), 7.17 (1H, ddd, J=1, 7, 8 Hz), 7.39 (1H, d, J=8.5 Hz), 7.64 (1H, ddd, J=1.5, 7, 8.5 Hz), 7.90 (1H, dd, J=1.5, 8 Hz)

EXAMPLE 63

4-[(2S,3S)-(2,3,4-Trihydroxybutan-1-yl)oxy]-2-(1-piperazinyl)quinazoline monohydrochloride:

4-[(2S,3S)-(2,3,4-Trihydroxybutan-1-yl)oxy]-2-(1-piperazinyl)quinazoline (cf Example 62) (0.5 g) is dissolved in methanol (40 ml), and thereto is added 2N HCl-methanol (0.82 ml), and the mixture is evaporated to dryness under reduced pressure. The resulting residue is recrystallized from ethanol to give 4-[(2S,3S)-(2,3,4-trihydroxybutan-1-yl)oxy]-2-(1-piperazinyl)quinazoline monohydrochloride (0.21 g).

M.p.: 165–167° C.

NMR (300 MHz, DMSO-d$_6$, δppm): 3.19 (4H, m), 3.3–3.7 (3H, m), 3.9–4.2 (5H, m), 4.44 (1H, dd, J=7, 11 Hz), 4.56 (1H, dd, J=5, 11 Hz), 4.5–4.8 (2H, br), 4.92 (1H, br), 7.26 (1H, ddd, J=1, 7, 8 Hz), 7.48 (1H, d, J=8.5 Hz), 7.71 (1H, ddd, J=1.5, 7, 8.5 Hz), 7.96 (1H, dd, J=1.5, 8 Hz), 9.40 (2H, br) Elementary analysis for C$_{16}$H$_{22}$N$_4$O$_4$ HCl ½H$_2$O: Calcd. (%): C,48.30; H,6.59; N,14.08 Found (%): C,48.26; H,6.46; N,13.88

EXAMPLE 64

4-[(2R,3R)-(2,3,4-Trihydroxybutan-1-yl)oxy]-2-(1-piperazinyl)quinazoline:

(1) 4-[(2R,3R)-(2,3-O-Isopropylidene-2,3,4-trihydroxybutan-1-yl)oxy]-2-(1-piperazinyl)quinazoline:

To a solution of 2,4-dichloroquinazoline (6.0 g) and (−)-2,3-O-isopropylidene-D-threitol (manufactured by Wako Junyaku K.K.) (5.0 g) in dimethylformamide (50 ml) is added gradually 60% sodium hydride (in oil) (1.2 g) with stirring under ice-cooling, and the mixture is stirred at room temperature for 2 hours. The reaction mixture is poured into ice-water and extracted with ethyl acetate. The extract is washed with water, dried over anhydrous sodium sulfate and evaporated to dryness under reduced pressure. The resulting residue is briefly purified by medium pressure liquid column chromatography (eluent, chloroform:methanol=100:1, v/v). The resulting crystalline substance is dissolved in dioxane (20 ml), and the solution is added dropwise to a solution of piperazine (6.6 g) in dioxane (100 ml) with stirring at 70° C., and the mixture is stirred at the same temperature for 1 hour. The reaction mixture is poured into water and extracted with chloroform. The extract is washed with water, dried over anhydrous sodium sulfate, and evaporated to dryness under reduced pressure. The resulting residue is purified by medium pressure liquid column chromatography (eluent, chloroform:methanol=5:1, v/v) to give 4-[(2R,3R)-(2,3-O-isopropylidene-2,3,4-trihydroxybutan-1-yl)oxy]-2-(1-piperazinyl) quinazoline (4.2 g) as oil.

NMR (300 MHz, CDCl$_3$, δppm): 1.49 (6H, s), 2.0–2.4 (2H, br), 2.95 (4H, m), 3.76 (1H, dd, J=4.5, 12 Hz), 3.8–4.0 (5H, m), 4.15 (1H, ddd, J=3.5, 4.5, 8 Hz), 4.38 (1H, dt, J=5, 8 Hz), 4.59 (1H, dd, J=5, 11.5 Hz), 4.69 (1H, dd, J=5, 11.5 Hz), 7.13 (1H, ddd, J=1, 7, 8 Hz), 7.48 (1H, dt, J=1, 8.5 Hz), 7.59 (1H, ddd, J=1.5, 7, 8.5 Hz), 7.90 (1H, ddd, J=0.5, 1.5, 8 Hz)

(2) 2-[4-(Benzyloxycarbonyl)piperazin-1-yl]-4-[(2R,3R)-(2,3-O-isopropylidene-2,3,4-trihydroxybutan-1-yl)oxy]quinazoline:

To a solution of 4-[(2R,3R)-(2,3-O-isopropylidene-2,3,4-trihydroxybutan-1-yl)oxy]-2-(1-piperazinyl)quinazoline (4.2 g) and triethylamine (2.2 g) in chloroform (50 ml) is added dropwise a solution of benzyl chlorocarbonate (1.9 g) in chloroform (10 ml) under ice-cooling, and the mixture is stirred at room temperature for 30 minutes. The reaction mixture is washed with water, dried over anhydrous sodium sulfate, and evaporated to dryness under reduced pressure. The resulting residue is purified by medium pressure liquid column chromatography (eluent, chloroform:methanol=100:1, v/v) to give 2-[4-(benzyloxycarbonyl)piperazin-1-yl]-4-[(2R,3R)-(2,3-O-isopropylidene-2,3,4-trihydroxybutan-1-yl)oxy]quinazoline (5.7 g).

NMR (300 MHz, CDCl$_3$, δppm): 1.49 (6H, s), 1.92 (1H, m), 3.61 (4H1, m), 3.7–4.0 (6H, m), 4.16 (1H, ddd, J=3.5, 4, 8 Hz), 4.40 (1H, dt, J=5, 8 Hz), 4.59 (1H, dd, J=5, 11.5 Hz), 4.68 (1H, dd, J=5, 11.5 Hz), 5.18 (2H, s), 7.16 (1H, ddd, J=1, 7, 8 Hz), 7.2–7.4 (5H, m), 7.50 (1H, dt, J=1, 8.5 Hz), 7.62 (1H, ddd, J=1.5, 7, 8.5 Hz), 7.91 (1H, ddd, J=0.5, 1.5, 8 Hz)

(3) 2-[4-(Benzyloxycarbonyl)piperazin-1-yl]-4-[(2R,3R)-(2,3,4-trihydroxybutan-1-yl)oxy]quinazoline:

2-[4-(Benzyloxycarbonyl)piperazin-1-yl]-4-[(2R,3R)-(2,3-O-isopropylidene-2,3,4-trihydroxybutan-1-yl)oxy] quinazoline (5.7 g) is dissolved in 80% aqueous acetic acid (50 ml), and the mixture is stirred at 100° C. overnight. To the reaction mixture is added water, and the mixture is made alkaline with 10% aqueous sodium hydroxide, and extracted with ethyl acetate. The extract is washed with water, dried over anhydrous sodium sulfate and evaporated to dryness under reduced pressure. The resulting residue is purified by medium pressure liquid column chromatography (eluent, chloroform:methanol=50:1, 30:1, v/v) to give 2-[4-(benzyloxycarbonyl)piperazin-1-yl]-4-[(2R,3R)-(2,3,4-trihydroxybutan-1-yl)oxy]quinazoline (2.5 g).

NMR (300 MHz, CDCl$_3$, δppm): 2.0–3.5 (3H, br), 3.59 (4H, m), 3.7–4.0 (7H, m), 4.18 (1H, m), 4.61 (2H, d, J=6 Hz), 5.17 (2H, s), 7.15 (1H, ddd, J=1, 7, 8 Hz), 7.2–7.4 (5H, m), 7.50 (1H, d, J=8.5 Hz), 7.61 (1H, ddd, J=1.5, 7, 8.5 Hz), 7.88 (1H, dd, J=1.5, 8 Hz)

(4) 4-[(2R,3R)-(2,3,4-Trihydroxybutan-1-yl)oxy]-2-(1-piperazinyl)quinazoline:

2-[4-(Benzyloxycarbonyl)piperazin-1-yl]-4-[(2R,3R)-(2,3,4-trihydroxybutan-1-yl)oxy]quinazoline (1.5 g) is dissolved in methanol (40 ml), and thereto is added 1% palladium/carbon (0.15 g), and the mixture is stirred under hydrogen atmosphere and under atmospheric pressure at room temperature for 20 hours. The reaction mixture is filtered, and the filtrate is evaporated to dryness under reduced pressure to give 4-[(2R,3R)-(2,3,4-trihydroxybutan-1-yl)oxy]-2-(1-piperazinyl)quinazoline (1.0 g). A part of this product is recrystallized from ethanol to give a product having the following physical properties.

NMR (300 MHz, DMSO-$d_6$, δppm): 2.76 (4H, m), 3.34 (1H, br), 3.3–3.7 (3H, m), 3.75 (4H, m), 4.00 (1H, m), 4.42 (1H, dd, J=7, 11 Hz), 4.50 (1H, dd, J=5, 11 Hz), 4.5–4.8 (2H1, br), 4.86 (1H, br), 7.17 (1H, ddd, J=1, 7, 8 Hz), 7.39 (1H, d, J=8.5 Hz), 7.63 (1H, ddd, J=1.5, 7, 8.5 Hz), 7.90 (1H, dd, J=1.5, 8 Hz)

EXAMPLE 65

4-[(2R,3R)-(2,3,4-Trihydroxybutan-1-yl)oxy]-2-(1-piperazinyl)quinazoline monohydrochloride:

4-[(2R,3R)-(2,3,4-Trihydroxybutan-1-yl)oxy]-2-(1-piperazinyl)quinazoline (cf Example 64) (0.5 g) is dissolved in methanol (40 ml), and thereto is added 2N HCl-methanol (0.82 ml), and the mixture is evaporated to dryness under reduced pressure. The resulting residue is recrystallized from ethanol to give 4-[(2R,3R)-(2,3,4-trihydroxybutan-1-yl)oxy]-2-(1-piperazinyl)quinazoline monohydrochloride (0.14 g).

M.p.: 165–167° C. NMR (300 MHz, DMSO-$d_6$, δppm): 3.18 (4H, m), 3.3–3.7 (3H, m), 3.9–4.2 (5H, m), 4.44 (1H, dd, J=7, 11 Hz), 4.56 (1H, dd, J=5, 11 Hz), 4.5–4.8 (2H, br), 4.91 (1H, br), 7.26 (1H, ddd, J=1, 7, 8 Hz), 7.48 (1H, d, J=8.5 Hz), 7.71 (1H, ddd, J=1.5, 7, 8.5 Hz), 7.96 (1H, dd, J=1.5, 8 Hz), 9.39 (2H, br) Elementary analysis for $C_{16}H_{22}N_4O_4$ HCl ¾$H_2O$: Calcd. (%): C,50.00; H,6.43; N,14.58 Found (%): C,50.06; H,6.57; N,14.36

EXAMPLE 66

4-[(2R)-(2,3-Dihydroxypropan-1-yl)oxy]-2-(1-piperazinyl)quinazoline:

(1) 4-[(2S)-(2,3-O-Isopropylidiene-2,3-dihydroxypropan-1-yl)oxy]-2-(1-piperazinyl)quinazoline:

To a solution of 2,4-dichloroquinazoline (6.0 g) and (S)-(+)-2,2-dimethyl-1,3-dioxolane-4-methanol (manufactured by Tokyo Kasei Kogyo K.K.) (4.0 g) in tetrahydrofuran (50 ml) is added gradually potassium t-butoxide (4.1 g), and the mixture is stirred at room temperature for 2 hours. The reaction mixture is poured into water and extracted with ethyl acetate. The extract is washed with water, dried over anhydrous sodium sulfate and evaporated to dryness under reduced pressure to give an oily substance. The oily substance is dissolved in dioxane (50 ml), and the solution is added dropwise to a solution of piperazine (12.9 g) in dioxane (100 ml) with stirring at 70° C., and the mixture is stirred at the same temperature for 1 hour. The reaction mixture is poured into water and extracted with ethylacetate. The extract is washed with water, dried over anhydrous sodium sulfate, and evaporated to dryness under reduced pressure. The resulting residue is purified by medium pressure liquid column chromatography (eluent, chloroform:methanol=40:1, 10:1, v/v) to give 4-[(2S)-(2,3-O-isopropylidene-2,3-dihydroxypropan-1-yl)oxy]-2-(1-piperazinyl)-quinazoline (7.3 g) as oil.

NMR (250 MHz, CDCl$_3$, δppm): 1.42 (3H, s), 1.49 (3H, s), 1.81 (1H, s), 2.96 (4H, m), 3.89 (4H, m), 3.98 (1H, dd, J=5.5, 8.5 Hz), 4.20 (1H, dd, J=6.5, 8.5 Hz), 4.4–4.7 (3H, m), 7.13 (1H, ddd, J=1, 7, 8 Hz), 7.49 (1H, dt, J=1, 8.5 Hz), 7.59 (1H, ddd, J=1.5, 7, 8.5 Hz), 7.92 (1H, ddd, J=0.5, 1.5, 8 Hz)

(2) 2-[4-(Benzyloxycarbonyl)piperazin-1-yl]-4-[(2S)-(2,3-O-isopropylidene-2,3-dihydroxypropan-1-yl)oxy]quinazoline:

To a solution of 4-[(2S)-(2,3-O-isopropylidene-2,3-dihydroxypropan-1-yl) oxy]-2-(1-piperazinyl) quinazoline (7.3 g) and triethylamine (4.8 g) in chloroform (50 ml) is added dropwise a solution of benzyl chlorocarbonate (4.9 g) in chloroform (10 ml) under ice-cooling, and the mixture is stirred at room temperature for one hour. The reaction mixture is washed with water, dried over anhydrous sodium sulfate, and evaporated to dryness under reduced pressure. The resulting residue is purified by medium pressure liquid column chromatography (eluent, chloroform:methanol=100:1, v/v) to give 2-[4-(benzyloxycarbonyl)piperazin-1-yl]-4-[(2S)-(2,3-O-isopropylidene-2,3-dihydroxypropan-1-yl)oxy]quinazoline (10 g).

NMR (250 MHz, CDCl$_3$, δppm): 1.42 (3H, s), 1.50 (3H, s), 3.61 (4H, m), 3.90 (4H, m), 3.98 (1H, dd, J=5.5, 8.5 Hz), 4.20 (1H, dd, J=6.5, 8.5 Hz), 4.4–4.7 (3H, m), 5.18 (2H, s), 7.16 (1H, ddd, J=1, 7, 8 Hz), 7.2–7.4 (5H, m), 7.49 (1H, ddd, J=0.5, 1, 8.5 Hz), 7.61 (1H, ddd, J=1.5, 7, 8.5 Hz), 7.93 (1H, dd, J=1, 8 Hz)

(3) 2-[4-(Benzyloxycarbonyl)piperazin-1-yl]-4-[(2R)-(2,3-dihydroxypropan-1-yl)oxy]quinazoline:

2-[4-(Benzyloxycarbonyl)piperazin-1-yl]-4-[(2S)-(2,3-O-isopropylidene-2,3-dihydroxypropan-1-yl)oxy] quinazoline (5.5 g) is dissolved in 80% aqueous acetic acid (100 ml), and the mixture is stirred at 70° C. overnight. The reaction mixture is concentrated under reduced pressure, and the resultant is made alkaline with 10% aqueous sodium hydroxide, and extracted with ethyl acetate. The extract is washed with water, dried over anhydrous sodium sulfate and evaporated to dryness under reduced pressure. The resulting residue is purified by medium pressure liquid column chromatography (eluent, chloroform:methanol=100:1, v/v) to give 2-[4-(benzyloxycarbonyl)piperazin-1-yl]-4-[(2R)-(2,3-dihydroxypropan-1-yl)oxy]quinazoline (3.0 g).

NMR (250 MHz, CDCl$_3$, δppm): 2.0–3.0 (2H, br), 3.6 (4H, m), 3.75 (1H, dd, J=5.5, 11.5 Hz), 3.8–4.0 (5H, m), 4.21 (1H, m), 4.59 (2H, d, J=5.5 Hz), 5.18 (2H, s), 7.17 (1H, ddd, J=1, 7, 8Hz), 7.3–7.4 (5H, m), 7.51 (1H, d, J=8.5 Hz), 7.62 (1H, ddd, J=1.5, 7, 8.5 Hz), 7.93 (1H, dd, J=1.5, 8 Hz)

(4) 4-[(2R)-(2,3-Dihydroxypropan-1-yl)oxy]-2-(1-piperazinyl)quinazoline:

2-[4-(Benzyloxycarbonyl)piperazin-1-yl]-4-[(2R)-(2,3-dihydroxypropan-1-yl)oxy]quinazoline (5.8 g) is dissolved in methanol (50 ml), and thereto is added 10% palladium/carbon (0.6 g), and the mixture is stirred under hydrogen atmosphere and under atmospheric pressure at room temperature overnight. The reaction mixture is filtered, and the filtrate is evaporated to dryness under reduced pressure, and the residue is recrystallized from methanol to give 4-[(2R)-(2,3-dihydroxypropan-1-yl)oxy]-2-(1-piperazinyl) quinazoline (1.4 g).

M.p.: 170–171° C.

NMR (250 MHz, DMSO-$d_6$, δppm): 2.75 (4H, m), 3.35 (1H, br), 3.51 (2H, br), 3.74 (4H, m), 3.91 (1H, m), 4.34 (1H, dd, J=6.5, 11 Hz), 4.53 (1H, dd, J=4, 11 Hz), 4.75 (1H, br), 5.08 (1H, m), 7.17 (1H, ddd, J=1, 7, 8 Hz), 7.40 (1H, d, J=8.5

Hz), 7.64 (1H, ddd, J=1.5, 7, 8.5 Hz), 7.92 (1H, dd, J=1, 8 Hz) Elementary analysis for $C_{15}H_{20}N_4O_3$: Calcd. (%): C,59.20; H,6.62; N,18.41 Found (%): C,59.13; H,6.55; N,18.38

EXAMPLE 67
Preparation of Tablets:
[Formulation]

| Components | Amount (g) |
|---|---|
| 4-[(t-3,t-4-Dihydroxycyclopentan-r-1-yl)oxy]-2-(1-piperazinyl)quinazoline monohydrochloride | 100 |
| Lactose | 890 |
| Crystalline cellulose | 900 |
| Carboxymethyl cellulose calcium | 70 |
| Talc | 25 |
| Magnesium stearate | 15 |
| Totally | 2000 |

[Procedure]
The components are homogeneously mixed and tabletted to form tablets, each having a weight of 200 mg.

EXAMPLE 68
Preparation of Powders:
[Formulation]

| Components | Amount (g) |
|---|---|
| 4-[(t-3,t-4-Dihydroxycyclopentan-r-1-yl)oxy]-2-(1-piperazinyl)quinoline monohydrochloride | 20 |
| Lactose | 580 |
| Starch | 400 |
| Totally | 1000 |

[Procedure]
The components are homogeneously mixed to form powders containing 20 mg of the active ingredient per 1 g of the powders.

EXAMPLE 69
Preparation of Injections:
4-[(t-3,t-4-Dihydroxycyclopentan-r-1-yl)oxy]-2-(1-piperazinyl)quinazoline monohydrochloride (5 g) is dissolved in distilled water for injection to make totally 1000 ml. The solution is filtered with sterilization paper and filled in ampoules (each content, 1 ml) and then sealed.

EXAMPLES 70, 71 and 72

In the same manner as described in Examples 67, 68 and 69 except that as the active ingredient 4-[(1R,2R,3S,4S)-(2,3-dihydroxy-4-methoxycyclopentan-1-yl)oxy]-2-(1-piperazinyl)quinazoline monohydrochloride (Compound AT of the present invention) is used instead of 4-[(t-3,t-4-dihydroxycyclopentan-r-1-yl)oxy]-2-(1-piperazinyl) quinazoline monohydrochloride, there are prepared tablets, powders and injections which contain the Compound AT as the active ingredient.

EXAMPLES 73, 74 and 75

In the same manner as described in Examples 67, 68 and 69 except that as the active ingredient 4-[(3R,4R)-(4-hydroxytetrahydrofuran-3-yl)oxy]-2-(1-piperazinyl) quinazoline ½ hydrochloride (Compound AJ of the present invention) is used instead of 4-[(t-3,t-4-dihydroxycyclopentan-r-1-yl)oxy]-2-(1-piperazinyl) quinazoline monohydrochloride, there are prepared tablets, powders and injections which contain the Compound AJ as the active ingredient.

EXAMPLES 76, 77 and 78

In the same manner as described in Examples 67, 68 and 69 except that as the active ingredient 4-[(3S,4S)-(4-hydroxytetrahydrofuran-3-yl)oxy]-2-(1-piperazinyl) quinazoline monoacetate (Compound AH of the present invention) is used instead of 4-[(t-3,t-4-dihydroxycyclopentan-r-1-yl)oxy]-2-(1-piperazinyl) quinazoline monohydrochloride, there are prepared tablets, powders and injections which contain the Compound AH as the active ingredient.

EXAMPLE 79
Preparation of Tablets:
[Formulation]

| Components | Amount (g) |
|---|---|
| 4-[(3R)-(3,4-Dihydroxybutan-1-yl)oxy]-2-(1-piperazinyl)quinazoline monohydrochloride | 100 |
| Lactose | 890 |
| Crystalline cellulose | 900 |
| Carboxymethyl cellulose calcium | 70 |
| Talc | 25 |
| Magnesium stearate | 15 |
| Totally | 2000 |

[Procedure]
The components are homogeneously mixed and tabletted to form tablets, each having a weight of 200 mg.

EXAMPLE 80
Preparation of Powders:
[Formulation]

| Components | Amount (g) |
|---|---|
| 4-[(3R)-(3,4-Dihydroxybutan-1-yl)oxy]-2-(1-piperazinyl)quinazoline monohydrochloride | 20 |
| Lactose | 500 |
| Starch | 480 |
| Totally | 1000 |

[Procedure]
The components are homogeneously mixed to form powders containing 20 mg of the active ingredient per 1 g of the powders.

EXAMPLE 81
Preparation of Injections:
4-[(3R)-(3,4-Dihydroxybutan-1-yl)oxy]-2-(1-piperazinyl)quinazoline monohydrochloride (5 g) is dissolved in distilled water for injection to make totally 1000 ml, and the solution is filtered with sterilization paper and filled in ampoules (each content, 1 ml). After being subjected to lyophilization, the ampoules are sealed to give injections which are dissolved in a saline solution when used.

What is claimed is:

1. A quinazoline compound of the formula (I-A):

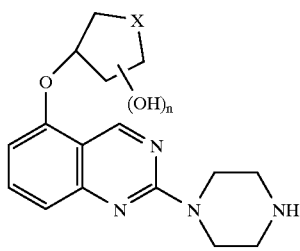

(I-A)

wherein X means methylene, hydroxymethine, methoxymethine, or oxygen atom, and n is an integer of 1 to 3),
or a pharmaceutically acceptable acid addition salt thereof.

2. A quinazoline compound according to claim 1, wherein X is hydroxymethine, or a pharmaceutically acceptable acid addition salt thereof.

3. A quinazoline compound according to claim 1, wherein X is methoxymethine, or a pharmaceutically acceptable acid addition salt thereof.

4. A quinazoline compound according to claim 1, wherein X is oxygen atom, or a pharmaceutically acceptable acid addition salt thereof.

5. A quinazoline compound according to claim 1, wherein n is 1 or 2, or a pharmaceutically acceptable acid addition salt thereof.

6. A quinazoline compound according to claim 2, wherein n is 1 or 2, or a pharmaceutically acceptable acid addition salt thereof.

7. A quinazoline compound according to claim 3, wherein n is 1 or 2, or a pharmaceutically acceptable acid addition salt thereof.

8. A quinazoline compound according to claim 1 which is 4-[(t-3,t-4-dihydroxycyclopentan-r-1-yl)oxy]-2-(1-piperazinyl)quinazoline, or a pharmaceutically acceptable acid addition salt thereof.

9. A quinazoline compound according to claim 1, which is 4-[(1R,2R,3S,4S)-(2,3-dihydroxy-4-methoxy-cyclopentan-1-yl)oxy-2-(1-piperazinyl)quinazoline or a pharmaceutically acceptable acid addition salt thereof.

10. A quinazoline compound according to claim 1, which is 4-[(3R,4R)-(4-hydroxytetrahydrofuran-3-yl)oxy]-2-(1-piperazinyl)quinazoline or a pharmaceutically acceptable acid addition salt thereof.

11. A quinazoline compound according to claim 1, which is 4-[(3S,4S)-(4-hydroxytetrahydrofuran-3-yl)oxy]-2-(1-piperazinyl)quinazoline or a pharmaceutically acceptable acid addition salt thereof.

12. A quinazoline compound of the formula (I-B):

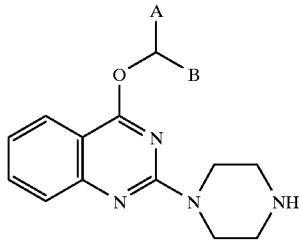

(I-B)

wherein A is hydrogen atom or methyl, and B is hydroxymethyl, or ethyl having one or two hydroxy substituents, or propyl having two or three hydroxy substituents), or a pharmaceutically acceptable acid addition salt thereof.

13. A quinazoline compound according to claim 12, wherein A is hydrogen atom and B is n-propyl having two or three hydroxy substituents, or a pharmaceutically acceptable acid addition salt thereof.

14. A quinazoline compound according to claim 12, wherein A is hydrogen atom and B is n-propyl having two hydroxy substituents, or a pharmaceutically acceptable acid addition salt thereof.

15. A quinazoline compound according to claim 12, which is 4-[(3R)-(3,4-dihydroxybutan-1-yl)oxy]-2-(1-piperazinyl)quinazoline, or a pharmaceutically acceptable salt thereof.

16. A quinazoline compound according to claim 12, which is 4-[(2RS,3RS)-(2,3-dihydroxybutan-1-yl)oxy]-2-(1-piperazinyl)quinazoline, or a pharmaceutically acceptable salt thereof.

17. A quinazoline compound according to claim 12, which is 4-[(2S,3S)-(2,3-dihydroxybutan-1-yl)oxy]-2-(1-piperazinyl)quinazoline, or a pharmaceutically acceptable salt thereof.

18. A quinazoline compound according to claim 12, which is 4-[(2R,3R)-(2,3-dihydroxybutan-1-yl)oxy]-2-(1-piperazinyl)quinazoline, or a pharmaceutically acceptable salt thereof.

19. A pharmaceutical composition useful as an anti-tumor agent, which comprises as an active ingredient an effective amount of a quinazoline compound of the formula (I-A):

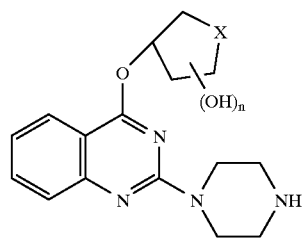

(I-A)

wherein X means methylene, hydroxymethine, methoxymethine, or oxygen atom, and n is an integer of 1 to 3), or a pharmaceutically acceptable acid addition salt thereof in admixture with a conventional pharmaceutically acceptable carrier or diluent.

20. A pharmaceutical composition according to claim 19, wherein the active ingredient is a quinazoline compound as set forth in claim 19 in which X is hydroxymethine, or a pharmaceutically acceptable acid addition salt thereof in admixture with a conventional pharmaceutically acceptable carrier or diluent.

21. A pharmaceutical composition according to claim 19, wherein the active ingredient is a quinazoline compound as set forth in claim 19 in which X is methoxymethine, or a pharmaceutically acceptable acid addition salt thereof in admixture with a conventional pharmaceutically acceptable carrier or diluent.

22. A pharmaceutical composition according to claim 19, wherein the active ingredient is a quinazoline compound as set forth in claim 19 in which X is oxygen atom, or a pharmaceutically acceptable acid addition salt thereof in admixture with a conventional pharmaceutically acceptable carrier or diluent.

23. A pharmaceutical composition according to claim 19, wherein n is 1 or 2.

24. A pharmaceutical composition useful as an anti-tumor agent according to claim 19, which comprises as an active ingredient an effective amount of 4-[(t-3,t-4-dihydroxycyclopentan-r-1-yl)oxy]-2-(1-piperazinyl)quinazoline, or a pharmaceutically acceptable acid addition salt thereof in admixture with a conventional pharmaceutically acceptable carrier or diluent.

25. A pharmaceutical composition useful as an anti-tumor agent, according to claim 19 which comprises as an active ingredient an effective amount of 4-[(1R,2R,3S,4S)-(2,3-Dihydroxy-4-methoxycyclopentan-1-yl)oxy]-2-(1-piperazinyl)quinazoline, or a pharmaceutically acceptable acid addition salt thereof in admixture with a conventional pharmaceutically acceptable carrier or diluent.

26. A pharmaceutical composition useful as an anti-tumor agent according to claim 19, which comprises as an active ingredient an effective amount of 4-[(3R,4R)-(4-Hydroxytetrahydrofuran-3-yl)oxy]-2-(1-piperazinyl)quinazoline, or a pharmaceutically acceptable acid addition salt thereof in admixture with a conventional pharmaceutically acceptable carrier or diluent.

27. A pharmaceutical composition useful as an anti-tumor agent, according to claim 19 which comprises as an active ingredient an effective amount of 4-[(3S,4S)-(4-Hydroxytetrahydrofuran-3-yl)oxy]-2-(1-piperazinyl)quinazoline, or a pharmaceutically acceptable acid addition salt thereof in admixture with a conventional pharmaceutically acceptable carrier or diluent.

28. A pharmaceutical composition useful as an anti-tumor agent, which comprises as an active ingredient an effective amount of a quinazoline compound of the formula (I-B):

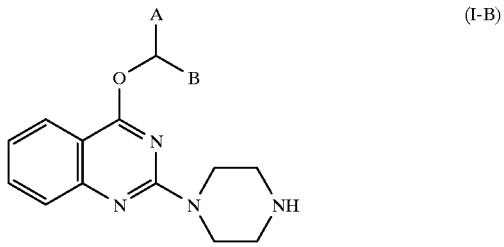

wherein A is hydrogen atom or methyl, and B is hydroxymethyl, or ethyl having one or two hydroxy substituents, or propyl having two or three hydroxy substituents), or a pharmaceutically acceptabel acid addition salt thereof in admixture with a conventional pharmaceutically acceptable carrier or diluent.

29. A pharmaceutical composition according to claim 28, wherein the active ingredient is a quinazoline compound as set forth in claim 28, in which A is hydrogen atom and B is n-propyl having two or three hydroxy substituents, or a pharmaceutically acceptable acid addition salt thereof in admixture with a conventional pharmaceutically acceptable carrier or diluent.

30. A pharmaceutical composition according to claim 28, wherein the active ingredient is a quinazoline compound as set forth in claim 28, in which A is hydrogen atom and B is n-propyl having two hydroxy substituents, or a pharmaceutically acceptable acid addition salt thereof in admixture with a conventional pharmaceutically acceptable carrier or diluent.

31. A pharmaceutical composition useful as an anti-tumor agent according to claim 28, which comprises as an active ingredient an effective amount of 4-[(3R)-(3,4-dihydroxybutan-1-yl)oxy]-2-(1-piperazinyl)quinazoline, or a pharmaceutically acceptable acid addition salt thereof in admixture with a conventional pharmaceutically acceptable carrier or diluent.

32. A pharmaceutical composition useful as an anti-tumor agent, according to claim 28 which comprises as an active ingredient an effective amount of 4-[(2RS,3RS)-(2,3-dihydroxybutan-1-yl)oxy]-2-(1-piperazinyl)quinazoline, or a pharmaceutically acceptable acid addition salt thereof in admixture with a conventional pharmaceutically acceptable carrier or diluent.

33. A pharmaceutical composition useful as an anti-tumor agent, according to claim 28 which comprises as an active ingredient an effective amount of 4-[(2S,3S)-(2,3-dihydroxybutan-1-yl)oxy]-2-(1-piperazinyl)quinazoline, or a pharmaceutically acceptable acid addition salt thereof in admixture with a conventional pharmaceutically acceptable carrier or diluent.

34. A pharmaceutical composition useful as an anti-tumor agent according to claim 28, which comprises as an active ingredient an effective amount of 4-[(2R,3R)-(2,3-dihydroxybutan-1-yl)oxy]-2-(1-piperazinyl)quinazoline, or a pharmaceutically acceptable acid addition salt thereof in admixture with a conventional pharmaceutically acceptable carrier or diluent.

* * * * *